(12) United States Patent  (10) Patent No.: US 8,377,079 B2
Coe et al.  (45) Date of Patent: Feb. 19, 2013

(54) CONSTANT FORCE MECHANISMS FOR REGULATING RESTRICTION DEVICES

(75) Inventors: Jonathan A. Coe, Cincinnati, OH (US); Mark S. Ortiz, Milford, OH (US); Kyle P. Moore, Mason, OH (US); Mark D. Overmyer, Grandville, MI (US); Thomas E. Adams, Maineville, OH (US); Andrew M. Zwolinski, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1096 days.

(21) Appl. No.: 11/965,322

(22) Filed: Dec. 27, 2007

(65) Prior Publication Data

US 2009/0171378 A1  Jul. 2, 2009

(51) Int. Cl.
*A61B 17/12* (2006.01)
*F16J 3/04* (2006.01)
*F16J 3/06* (2006.01)

(52) U.S. Cl. .............................. 606/151; 600/37; 92/40

(58) Field of Classification Search .................. 606/151; 600/37, 29–31; 138/31, 46; 137/224; 92/36, 92/40, 89–92, 94, 95; 417/540
See application file for complete search history.

(56) References Cited

U.S. PATENT DOCUMENTS

| RE3,036 E | 7/1868 | Shunk |
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |
| 322,388 A | 7/1885 | Lord |
| 400,401 A | 3/1889 | Gutzkow |
| D23,637 S | 9/1894 | Casad et al. |

(Continued)

FOREIGN PATENT DOCUMENTS

| CA | 1059035 | 7/1979 |
| CA | 1119469 | 3/1982 |

(Continued)

OTHER PUBLICATIONS

"Application Specific Integrated Circuits (ASICs)", Honeywell product information from website http://www.honeywell.com/sites/portal?smap=aerospace&page=Radiation-Hardened-Electronics3&theme=T18&catID=CE06BEF88-65F8-6A1E-4ED1-6A1EC1B7AE7A&id=HA0E380D3-C27B-9EBF-AAC8-9FAF8851256D&sel=1&sel4=1; 1 page.

(Continued)

*Primary Examiner* — Julian Woo
*Assistant Examiner* — Christopher L Templeton
(74) *Attorney, Agent, or Firm* — Nutter McClennen & Fish LLP

(57) ABSTRACT

Methods and devices are provided for regulating a restriction system. In one exemplary embodiment, a restriction system is provided having a restriction device coupled to a port with a fluid disposed in the device, such that the restriction device is adapted to form a restriction in a pathway corresponding to an amount of fluid contained in the device, and a pressure adjustment unit in communication with the port and effective to maintain a substantially constant equilibrium pressure between the pressure adjustment unit and the restriction device. The pressure adjustment unit is configured to regulate an amount of fluid in the restriction device in response to a fluid pressure acting on the device.

9 Claims, 15 Drawing Sheets

U.S. PATENT DOCUMENTS

| | | |
|---|---|---|
| D24,900 S | 11/1895 | Clemecet |
| D25,318 S | 3/1896 | Perky |
| D27,151 S | 6/1897 | Moulten |
| D29,715 S | 11/1898 | Wheeler |
| D29,745 S | 11/1898 | Bunker |
| D29,885 S | 12/1898 | Gillespie et al. |
| D30,690 S | 5/1899 | Schwedtmann |
| D30,966 S | 6/1899 | Howe |
| D31,230 S | 7/1899 | Hogan |
| 689,758 A | 12/1901 | Shaw |
| 724,913 A | 4/1903 | Montgomery |
| 899,477 A | 9/1908 | Williams |
| 926,197 A | 6/1909 | Kim |
| 953,875 A | 4/1910 | Waring |
| 991,192 A | 5/1911 | Batttenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | Cheron |
| 1,620,633 A | 3/1927 | Colvin |
| 1,623,403 A | 4/1927 | Friel |
| 1,689,085 A | 10/1928 | Russell et al. |
| 1,764,071 A | 6/1930 | Foulke |
| 1,782,704 A | 11/1930 | Woodruff |
| 1,807,107 A | 5/1931 | Sternberch |
| 1,865,446 A | 7/1932 | Sears |
| 1,882,338 A | 10/1932 | Reed et al. |
| 1,924,781 A | 8/1933 | Gaiser |
| 2,027,875 A | 1/1936 | Odend'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,177,564 A | 10/1939 | Havill |
| 2,178,463 A | 10/1939 | Bahnson |
| 2,180,599 A | 11/1939 | Menasco |
| 2,203,460 A | 6/1940 | Fieber |
| 2,206,038 A | 7/1940 | Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,303,502 A | 12/1942 | Rous |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,426,392 A | 8/1947 | Fennema |
| 2,426,817 A | 9/1947 | Charlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,509,210 A | 5/1950 | Clark |
| 2,509,673 A | 5/1950 | Church |
| 2,511,765 A | 6/1950 | Bradbury |
| 2,520,056 A | 8/1950 | Pozun |
| 2,521,976 A | 9/1950 | Hays |
| 2,533,924 A | 12/1950 | Foley |
| 2,538,259 A | 1/1951 | Merriman |
| 2,581,479 A | 1/1952 | Grashman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | Martin |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,040,800 A | 6/1962 | Hartley |
| 3,054,618 A | 9/1962 | Abrams et al. |
| 3,060,262 A | 10/1962 | Hoer |
| 3,070,373 A | 12/1962 | Mathews et al. |
| 3,082,414 A | 3/1963 | Papaminas |
| 3,085,577 A | 4/1963 | Berman et al. |
| 3,096,410 A | 7/1963 | Anderson |
| 3,099,262 A | 7/1963 | Bigliano |
| 3,125,028 A | 3/1964 | Rohde |
| 3,126,029 A | 3/1964 | Englesson |
| 3,129,072 A | 4/1964 | Cook et al. |
| 3,135,914 A | 6/1964 | Callan et al. |
| 3,144,017 A | 8/1964 | Muth |
| 3,151,258 A | 9/1964 | Sonderegger et al. |
| 3,153,460 A | 10/1964 | Raskin |
| 3,161,051 A | 12/1964 | Perry, Jr. |
| 3,167,044 A | 1/1965 | Henrickson |
| 3,171,549 A | 3/1965 | Orloff |
| 3,172,700 A | 3/1965 | Haas |
| 3,173,269 A | 3/1965 | Imbertson |

| Patent | Date | Name |
|---|---|---|
| 3,182,494 A | 5/1965 | Beatty et al. |
| 3,187,181 A | 6/1965 | Keller |
| 3,187,745 A | 6/1965 | Baum et al. |
| 3,190,388 A | 6/1965 | Moser et al. |
| 3,205,547 A | 9/1965 | Riekse |
| 3,208,255 A | 9/1965 | Burk |
| 3,209,570 A | 10/1965 | Hills |
| 3,221,468 A | 12/1965 | Casey |
| 3,228,703 A | 1/1966 | Wilson |
| 3,229,684 A | 1/1966 | Nagumo et al. |
| 3,236,088 A | 2/1966 | Moller |
| 3,238,624 A | 3/1966 | McCabe |
| 3,240,510 A | 3/1966 | Spouge |
| 3,245,642 A | 4/1966 | Dicke |
| 3,255,568 A | 6/1966 | Martin et al. |
| 3,260,091 A | 7/1966 | Shaw, Jr. |
| 3,265,822 A | 8/1966 | Moulten |
| 3,266,487 A | 8/1966 | Watkins et al. |
| 3,273,447 A | 9/1966 | Frank |
| 3,283,352 A | 11/1966 | Hu |
| 3,290,919 A | 12/1966 | Malinak et al. |
| 3,292,493 A | 12/1966 | Franklin |
| 3,292,888 A | 12/1966 | Fischer |
| 3,294,988 A | 12/1966 | Packard |
| 3,299,603 A | 1/1967 | Shaw |
| 3,299,882 A | 1/1967 | Masino |
| 3,301,514 A | 1/1967 | Sugaya |
| 3,302,457 A | 2/1967 | Mayes |
| 3,306,384 A | 2/1967 | Ross |
| 3,313,314 A | 4/1967 | Burke et al. |
| 3,316,935 A | 5/1967 | Kaiser et al. |
| 3,320,750 A | 5/1967 | Haise et al. |
| 3,321,035 A | 5/1967 | Tarpley |
| 3,332,788 A | 7/1967 | Barnby |
| 3,334,510 A | 8/1967 | Hallesy |
| 3,339,401 A | 9/1967 | Peters |
| 3,340,868 A | 9/1967 | Darling |
| 3,347,162 A | 10/1967 | Braznell |
| 3,350,944 A | 11/1967 | De Michele |
| 3,353,364 A | 11/1967 | Blanding et al. |
| 3,353,481 A | 11/1967 | Antonucci |
| 3,356,334 A | 12/1967 | Scaramucci |
| 3,356,510 A | 12/1967 | Barnby |
| 3,357,218 A | 12/1967 | Mitchell |
| 3,357,461 A | 12/1967 | Friendship |
| 3,359,741 A | 12/1967 | Nelson |
| 3,361,300 A | 1/1968 | Kaplan |
| 3,364,929 A | 1/1968 | Ide et al. |
| 3,365,684 A | 1/1968 | Stemke |
| 3,378,456 A | 4/1968 | Roberts |
| 3,380,445 A | 4/1968 | Frasier |
| 3,380,649 A | 4/1968 | Roberts |
| 3,385,022 A | 5/1968 | Anderson |
| 3,389,355 A | 6/1968 | Schroeder, Jr. |
| 3,393,612 A | 7/1968 | Gorgens et al. |
| 3,396,561 A | 8/1968 | Day |
| 3,399,667 A | 9/1968 | Nishimoto et al. |
| 3,400,734 A | 9/1968 | Rosenberg |
| 3,403,237 A | 9/1968 | Wysong |
| 3,409,924 A | 11/1968 | Slama |
| 3,411,347 A | 11/1968 | Wirth et al. |
| 3,417,476 A | 12/1968 | Martens |
| 3,420,325 A | 1/1969 | McAlister, et al. |
| 3,422,324 A | 1/1969 | Webb |
| 3,426,165 A | 2/1969 | Beaman |
| 3,438,391 A | 4/1969 | Yocum |
| 3,443,608 A | 5/1969 | Copping et al. |
| 3,445,335 A | 5/1969 | Gluntz |
| 3,447,281 A | 6/1969 | Bufford et al. |
| 3,450,153 A | 6/1969 | Hildebrandt et al. |
| 3,453,546 A | 7/1969 | Fryer |
| 3,453,848 A | 7/1969 | Williamson |
| 3,456,134 A | 7/1969 | Ko |
| 3,457,909 A | 7/1969 | Laird |
| 3,460,557 A | 8/1969 | Gallant |
| 3,463,338 A | 8/1969 | Schneider |
| 3,469,818 A | 9/1969 | Cowan |
| 3,470,725 A | 10/1969 | Brown et al. |
| 3,472,230 A | 10/1969 | Fogarty |
| 3,478,344 A | 11/1969 | Schwitzgebel et al. |
| 3,482,449 A | 12/1969 | Werner |
| 3,482,816 A | 12/1969 | Arnold |
| 3,487,959 A | 1/1970 | Pearne et al. |
| 3,491,842 A | 1/1970 | Delacour et al. |
| 3,492,638 A | 1/1970 | Lane |
| 3,502,829 A | 3/1970 | Reynolds |
| 3,503,116 A | 3/1970 | Strack |
| 3,504,664 A | 4/1970 | Haddad |
| 3,505,808 A | 4/1970 | Eschle |
| 3,509,754 A | 5/1970 | Massingill et al. |
| 3,512,517 A | 5/1970 | Kadish et al. |
| 3,514,919 A | 6/1970 | Ashton et al. |
| 3,516,220 A | 6/1970 | Buford et al. |
| 3,517,553 A | 6/1970 | Williams et al. |
| 3,527,226 A | 9/1970 | Hakin et al. |
| 3,529,908 A | 9/1970 | Smith |
| 3,530,449 A | 9/1970 | Anderson |
| 3,533,403 A | 10/1970 | Woodson |
| 3,534,728 A | 10/1970 | Barrows |
| 3,534,872 A | 10/1970 | Roth et al. |
| 3,535,914 A | 10/1970 | Veith et al. |
| 3,539,009 A | 11/1970 | Kudlaty |
| 3,543,744 A | 12/1970 | LePar |
| 3,545,275 A | 12/1970 | Harrison et al. |
| 3,550,583 A | 12/1970 | Chiku |
| 3,550,847 A | 12/1970 | Scott |
| 3,563,094 A | 2/1971 | Rieschel |
| 3,563,245 A | 2/1971 | McLean et al. |
| 3,566,083 A | 2/1971 | McMillin |
| 3,566,875 A | 3/1971 | Stoehr |
| 3,568,367 A | 3/1971 | Myers |
| 3,568,636 A | 3/1971 | Lockwood |
| 3,576,554 A | 4/1971 | Temps, Jr. et al. |
| 3,580,082 A | 5/1971 | Strack |
| 3,581,402 A | 6/1971 | London et al. |
| 3,581,774 A * | 6/1971 | Oeland et al. .................... 138/31 |
| 3,583,387 A | 6/1971 | Garner et al. |
| 3,587,204 A | 6/1971 | George |
| 3,590,809 A | 7/1971 | London |
| 3,590,818 A | 7/1971 | Lemole |
| 3,590,992 A | 7/1971 | Soderstrom et al. |
| 3,592,183 A | 7/1971 | Watkins et al. |
| 3,594,519 A | 7/1971 | Schmidlin |
| 3,602,885 A | 8/1971 | Grajeda |
| 3,610,016 A | 10/1971 | Bultman |
| 3,610,851 A | 10/1971 | Krupski |
| 3,611,811 A | 10/1971 | Lissau |
| 3,614,926 A | 10/1971 | Brechtel |
| 3,614,955 A | 10/1971 | Mirowski et al. |
| 3,619,742 A | 11/1971 | Rud, Jr. |
| 3,623,371 A | 11/1971 | Jullien-Davin |
| 3,624,854 A | 12/1971 | Strong |
| 3,630,242 A | 12/1971 | Schieser et al. |
| 3,631,847 A | 1/1972 | Hobbs, II |
| 3,633,881 A | 1/1972 | Yurdin |
| 3,635,061 A | 1/1972 | Rydell et al. |
| 3,635,074 A | 1/1972 | Moos et al. |
| 3,638,496 A | 2/1972 | King |
| 3,644,883 A | 2/1972 | Borman et al. |
| 3,648,687 A | 3/1972 | Ramsey, III |
| 3,651,289 A | 3/1972 | Nagashima |
| 3,651,405 A | 3/1972 | Whitney et al. |
| 3,653,671 A | 4/1972 | Shipes |
| 3,659,615 A | 5/1972 | Enger |
| 3,677,685 A | 7/1972 | Aoki et al. |
| 3,686,958 A | 8/1972 | Porter et al. |
| 3,688,568 A | 9/1972 | Karper et al. |
| 3,701,392 A | 10/1972 | Wirth et al. |
| 3,702,677 A | 11/1972 | Heffington |
| 3,703,099 A | 11/1972 | Rouse et al. |
| 3,712,138 A | 1/1973 | Alinari et al. |
| 3,713,124 A | 1/1973 | Durland et al. |
| 3,719,524 A | 3/1973 | Ripley et al. |
| 3,721,412 A | 3/1973 | Kindorf |
| 3,723,247 A | 3/1973 | Leine et al. |
| 3,724,000 A | 4/1973 | Eakman |
| 3,727,463 A | 4/1973 | Intraub |
| 3,727,616 A | 4/1973 | Lenzkes |

| | | | | | |
|---|---|---|---|---|---|
| 3,730,174 A | 5/1973 | Madison | 3,904,234 A | 9/1975 | Hill et al. |
| 3,730,560 A | 5/1973 | Abildgaard et al. | 3,908,334 A | 9/1975 | Rychiger et al. |
| 3,731,679 A | 5/1973 | Wilhelmson et al. | 3,908,461 A | 9/1975 | Turpen |
| 3,731,681 A | 5/1973 | Blackshear et al. | 3,908,721 A | 9/1975 | McGahey et al. |
| 3,732,731 A | 5/1973 | Fussell, Jr. | 3,910,087 A | 10/1975 | Jones |
| 3,735,040 A | 5/1973 | Punt et al. | 3,912,168 A | 10/1975 | Mullins et al. |
| 3,736,930 A | 6/1973 | Georgi | 3,912,304 A | 10/1975 | Abildgaard et al. |
| 3,738,356 A | 6/1973 | Workman | 3,918,286 A | 11/1975 | Whitehead |
| 3,740,921 A | 6/1973 | Meyer et al. | 3,918,291 A | 11/1975 | Pauly et al. |
| 3,746,111 A | 7/1973 | Berthiaume et al. | 3,920,965 A | 11/1975 | Sohrwardy et al. |
| 3,748,678 A | 7/1973 | Ballou | 3,921,682 A | 11/1975 | McGahey et al. |
| 3,749,098 A | 7/1973 | De Bennetot et al. | 3,922,951 A | 12/1975 | Linsinger et al. |
| 3,749,422 A | 7/1973 | Abildgaard et al. | 3,923,060 A | 12/1975 | Ellinwood, Jr. |
| 3,749,423 A | 7/1973 | Abildgaard et al. | 3,924,635 A | 12/1975 | Hakim et al. |
| 3,750,194 A | 8/1973 | Summers | 3,928,980 A | 12/1975 | Ganzinotti et al. |
| 3,757,770 A | 9/1973 | Brayshaw et al. | 3,929,175 A | 12/1975 | Coone |
| 3,759,095 A | 9/1973 | Short, Jr. et al. | 3,930,682 A | 1/1976 | Booth |
| 3,760,638 A | 9/1973 | Lawson et al. | 3,930,852 A | 1/1976 | Tanaka et al. |
| 3,763,960 A | 10/1973 | John et al. | 3,936,028 A | 2/1976 | Norton et al. |
| 3,765,142 A | 10/1973 | Lindquist et al. | 3,940,122 A | 2/1976 | Janzen et al. |
| 3,765,494 A | 10/1973 | Kielman, Jr. | 3,940,630 A | 2/1976 | Bergonz |
| 3,769,156 A | 10/1973 | Brecy et al. | 3,942,299 A | 3/1976 | Bory et al. |
| 3,769,830 A | 11/1973 | Porter et al. | 3,942,382 A | 3/1976 | Hok et al. |
| 3,774,243 A | 11/1973 | Ng et al. | 3,942,516 A | 3/1976 | Glynn et al. |
| 3,776,333 A | 12/1973 | Mathauser | 3,942,536 A | 3/1976 | Mirowski et al. |
| 3,778,051 A | 12/1973 | Allen et al. | 3,943,915 A | 3/1976 | Severson |
| 3,780,578 A | 12/1973 | Sellman et al. | 3,945,704 A | 3/1976 | Kraus et al. |
| 3,781,902 A | 12/1973 | Shim et al. | 3,946,613 A | 3/1976 | Silver |
| 3,783,585 A | 1/1974 | Hoyland et al. | 3,946,615 A | 3/1976 | Hluchan |
| 3,789,667 A | 2/1974 | Porter et al. | 3,946,724 A | 3/1976 | La Balme et al. |
| 3,796,095 A | 3/1974 | Fussell, Jr. | 3,948,141 A | 4/1976 | Shinjo et al. |
| 3,807,219 A | 4/1974 | Wallskog | 3,949,388 A | 4/1976 | Fuller |
| 3,811,429 A | 5/1974 | Fletcher et al. | 3,953,289 A | 4/1976 | Costes et al. |
| 3,815,722 A | 6/1974 | Sessoms | 3,954,271 A | 5/1976 | Tredway, Sr. |
| 3,818,765 A | 6/1974 | Eriksen et al. | 3,958,558 A | 5/1976 | Dunphy et al. |
| 3,820,400 A | 6/1974 | Russo | 3,961,425 A | 6/1976 | Swanson et al. |
| 3,820,795 A | 6/1974 | Taylor | 3,961,646 A | 6/1976 | Schon et al. |
| 3,823,610 A | 7/1974 | Fussell, Jr. | 3,962,895 A | 6/1976 | Rydell et al. |
| 3,825,065 A | 7/1974 | Lloyd et al. | 3,962,921 A | 6/1976 | Lips |
| 3,825,963 A | 7/1974 | Abildgaard et al. | 3,963,019 A | 6/1976 | Quandt |
| 3,825,964 A | 7/1974 | Groswith, III et al. | 3,964,485 A | 6/1976 | Neumeier |
| 3,828,672 A | 8/1974 | Gazzola et al. | 3,964,770 A | 6/1976 | Abildgaard et al. |
| 3,828,766 A | 8/1974 | Krasnow | 3,967,737 A | 7/1976 | Peralta et al. |
| 3,831,588 A | 8/1974 | Rindner | 3,968,473 A | 7/1976 | Patton et al. |
| 3,831,942 A | 8/1974 | Del Mar | 3,968,694 A | 7/1976 | Clark |
| 3,833,238 A | 9/1974 | Liard et a. | 3,972,320 A | 8/1976 | Kalman |
| 3,834,167 A | 9/1974 | Tabor | 3,973,753 A | 8/1976 | Wheeler |
| 3,834,739 A | 9/1974 | Abildgaard et al. | 3,973,858 A | 8/1976 | Poisson et al. |
| 3,835,523 A | 9/1974 | Stansfield et al. | 3,974,655 A | 8/1976 | Halpern et al. |
| 3,839,708 A | 10/1974 | Bredesen et al. | 3,974,865 A | 8/1976 | Fenton et al. |
| 3,842,483 A | 10/1974 | Cramer | 3,977,391 A | 8/1976 | Fleischmann |
| 3,842,668 A | 10/1974 | Lippke et al. | 3,980,871 A | 9/1976 | Lindstrom et al. |
| 3,845,664 A | 11/1974 | Perry, Jr. | 3,982,571 A | 9/1976 | Fenton et al. |
| 3,845,751 A | 11/1974 | Runstetler | 3,983,948 A | 10/1976 | Jeter |
| 3,845,757 A | 11/1974 | Weyer | 3,985,133 A | 10/1976 | Jenkins et al. |
| 3,847,434 A | 11/1974 | Weman et al. | 3,987,860 A | 10/1976 | Jabsen |
| 3,850,208 A | 11/1974 | Hamilton | 3,989,005 A | 11/1976 | Bowler, Jr. et al. |
| 3,853,117 A | 12/1974 | Murr | 3,991,749 A | 11/1976 | Zent |
| 3,854,469 A | 12/1974 | Giori et al. | 3,992,948 A | 11/1976 | D'Antonio et al. |
| 3,855,902 A | 12/1974 | Kirst et al. | 3,993,149 A | 11/1976 | Harvey |
| 3,857,399 A | 12/1974 | Zacouto et al. | 3,996,927 A | 12/1976 | Frank |
| 3,857,452 A | 12/1974 | Hartman | 3,996,962 A | 12/1976 | Sutherland |
| 3,857,745 A | 12/1974 | Grausch et al. | 4,003,141 A | 1/1977 | Le Roy |
| 3,858,581 A | 1/1975 | Kamen | 4,005,282 A | 1/1977 | Jennings |
| 3,863,622 A | 2/1975 | Buuck | 4,005,593 A | 2/1977 | Goldberg |
| 3,863,933 A | 2/1975 | Tredway | 4,006,735 A | 2/1977 | Hittman et al. |
| 3,867,950 A | 2/1975 | Fischell | 4,009,375 A | 2/1977 | White et al. |
| 3,868,008 A | 2/1975 | Brumbaugh | 4,009,591 A | 3/1977 | Hester |
| 3,868,679 A | 2/1975 | Arneson | 4,010,449 A | 3/1977 | Faggin et al. |
| 3,871,599 A | 3/1975 | Takada et al. | 4,014,319 A | 3/1977 | Favre et al. |
| 3,872,285 A | 3/1975 | Shum et al. | 4,014,321 A | 3/1977 | March |
| 3,874,388 A | 4/1975 | King et al. | 4,016,764 A | 4/1977 | Rice |
| 3,876,980 A | 4/1975 | Haemmig et al. | 4,017,329 A | 4/1977 | Larson |
| 3,878,908 A | 4/1975 | Andersson et al. | 4,018,134 A | 4/1977 | Linsinger et al. |
| 3,881,528 A | 5/1975 | Mackenzie | 4,022,190 A | 5/1977 | Meyer |
| 3,893,111 A | 7/1975 | Cotter | 4,024,864 A | 5/1977 | Davies et al. |
| 3,893,451 A | 7/1975 | Durand et al. | 4,025,912 A | 5/1977 | Rice |
| 3,895,681 A | 7/1975 | Griffin et al. | 4,026,276 A | 5/1977 | Chubbuck |
| 3,899,862 A | 8/1975 | Muys et al. | 4,027,661 A | 6/1977 | Lyon et al. |

| | | | | | | |
|---|---|---|---|---|---|---|
| 4,031,899 A | 6/1977 | Renirie et al. | | 4,167,304 A | 9/1979 | Gelbke |
| 4,036,775 A | 7/1977 | Trautvetter et al. | | 4,167,952 A | 9/1979 | Reinicke |
| 4,039,069 A | 8/1977 | Kwan et al. | | 4,168,567 A | 9/1979 | Leguy et al. |
| 4,041,954 A | 8/1977 | Ohara et al. | | 4,170,280 A | 10/1979 | Schwarz |
| 4,042,504 A | 8/1977 | Drori et al. | | 4,171,218 A | 10/1979 | Hoshino et al. |
| 4,045,345 A | 8/1977 | Drori et al. | | 4,182,344 A * | 1/1980 | Benson .................... 128/207.15 |
| 4,047,851 A | 9/1977 | Bender | | 4,183,124 A | 1/1980 | Hoffman |
| 4,048,494 A | 9/1977 | Liesting et al. | | 4,183,247 A | 1/1980 | Allen et al. |
| 4,048,879 A | 9/1977 | Cox | | 4,185,641 A | 1/1980 | Minior et al. |
| 4,049,004 A | 9/1977 | Walters | | 4,186,287 A | 1/1980 | Scott |
| 4,051,338 A | 9/1977 | Harris, III | | 4,186,749 A | 2/1980 | Fryer |
| 4,052,991 A | 10/1977 | Zacouto et al. | | 4,186,751 A | 2/1980 | Fleischmann |
| 4,055,074 A | 10/1977 | Thimons et al. | | 4,190,057 A | 2/1980 | Hill et al. |
| 4,055,175 A | 10/1977 | Clemens et al. | | 4,191,004 A | 3/1980 | Gmuer et al. |
| 4,056,854 A | 11/1977 | Boretos et al. | | 4,191,187 A | 3/1980 | Wright et al. |
| 4,058,007 A | 11/1977 | Exner et al. | | 4,192,192 A | 3/1980 | Schnell |
| 4,062,351 A | 12/1977 | Hastwell et al. | | 4,193,397 A | 3/1980 | Tucker et al. |
| 4,062,354 A | 12/1977 | Taylor et al. | | 4,204,547 A | 5/1980 | Allocca |
| 4,062,360 A | 12/1977 | Bentley | | 4,206,755 A | 6/1980 | Klein et al. |
| 4,063,439 A | 12/1977 | Besson et al. | | 4,206,761 A | 6/1980 | Cosman |
| 4,064,882 A | 12/1977 | Johnson et al. | | 4,206,762 A | 6/1980 | Cosman |
| 4,070,239 A | 1/1978 | Bevilacqua | | 4,207,903 A | 6/1980 | O'Neill |
| 4,072,047 A | 2/1978 | Reismuller et al. | | 4,212,074 A | 7/1980 | Kuno et al. |
| 4,073,292 A | 2/1978 | Edelman | | 4,217,221 A | 8/1980 | Masso |
| 4,075,099 A | 2/1978 | Pelton et al. | | 4,217,588 A | 8/1980 | Freeny, Jr. |
| 4,075,602 A | 2/1978 | Clothier | | 4,220,189 A | 9/1980 | Marquez |
| 4,077,072 A | 3/1978 | Dezura et al. | | 4,221,219 A | 9/1980 | Tucker |
| 4,077,394 A | 3/1978 | McCurdy | | 4,221,523 A | 9/1980 | Eberle |
| 4,077,405 A | 3/1978 | Haerten et al. | | 4,222,377 A | 9/1980 | Burton |
| 4,077,882 A | 3/1978 | Gangemi | | 4,223,837 A | 9/1980 | Gubbiotti et al. |
| 4,078,620 A | 3/1978 | Westlake et al. | | 4,226,124 A | 10/1980 | Kersten et al. |
| 4,080,653 A | 3/1978 | Barnes, Jr. et al. | | 4,226,229 A | 10/1980 | Eckhart et al. |
| 4,084,752 A | 4/1978 | Hagiwara et al. | | 4,227,533 A | 10/1980 | Godfrey |
| 4,086,488 A | 4/1978 | Hill | | 4,231,376 A | 11/1980 | Lyon et al. |
| 4,087,568 A | 5/1978 | Fay et al. | | 4,232,682 A | 11/1980 | Veth |
| 4,088,417 A | 5/1978 | Kosmowski | | 4,237,900 A | 12/1980 | Schulman et al. |
| 4,089,329 A | 5/1978 | Couvillon, Jr. et al. | | 4,241,247 A | 12/1980 | Byrne et al. |
| 4,090,802 A | 5/1978 | Bilz et al. | | 4,241,870 A | 12/1980 | Marcus |
| 4,092,719 A | 5/1978 | Salmon et al. | | 4,245,593 A | 1/1981 | Stein |
| 4,092,925 A | 6/1978 | Fromson | | 4,246,877 A | 1/1981 | Kennedy |
| 4,096,866 A | 6/1978 | Fischell | | 4,247,850 A | 1/1981 | Marcus |
| 4,098,293 A | 7/1978 | Kramer et al. | | 4,248,238 A | 2/1981 | Joseph et al. |
| 4,103,496 A | 8/1978 | Colamussi et al. | | 4,248,241 A | 2/1981 | Tacchi |
| 4,106,370 A | 8/1978 | Kraus et al. | | 4,256,094 A | 3/1981 | Kapp et al. |
| 4,107,689 A | 8/1978 | Jellinek | | 4,256,118 A | 3/1981 | Nagel et al. |
| 4,107,995 A | 8/1978 | Ligman et al. | | 4,262,343 A | 4/1981 | Claycomb |
| 4,108,148 A | 8/1978 | Cannon, III | | 4,262,632 A | 4/1981 | Hanton et al. |
| 4,108,575 A | 8/1978 | Schal et al. | | 4,265,241 A | 5/1981 | Portner et al. |
| 4,109,148 A | 8/1978 | Jaulmes et al. | | 4,265,252 A | 5/1981 | Chubbuck et al. |
| 4,109,518 A | 8/1978 | Dooley et al. | | 4,271,018 A | 6/1981 | Drori et al. |
| 4,109,644 A | 8/1978 | Kojima | | 4,273,070 A | 6/1981 | Hoefelmayr et al. |
| 4,111,056 A | 9/1978 | Mastromatteo | | 4,274,444 A | 6/1981 | Ruyak |
| 4,111,629 A | 9/1978 | Nussbaumer et al. | | 4,275,600 A | 6/1981 | Turner et al. |
| 4,114,424 A | 9/1978 | Johnson | | 4,275,913 A | 6/1981 | Marcus |
| 4,114,606 A | 9/1978 | Seylar | | 4,278,540 A | 7/1981 | Drori et al. |
| 4,120,097 A | 10/1978 | Jeter | | 4,280,036 A | 7/1981 | Fukatsu et al. |
| 4,120,134 A | 10/1978 | Scholle | | 4,280,775 A | 7/1981 | Wood |
| 4,121,635 A | 10/1978 | Hansel | | 4,281,666 A | 8/1981 | Cosman |
| 4,123,310 A | 10/1978 | Varon et al. | | 4,281,667 A | 8/1981 | Cosman |
| 4,124,023 A | 11/1978 | Fleischmann et al. | | 4,284,073 A | 8/1981 | Krause et al. |
| 4,127,110 A | 11/1978 | Bullara | | 4,285,770 A | 8/1981 | Chi et al. |
| 4,130,169 A | 12/1978 | Denison | | 4,291,699 A | 9/1981 | Geddes et al. |
| 4,131,596 A | 12/1978 | Allen | | 4,295,963 A | 10/1981 | Drori et al. |
| 4,133,355 A | 1/1979 | Mayer | | 4,297,927 A | 11/1981 | Kuroda et al. |
| 4,133,367 A | 1/1979 | Abell | | 4,303,075 A | 12/1981 | Heilman et al. |
| 4,140,131 A | 2/1979 | Dutcher et al. | | 4,305,402 A | 12/1981 | Katims |
| 4,141,348 A | 2/1979 | Hittman | | 4,312,374 A | 1/1982 | Drori et al. |
| 4,141,349 A | 2/1979 | Ory et al. | | 4,314,480 A | 2/1982 | Becker |
| 4,143,661 A | 3/1979 | LaForge et al. | | 4,316,693 A | 2/1982 | Baxter et al. |
| 4,146,029 A | 3/1979 | Ellinwood, Jr. | | 4,325,387 A | 4/1982 | Helfer |
| 4,147,161 A | 4/1979 | Ikebe et al. | | 4,327,804 A | 5/1982 | Reed |
| 4,148,096 A | 4/1979 | Haas et al. | | 4,328,654 A | 5/1982 | Van Ginkel et al. |
| 4,149,423 A | 4/1979 | Frosch et al. | | 4,332,254 A | 6/1982 | Lundquist |
| 4,151,823 A | 5/1979 | Grosse et al. | | 4,339,831 A | 7/1982 | Johnson |
| 4,153,085 A | 5/1979 | Adams | | 4,342,218 A | 8/1982 | Fox |
| 4,156,422 A | 5/1979 | Hildebrandt et al. | | 4,342,308 A | 8/1982 | Trick |
| 4,160,448 A | 7/1979 | Jackson | | 4,346,604 A | 8/1982 | Snook et al. |
| 4,160,971 A | 7/1979 | Jones et al. | | 4,347,851 A | 9/1982 | Jundanian |
| 4,166,469 A | 9/1979 | Littleford | | 4,350,647 A | 9/1982 | de la Cruz |

| | | | | | |
|---|---|---|---|---|---|
| 4,350,970 A | 9/1982 | von Tomkewitsch et al. | 4,478,213 A | 10/1984 | Redding |
| 4,351,037 A | 9/1982 | Scherbatskoy | 4,478,538 A | 10/1984 | Kakino et al. |
| 4,351,116 A | 9/1982 | Scott, Jr. | 4,483,196 A | 11/1984 | Kurtz et al. |
| 4,356,486 A | 10/1982 | Mount | 4,484,135 A | 11/1984 | Ishihara et al. |
| 4,360,010 A | 11/1982 | Finney | 4,485,813 A | 12/1984 | Anderson et al. |
| 4,360,277 A | 11/1982 | Daniel et al. | 4,489,916 A | 12/1984 | Stevens |
| 4,361,153 A | 11/1982 | Slocum et al. | 4,492,632 A | 1/1985 | Mattson |
| 4,363,236 A | 12/1982 | Meyers | 4,494,411 A | 1/1985 | Koschke et al. |
| 4,364,276 A | 12/1982 | Shimazoe et al. | 4,494,950 A | 1/1985 | Fischell |
| 4,365,425 A | 12/1982 | Gotchel | 4,497,176 A | 2/1985 | Rubin et al. |
| 4,368,937 A | 1/1983 | Palombo et al. | 4,497,201 A | 2/1985 | Allen et al. |
| 4,369,013 A | 1/1983 | Abildgaard et al. | 4,499,394 A | 2/1985 | Koal |
| 4,373,527 A | 2/1983 | Fischell | 4,499,691 A | 2/1985 | Karazim et al. |
| 4,376,523 A | 3/1983 | Goyen et al. | 4,499,750 A | 2/1985 | Gerber et al. |
| 4,378,809 A | 4/1983 | Cosman | 4,503,678 A | 3/1985 | Wimbush et al. |
| 4,380,427 A | 4/1983 | Hehl et al. | 4,511,974 A | 4/1985 | Nakane et al. |
| 4,385,636 A | 5/1983 | Cosman | 4,513,295 A | 4/1985 | Jones et al. |
| 4,386,422 A | 5/1983 | Mumby et al. | 4,515,004 A | 5/1985 | Jaenson |
| 4,387,907 A | 6/1983 | Hiestand et al. | 4,515,750 A | 5/1985 | Pardini et al. |
| 4,392,368 A | 7/1983 | Folkesson et al. | 4,516,866 A | 5/1985 | Yamauchi et al. |
| 4,393,899 A | 7/1983 | Tsuji et al. | 4,518,637 A | 5/1985 | Takeda et al. |
| 4,393,951 A | 7/1983 | Horst-Rudolf et al. | 4,519,401 A | 5/1985 | Ko et al. |
| 4,395,232 A | 7/1983 | Koch | 4,520,443 A | 5/1985 | Yuki et al. |
| 4,395,258 A | 7/1983 | Wang et al. | 4,522,213 A | 6/1985 | Wallroth et al. |
| 4,395,916 A | 8/1983 | Martin | 4,527,568 A | 7/1985 | Rickards et al. |
| 4,398,983 A | 8/1983 | Suzuki et al. | 4,529,401 A | 7/1985 | Leslie et al. |
| 4,399,705 A | 8/1983 | Weiger et al. | 4,531,526 A | 7/1985 | Genest |
| 4,399,707 A | 8/1983 | Wamstad | 4,531,936 A | 7/1985 | Gordon |
| 4,399,809 A | 8/1983 | Baro et al. | 4,536,000 A | 8/1985 | Rohm et al. |
| 4,399,821 A | 8/1983 | Bowers | 4,537,005 A | 8/1985 | Hoyland et al. |
| 4,403,984 A | 9/1983 | Ash et al. | 4,537,129 A | 8/1985 | Heinemann et al. |
| 4,404,968 A | 9/1983 | Evans, Sr. | 4,538,616 A | 9/1985 | Rogoff |
| 4,404,974 A | 9/1983 | Titus | 4,540,404 A | 9/1985 | Wolvek |
| 4,405,318 A | 9/1983 | Whitney et al. | 4,542,461 A | 9/1985 | Eldridge et al. |
| 4,407,125 A | 10/1983 | Parsons et al. | 4,544,369 A | 10/1985 | Skakoon et al. |
| 4,407,271 A | 10/1983 | Schiff | 4,545,185 A | 10/1985 | Chikatani et al. |
| 4,407,296 A | 10/1983 | Anderson | 4,546,524 A | 10/1985 | Kreft |
| 4,407,326 A | 10/1983 | Wilhelm | 4,548,209 A | 10/1985 | Wielders et al. |
| 4,408,597 A | 10/1983 | Tenney, Jr. | 4,552,150 A | 11/1985 | Zacouto et al. |
| 4,408,615 A | 10/1983 | Grossman | 4,553,226 A | 11/1985 | Scherbatskoy |
| 4,415,071 A | 11/1983 | Butler et al. | 4,556,063 A | 12/1985 | Thompson et al. |
| 4,416,282 A | 11/1983 | Saulson et al. | 4,557,269 A | 12/1985 | Reynolds et al. |
| 4,418,899 A | 12/1983 | Zimmermann et al. | 4,557,332 A | 12/1985 | Denison et al. |
| 4,419,393 A | 12/1983 | Hanson et al. | 4,559,815 A | 12/1985 | Needham et al. |
| 4,421,505 A | 12/1983 | Schwartz | 4,560,979 A | 12/1985 | Rosskopf et al. |
| 4,424,720 A | 1/1984 | Bucchianeri | 4,561,442 A | 12/1985 | Vollmann et al. |
| 4,428,228 A | 1/1984 | Banzhaf et al. | 4,562,751 A | 1/1986 | Nason et al. |
| 4,428,365 A | 1/1984 | Hakky | 4,563,175 A | 1/1986 | LaFond |
| 4,430,899 A | 2/1984 | Wessel et al. | 4,565,116 A | 1/1986 | Hehl et al. |
| 4,431,009 A | 2/1984 | Marino, Jr. et al. | 4,566,456 A | 1/1986 | Koning et al. |
| 4,431,365 A | 2/1984 | Sturtz, Jr. | 4,569,623 A | 2/1986 | Goldmann |
| 4,432,363 A | 2/1984 | Kakegawa et al. | 4,570,351 A | 2/1986 | Szanto et al. |
| 4,435,173 A | 3/1984 | Siposs et al. | 4,571,161 A | 2/1986 | Leblanc et al. |
| 4,439,186 A | 3/1984 | Kuhl et al. | 4,571,995 A | 2/1986 | Timme |
| 4,441,491 A | 4/1984 | Evans, Sr. | 4,573,835 A | 3/1986 | Eckardt et al. |
| 4,441,501 A | 4/1984 | Parent | 4,574,792 A | 3/1986 | Trick |
| 4,444,194 A | 4/1984 | Burcham | 4,576,181 A | 3/1986 | Wallace et al. |
| 4,444,498 A | 4/1984 | Heinemann | 4,576,183 A | 3/1986 | Plicchi et al. |
| 4,445,385 A | 5/1984 | Endo | 4,577,512 A | 3/1986 | Lowenheck et al. |
| 4,446,711 A | 5/1984 | Valente | 4,581,018 A | 4/1986 | Jassawalla et al. |
| 4,447,224 A | 5/1984 | DeCant, Jr. et al. | 4,581,915 A | 4/1986 | Haulsee et al. |
| 4,449,493 A | 5/1984 | Kopec et al. | 4,587,840 A | 5/1986 | Dobler et al. |
| 4,450,811 A | 5/1984 | Ichikawa et al. | 4,589,805 A | 5/1986 | Duffner et al. |
| 4,451,033 A | 5/1984 | Nestegard | 4,592,339 A | 6/1986 | Kuzmak et al. |
| 4,453,537 A | 6/1984 | Spitzer | 4,592,340 A | 6/1986 | Boyles |
| 4,453,578 A | 6/1984 | Wilder | 4,593,703 A | 6/1986 | Cosman |
| 4,460,835 A | 7/1984 | Masuoka et al. | 4,595,228 A | 6/1986 | Chu |
| 4,464,170 A | 8/1984 | Clemens et al. | 4,596,563 A | 6/1986 | Pande |
| 4,465,015 A | 8/1984 | Osta et al. | 4,599,943 A | 7/1986 | Kobler et al. |
| 4,465,474 A | 8/1984 | Mardorf et al. | 4,600,855 A | 7/1986 | Strachan et al. |
| 4,466,290 A | 8/1984 | Frick | 4,602,541 A | 7/1986 | Benzinger et al. |
| 4,468,172 A | 8/1984 | Dixon et al. | 4,604,089 A | 8/1986 | Santangelo et al. |
| 4,468,762 A | 8/1984 | Jurgens et al. | 4,605,354 A | 8/1986 | Daly |
| 4,469,365 A | 9/1984 | Marcus et al. | 4,606,419 A | 8/1986 | Perini |
| 4,471,182 A | 9/1984 | Wielgos et al. | 4,606,478 A | 8/1986 | Hack et al. |
| 4,471,786 A | 9/1984 | Inagaki et al. | 4,610,256 A | 9/1986 | Wallace |
| 4,473,067 A | 9/1984 | Schiff | 4,614,137 A | 9/1986 | Jones |
| 4,473,078 A | 9/1984 | Angel | 4,617,016 A | 10/1986 | Blomberg et al. |
| 4,476,721 A | 10/1984 | Hochreuther et al. | 4,618,861 A | 10/1986 | Gettens et al. |

| | | | | | |
|---|---|---|---|---|---|
| 4,620,807 A | 11/1986 | Polit | 4,781,192 A | 11/1988 | Demer |
| 4,621,331 A | 11/1986 | Iwata et al. | 4,782,826 A | 11/1988 | Fogarty |
| 4,622,871 A | 11/1986 | Van Sickle et al. | 4,783,106 A | 11/1988 | Nutter |
| 4,626,462 A | 12/1986 | Kober et al. | 4,788,847 A | 12/1988 | Sterghos |
| 4,633,304 A | 12/1986 | Nagasaki et al. | 4,791,318 A | 12/1988 | Lewis et al. |
| 4,633,878 A | 1/1987 | Bombardieri et al. | 4,794,803 A | 1/1989 | Osterhout et al. |
| 4,635,182 A | 1/1987 | Hintz | 4,796,641 A | 1/1989 | Mills et al. |
| 4,637,736 A | 1/1987 | Andeen et al. | 4,798,211 A | 1/1989 | Goor et al. |
| 4,638,665 A | 1/1987 | Benson et al. | 4,798,227 A | 1/1989 | Goodwin |
| 4,644,246 A | 2/1987 | Knapen et al. | 4,799,491 A | 1/1989 | Eckerle |
| 4,646,553 A | 3/1987 | Tufte et al. | 4,799,625 A | 1/1989 | Weaver, Jr. et al. |
| 4,648,363 A | 3/1987 | Kronich | 4,802,488 A | 2/1989 | Eckerle |
| 4,648,406 A | 3/1987 | Miller | 4,803,987 A | 2/1989 | Calfee et al. |
| 4,658,358 A | 4/1987 | Leach et al. | 4,804,368 A | 2/1989 | Skakoon et al. |
| 4,658,760 A | 4/1987 | Zebuhr | 4,807,321 A | 2/1989 | Grasselli et al. |
| 4,660,568 A | 4/1987 | Cosman | 4,808,167 A | 2/1989 | Mann et al. |
| 4,665,511 A | 5/1987 | Rodney et al. | 4,812,823 A | 3/1989 | Dickerson |
| 4,665,896 A | 5/1987 | LaForge et al. | 4,819,656 A | 4/1989 | Spector |
| 4,669,484 A | 6/1987 | Masters | 4,820,265 A | 4/1989 | DeSatnick et al. |
| 4,672,974 A | 6/1987 | Lee | 4,820,953 A | 4/1989 | Saubolle et al. |
| 4,674,457 A | 6/1987 | Berger et al. | 4,821,167 A | 4/1989 | Wiebe |
| 4,674,546 A | 6/1987 | Fournier et al. | 4,821,723 A | 4/1989 | Baker, Jr. et al. |
| 4,678,408 A | 7/1987 | Nason et al. | 4,823,779 A | 4/1989 | Daly et al. |
| 4,681,559 A | 7/1987 | Hooven | 4,830,006 A | 5/1989 | Haluska et al. |
| 4,683,850 A | 8/1987 | Bauder et al. | 4,832,034 A | 5/1989 | Pizziconi et al. |
| 4,685,463 A | 8/1987 | Williams | 4,833,384 A | 5/1989 | Munro et al. |
| 4,685,469 A | 8/1987 | Keller et al. | 4,834,731 A | 5/1989 | Nowak et al. |
| 4,685,903 A | 8/1987 | Cable et al. | 4,838,857 A | 6/1989 | Strowe et al. |
| 4,686,987 A | 8/1987 | Salo et al. | 4,840,068 A | 6/1989 | Mayhew, Jr. |
| 4,687,530 A | 8/1987 | Berscheid et al. | 4,840,350 A | 6/1989 | Cook et al. |
| 4,689,979 A | 9/1987 | Otsuka et al. | 4,844,002 A | 7/1989 | Yasui et al. |
| 4,691,694 A | 9/1987 | Boyd et al. | 4,846,153 A | 7/1989 | Berci |
| 4,691,710 A | 9/1987 | Dickens et al. | 4,846,191 A | 7/1989 | Brockway et al. |
| 4,693,253 A | 9/1987 | Adams | 4,846,664 A | 7/1989 | Hehl et al. |
| 4,695,237 A | 9/1987 | Inaba et al. | 4,854,328 A | 8/1989 | Pollack |
| 4,696,189 A | 9/1987 | Hochreuther et al. | 4,863,470 A | 9/1989 | Carter |
| 4,697,574 A | 10/1987 | Karcher et al. | 4,865,587 A | 9/1989 | Walling |
| 4,698,038 A | 10/1987 | Key et al. | 4,867,160 A | 9/1989 | Schaldach et al. |
| 4,700,497 A | 10/1987 | Sato et al. | 4,867,498 A | 9/1989 | Delphia et al. |
| 4,700,610 A | 10/1987 | Bauer et al. | 4,867,618 A | 9/1989 | Brohammer |
| 4,701,143 A | 10/1987 | Key et al. | 4,869,252 A | 9/1989 | Gilli |
| 4,703,756 A | 11/1987 | Gough et al. | 4,870,258 A | 9/1989 | Mochizuki et al. |
| 4,705,507 A | 11/1987 | Boyles | 4,871,351 A | 10/1989 | Feingold et al. |
| 4,706,948 A | 11/1987 | Kroecher et al. | 4,872,483 A | 10/1989 | Shah |
| 4,712,562 A | 12/1987 | Ohayon et al. | 4,872,869 A | 10/1989 | Johns |
| 4,718,425 A | 1/1988 | Tanaka et al. | 4,873,677 A | 10/1989 | Sakamoto et al. |
| 4,722,348 A | 2/1988 | Ligtenberg et al. | 4,875,483 A | 10/1989 | Vollmann et al. |
| 4,724,806 A | 2/1988 | Hartwig et al. | 4,880,004 A | 11/1989 | Baker, Jr. et al. |
| 4,724,830 A | 2/1988 | Fischell | 4,882,678 A | 11/1989 | Hollis et al. |
| 4,725,826 A | 2/1988 | Hunter | 4,886,392 A | 12/1989 | Iio et al. |
| 4,728,479 A | 3/1988 | Merkovsky | 4,895,151 A | 1/1990 | Grevis et al. |
| 4,729,517 A | 3/1988 | Krokor et al. | 4,896,594 A | 1/1990 | Baur et al. |
| 4,730,188 A | 3/1988 | Milheiser | 4,898,158 A | 2/1990 | Daly et al. |
| 4,730,420 A | 3/1988 | Stratmann et al. | 4,898,578 A | 2/1990 | Rubalcaba, Jr. |
| 4,730,619 A | 3/1988 | Koning et al. | 4,899,751 A | 2/1990 | Cohen |
| 4,731,058 A | 3/1988 | Doan | 4,899,752 A | 2/1990 | Cohen |
| 4,735,205 A | 4/1988 | Chachques et al. | 4,902,277 A | 2/1990 | Mathies et al. |
| 4,738,267 A | 4/1988 | Lazorthes et al. | 4,903,701 A | 2/1990 | Moore et al. |
| 4,738,268 A | 4/1988 | Kipnis | 4,909,678 A | 3/1990 | Kakimoto |
| 4,741,345 A | 5/1988 | Matthews et al. | 4,913,147 A | 4/1990 | Fahlstrom et al. |
| 4,741,732 A | 5/1988 | Crankshaw et al. | 4,919,143 A | 4/1990 | Ayers |
| 4,743,129 A | 5/1988 | Keryhuel et al. | 4,924,872 A | 5/1990 | Frank |
| 4,745,541 A | 5/1988 | Vaniglia et al. | 4,926,903 A | 5/1990 | Kawai et al. |
| 4,746,830 A | 5/1988 | Holland | 4,932,406 A | 6/1990 | Berkovits |
| 4,750,495 A | 6/1988 | Moore et al. | 4,934,369 A | 6/1990 | Maxwell |
| 4,752,115 A | 6/1988 | Murray, Jr. et al. | 4,936,304 A | 6/1990 | Kresh et al. |
| 4,752,658 A | 6/1988 | Mack | 4,940,037 A | 7/1990 | Eckert et al. |
| 4,757,463 A | 7/1988 | Ballou et al. | 4,941,718 A | 7/1990 | Alexander, III et al. |
| 4,759,386 A | 7/1988 | Grouw, III | 4,942,004 A | 7/1990 | Catanzaro |
| 4,763,649 A | 8/1988 | Merrick | 4,944,050 A | 7/1990 | Shames et al. |
| 4,765,001 A | 8/1988 | Smith | 4,944,298 A | 7/1990 | Sholder |
| 4,767,406 A | 8/1988 | Wadham et al. | 4,944,307 A | 7/1990 | Hon et al. |
| 4,769,001 A | 9/1988 | Prince | 4,945,761 A | 8/1990 | Lessi et al. |
| 4,772,896 A | 9/1988 | Nakatsu et al. | 4,949,724 A | 8/1990 | Mahutte et al. |
| 4,773,401 A | 9/1988 | Citak et al. | 4,952,205 A | 8/1990 | Mauerer et al. |
| 4,774,950 A | 10/1988 | Cohen | 4,952,928 A | 8/1990 | Carroll et al. |
| 4,774,955 A | 10/1988 | Jones | 4,953,563 A | 9/1990 | Kaiser et al. |
| 4,777,953 A | 10/1988 | Ash et al. | 4,954,677 A | 9/1990 | Alberter et al. |
| 4,779,626 A | 10/1988 | Peel et al. | 4,958,630 A | 9/1990 | Rosenbluth et al. |

| | | | | | | |
|---|---|---|---|---|---|---|
| 4,958,645 A | 9/1990 | Cadell et al. | | 5,096,271 A | 3/1992 | Portman |
| 4,960,424 A | 10/1990 | Grooters | | 5,097,831 A | 3/1992 | Lekholm |
| 4,960,966 A | 10/1990 | Evans et al. | | 5,098,384 A | 3/1992 | Abrams |
| 4,967,585 A | 11/1990 | Grimaldo | | 5,103,832 A | 4/1992 | Jackson |
| 4,967,761 A | 11/1990 | Nathanielsz | | 5,105,810 A | 4/1992 | Collins et al. |
| 4,970,823 A | 11/1990 | Chen et al. | | 5,107,850 A | 4/1992 | Olive |
| 4,971,251 A | 11/1990 | Dobrick et al. | | 5,112,344 A | 5/1992 | Petros et al. |
| 4,977,896 A | 12/1990 | Robinson et al. | | 5,113,859 A | 5/1992 | Funke et al. |
| 4,978,335 A | 12/1990 | Arthur, III | | 5,113,869 A | 5/1992 | Nappholz et al. |
| 4,978,338 A | 12/1990 | Melsky et al. | | 5,115,676 A | 5/1992 | Lee |
| 4,979,730 A | 12/1990 | Holbrook et al. | | 5,117,825 A | 6/1992 | Grevious |
| 4,980,671 A | 12/1990 | McCurdy | | 5,121,777 A | 6/1992 | Leininger et al. |
| 4,981,141 A | 1/1991 | Segalowitz | | 5,127,451 A | 7/1992 | Fink, Jr. et al. |
| 4,981,173 A | 1/1991 | Perkins et al. | | 5,129,394 A | 7/1992 | Mehra |
| 4,981,426 A | 1/1991 | Aoki et al. | | 5,129,806 A | 7/1992 | Hehl et al. |
| 4,987,897 A | 1/1991 | Funke et al. | | 5,131,145 A | 7/1992 | Badoureaux et al. |
| 4,988,337 A | 1/1991 | Ito et al. | | 5,131,388 A | 7/1992 | Pless et al. |
| 4,992,794 A | 2/1991 | Brouwers et al. | | 5,133,358 A | 7/1992 | Gustafson et al. |
| 4,997,556 A | 3/1991 | Yano et al. | | 5,135,488 A | 8/1992 | Foote et al. |
| 5,001,528 A | 3/1991 | Bahraman | | 5,139,484 A | 8/1992 | Hazon et al. |
| 5,003,807 A | 4/1991 | Terrell et al. | | 5,144,949 A | 9/1992 | Olson |
| 5,003,975 A | 4/1991 | Hafelfinger et al. | | 5,148,580 A | 9/1992 | Dyckow et al. |
| 5,003,976 A | 4/1991 | Alt et al. | | 5,148,695 A | 9/1992 | Ellis |
| 5,004,472 A | 4/1991 | Wallace | | 5,152,770 A | 10/1992 | Bengmark et al. |
| 5,004,873 A | 4/1991 | Schnut | | 5,152,776 A | 10/1992 | Pinchuk |
| 5,005,574 A | 4/1991 | Fearnot et al. | | 5,154,170 A | 10/1992 | Bennett et al. |
| 5,005,586 A | 4/1991 | Lahr | | 5,154,171 A | 10/1992 | Chirife et al. |
| 5,006,844 A | 4/1991 | Ohta et al. | | 5,154,693 A | 10/1992 | East et al. |
| 5,007,401 A | 4/1991 | Grohn et al. | | 5,156,972 A | 10/1992 | Issachar et al. |
| 5,007,430 A | 4/1991 | Dardik | | 5,158,078 A | 10/1992 | Bennett et al. |
| 5,007,919 A | 4/1991 | Silva et al. | | 5,163,429 A | 11/1992 | Cohen |
| 5,009,662 A | 4/1991 | Wallace et al. | | 5,167,615 A | 12/1992 | East et al. |
| 5,010,893 A | 4/1991 | Sholder | | 5,168,757 A | 12/1992 | Rabenau et al. |
| 5,012,286 A | 4/1991 | Kawano et al. | | 5,168,982 A | 12/1992 | Hakanen et al. |
| 5,012,810 A | 5/1991 | Strand et al. | | 5,171,299 A | 12/1992 | Heitzmann et al. |
| 5,013,292 A | 5/1991 | Lemay et al. | | 5,173,873 A | 12/1992 | Wu et al. |
| 5,014,040 A | 5/1991 | Weaver et al. | | 5,174,286 A | 12/1992 | Chirife et al. |
| 5,019,032 A | 5/1991 | Robertson | | 5,174,291 A | 12/1992 | Schoonen et al. |
| 5,019,041 A | 5/1991 | Robinson et al. | | 5,176,502 A | 1/1993 | Sanderson et al. |
| 5,020,845 A | 6/1991 | Falcoff et al. | | 5,178,197 A | 1/1993 | Healy |
| 5,021,046 A | 6/1991 | Wallace | | 5,181,423 A | 1/1993 | Philipps et al. |
| 5,022,395 A | 6/1991 | Russie | | 5,181,517 A | 1/1993 | Hickey |
| 5,024,965 A | 6/1991 | Chang et al. | | 5,184,132 A | 2/1993 | Baird |
| 5,026,180 A | 6/1991 | Tajima et al. | | 5,184,614 A | 2/1993 | Collins et al. |
| 5,026,360 A | 6/1991 | Johnsen et al. | | 5,184,619 A | 2/1993 | Austin |
| 5,028,918 A | 7/1991 | Giles et al. | | 5,185,535 A | 2/1993 | Farb et al. |
| 5,032,822 A | 7/1991 | Sweet | | 5,186,224 A | 2/1993 | Schirmacher et al. |
| 5,036,869 A | 8/1991 | Inahara et al. | | 5,188,106 A | 2/1993 | Nappholz et al. |
| 5,038,800 A | 8/1991 | Oba et al. | | 5,188,604 A | 2/1993 | Orth |
| 5,041,086 A | 8/1991 | Koenig et al. | | 5,192,314 A | 3/1993 | Daskalakis |
| 5,041,826 A | 8/1991 | Milheiser | | 5,195,362 A | 3/1993 | Eason |
| 5,042,503 A | 8/1991 | Torok et al. | | 5,197,322 A | 3/1993 | Indravudh |
| 5,044,770 A | 9/1991 | Haghkar | | 5,199,427 A | 4/1993 | Strickland |
| 5,046,661 A | 9/1991 | Kimura et al. | | 5,199,428 A | 4/1993 | Obel et al. |
| 5,048,060 A | 9/1991 | Arai et al. | | 5,201,753 A | 4/1993 | Lampropoulos et al. |
| 5,050,922 A | 9/1991 | Falcoff | | 5,204,670 A | 4/1993 | Stinton |
| 5,052,910 A | 10/1991 | Hehl et al. | | 5,207,429 A | 5/1993 | Walmsley et al. |
| 5,053,008 A | 10/1991 | Bajaj | | 5,209,223 A | 5/1993 | McGorry et al. |
| 5,057,078 A | 10/1991 | Foote et al. | | 5,209,732 A | 5/1993 | Lampropoulos et al. |
| 5,058,583 A | 10/1991 | Geddes et al. | | 5,211,129 A | 5/1993 | Taylor et al. |
| 5,061,239 A | 10/1991 | Shiels | | 5,211,161 A | 5/1993 | Stef et al. |
| 5,062,052 A | 10/1991 | Sparer et al. | | 5,212,476 A | 5/1993 | Maloney |
| 5,062,053 A | 10/1991 | Shirai et al. | | 5,213,331 A | 5/1993 | Avanzini |
| 5,062,559 A | 11/1991 | Falcoff | | 5,215,523 A | 6/1993 | Williams et al. |
| 5,064,974 A | 11/1991 | Vigneau et al. | | 5,218,343 A | 6/1993 | Stobbe et al. |
| 5,067,960 A | 11/1991 | Grandjean et al. | | 5,218,957 A | 6/1993 | Strickland |
| 5,068,779 A | 11/1991 | Sullivan et al. | | 5,226,429 A | 7/1993 | Kuzmak |
| 5,069,680 A | 12/1991 | Grandjean et al. | | 5,226,604 A | 7/1993 | Seiffert et al. |
| 5,077,102 A | 12/1991 | Chong | | 5,230,694 A | 7/1993 | Rosenblum |
| 5,077,870 A | 1/1992 | Melbye et al. | | 5,233,985 A | 8/1993 | Hudrlik |
| 5,078,139 A | 1/1992 | Strand et al. | | 5,235,326 A | 8/1993 | Beigel et al. |
| 5,082,006 A | 1/1992 | Jonasson et al. | | 5,244,269 A | 9/1993 | Harriehausen et al. |
| 5,083,563 A | 1/1992 | Collins et al. | | 5,244,461 A | 9/1993 | Derlien et al. |
| 5,084,699 A | 1/1992 | DeMichele | | 5,246,008 A | 9/1993 | Mueller et al. |
| 5,085,224 A | 2/1992 | Galen et al. | | 5,249,858 A | 10/1993 | Nusser |
| 5,085,258 A | 2/1992 | Fink, Jr. et al. | | 5,250,020 A | 10/1993 | Bley |
| 5,089,673 A | 2/1992 | Strzodka et al. | | 5,254,096 A | 10/1993 | Rondelet et al. |
| 5,089,979 A | 2/1992 | McEachern et al. | | 5,256,157 A | 10/1993 | Samiotes et al. |
| 5,095,309 A | 3/1992 | Troyk et al. | | 5,263,244 A | 11/1993 | Centa et al. |

| | | | | | |
|---|---|---|---|---|---|
| 5,263,981 A | 11/1993 | Polyak et al. | 5,464,435 A | 11/1995 | Neumann |
| 5,267,940 A | 12/1993 | Moulder | 5,467,627 A | 11/1995 | Smith et al. |
| 5,267,942 A | 12/1993 | Saperston | 5,474,226 A | 12/1995 | Joseph |
| 5,269,891 A | 12/1993 | Colin et al. | 5,479,818 A | 1/1996 | Walter et al. |
| 5,271,395 A | 12/1993 | Wahlstrand et al. | 5,482,049 A | 1/1996 | Addiss et al. |
| 5,274,859 A | 1/1994 | Redman et al. | 5,487,760 A | 1/1996 | Villafana |
| 5,280,789 A | 1/1994 | Potts | 5,493,738 A | 2/1996 | Sanderson et al. |
| 5,282,839 A | 2/1994 | Roline et al. | 5,494,036 A | 2/1996 | Uber, III et al. |
| 5,282,840 A | 2/1994 | Hudrlik | 5,494,193 A | 2/1996 | Kirschner et al. |
| 5,291,894 A | 3/1994 | Nagy et al. | 5,504,474 A | 4/1996 | Libman et al. |
| 5,292,219 A | 3/1994 | Merin et al. | 5,505,916 A | 4/1996 | Berry, Jr. |
| 5,295,967 A | 3/1994 | Rondelet et al. | 5,507,412 A | 4/1996 | Ebert et al. |
| 5,298,022 A | 3/1994 | Bernardi et al. | 5,507,737 A | 4/1996 | Palmskog et al. |
| 5,298,884 A | 3/1994 | Gilmore et al. | 5,507,785 A | 4/1996 | Deno |
| 5,300,093 A | 4/1994 | Koestner et al. | 5,509,888 A | 4/1996 | Miller |
| 5,300,120 A | 4/1994 | Knapp et al. | 5,509,891 A | 4/1996 | DeRidder |
| 5,304,112 A | 4/1994 | Mrklas et al. | 5,513,945 A | 5/1996 | Hartmann et al. |
| 5,305,923 A | 4/1994 | Kirschner et al. | 5,514,103 A | 5/1996 | Srisathapat et al. |
| 5,312,443 A | 5/1994 | Adams et al. | 5,518,504 A | 5/1996 | Polyak |
| 5,312,452 A | 5/1994 | Salo | 5,520,606 A | 5/1996 | Schoolman et al. |
| 5,312,453 A | 5/1994 | Shelton et al. | 5,523,740 A | 6/1996 | Burgmann et al. |
| 5,313,953 A | 5/1994 | Yomtov et al. | 5,534,018 A | 7/1996 | Wahlstrand et al. |
| 5,314,451 A | 5/1994 | Mulier | 5,535,752 A | 7/1996 | Halperin et al. |
| 5,314,457 A | 5/1994 | Jeutter et al. | 5,538,005 A | 7/1996 | Harrison et al. |
| 5,324,315 A | 6/1994 | Grevious | 5,541,857 A | 7/1996 | Walter et al. |
| 5,325,834 A | 7/1994 | Ballheimer et al. | 5,545,140 A | 8/1996 | Conero et al. |
| 5,326,249 A | 7/1994 | Weissfloch et al. | 5,545,151 A | 8/1996 | O'Connor et al. |
| 5,328,460 A | 7/1994 | Lord et al. | 5,545,186 A | 8/1996 | Olson et al. |
| 5,330,511 A | 7/1994 | Boute et al. | 5,545,214 A | 8/1996 | Stevens |
| 5,337,750 A | 8/1994 | Walloch | 5,547,470 A | 8/1996 | Johnson et al. |
| 5,341,430 A | 8/1994 | Aulia et al. | 5,551,427 A | 9/1996 | Altman |
| 5,342,401 A | 8/1994 | Spano et al. | 5,551,439 A | 9/1996 | Hickey |
| 5,342,406 A | 8/1994 | Thompson | 5,554,185 A | 9/1996 | Block et al. |
| 5,344,388 A | 9/1994 | Maxwell et al. | 5,558,644 A | 9/1996 | Boyd et al. |
| 5,347,476 A | 9/1994 | McBean, Sr. | 5,564,434 A | 10/1996 | Halperin et al. |
| 5,348,210 A | 9/1994 | Linzell et al. | 5,575,770 A | 11/1996 | Melsky et al. |
| 5,348,536 A | 9/1994 | Young et al. | 5,584,803 A | 12/1996 | Stevens et al. |
| 5,350,413 A | 9/1994 | Miller et al. | 5,586,629 A | 12/1996 | Shoberg et al. |
| 5,352,180 A | 10/1994 | Candelon et al. | 5,593,430 A | 1/1997 | Renger |
| 5,353,622 A | 10/1994 | Theener | 5,594,665 A | 1/1997 | Walter et al. |
| 5,353,800 A | 10/1994 | Pohndorf et al. | 5,596,986 A | 1/1997 | Goldfarb |
| 5,354,200 A | 10/1994 | Klein et al. | 5,597,284 A | 1/1997 | Weltlich et al. |
| 5,354,316 A | 10/1994 | Keimel | 5,610,083 A | 3/1997 | Chan et al. |
| 5,354,319 A | 10/1994 | Wyborny et al. | 5,611,768 A | 3/1997 | Tutrone, Jr. |
| 5,360,407 A | 11/1994 | Leonard et al. | 5,612,497 A | 3/1997 | Walter et al. |
| 5,365,462 A | 11/1994 | McBean, Sr. | 5,615,671 A | 4/1997 | Schoonen et al. |
| 5,365,619 A | 11/1994 | Solomon | 5,619,991 A | 4/1997 | Sloane |
| 5,365,985 A | 11/1994 | Todd et al. | 5,625,946 A | 5/1997 | Wildeson et al. |
| 5,368,040 A | 11/1994 | Carney | 5,626,623 A | 5/1997 | Kieval et al. |
| 5,370,665 A | 12/1994 | Hudrlik | 5,626,630 A | 5/1997 | Markowitz et al. |
| 5,373,852 A | 12/1994 | Harrison et al. | 5,630,836 A | 5/1997 | Prem et al. |
| 5,375,073 A | 12/1994 | McBean | 5,634,255 A | 6/1997 | Bishop et al. |
| 5,377,128 A | 12/1994 | McBean | 5,637,083 A | 6/1997 | Bertrand et al. |
| 5,378,231 A | 1/1995 | Johnson et al. | 5,643,207 A | 7/1997 | Rise |
| 5,382,232 A | 1/1995 | Hague et al. | 5,645,116 A | 7/1997 | McDonald |
| 5,383,915 A | 1/1995 | Adams | 5,650,766 A | 7/1997 | Burgmann et al. |
| 5,388,578 A | 2/1995 | Yomtov et al. | 5,673,585 A | 10/1997 | Bishop et al. |
| 5,388,586 A | 2/1995 | Lee et al. | 5,676,690 A | 10/1997 | Noren et al. |
| 5,388,831 A | 2/1995 | Quadri et al. | 5,681,285 A | 10/1997 | Ford et al. |
| 5,394,909 A | 3/1995 | Mitchell et al. | 5,686,831 A | 11/1997 | Vandervalk et al. |
| 5,402,944 A | 4/1995 | Pape et al. | 5,687,734 A | 11/1997 | Dempsey et al. |
| 5,406,957 A | 4/1995 | Tansey | 5,693,076 A | 12/1997 | Kaemmerer |
| 5,409,009 A | 4/1995 | Olson | 5,702,368 A | 12/1997 | Stevens et al. |
| 5,411,031 A | 5/1995 | Yomtov | 5,702,427 A | 12/1997 | Ecker et al. |
| 5,411,551 A | 5/1995 | Winston et al. | 5,702,431 A | 12/1997 | Wang et al. |
| 5,411,552 A | 5/1995 | Andersen et al. | 5,704,352 A | 1/1998 | Tremblay et al. |
| 5,416,372 A | 5/1995 | Ljungstroem et al. | 5,715,786 A | 2/1998 | Seiberth et al. |
| 5,417,226 A | 5/1995 | Juma | 5,715,837 A | 2/1998 | Chen |
| 5,417,717 A | 5/1995 | Salo et al. | 5,720,436 A | 2/1998 | Buschor et al. |
| 5,425,362 A | 6/1995 | Siker et al. | 5,730,101 A | 3/1998 | Aupperle et al. |
| 5,431,171 A | 7/1995 | Harrison et al. | 5,732,710 A | 3/1998 | Rabinovich et al. |
| 5,431,694 A | 7/1995 | Snaper et al. | 5,733,313 A | 3/1998 | Barreras, Sr. et al. |
| 5,433,694 A | 7/1995 | Lim et al. | 5,738,652 A | 4/1998 | Boyd et al. |
| 5,437,605 A | 8/1995 | Helmy et al. | 5,742,233 A | 4/1998 | Hoffman et al. |
| 5,443,215 A | 8/1995 | Fackler | 5,743,267 A | 4/1998 | Nikolic et al. |
| 5,447,519 A | 9/1995 | Peterson | 5,749,369 A | 5/1998 | Rabinovich et al. |
| 5,449,368 A | 9/1995 | Kuzmak | 5,749,909 A | 5/1998 | Schroeppel et al. |
| 5,456,690 A | 10/1995 | Duong-Van | 5,755,687 A | 5/1998 | Donlon |
| 5,461,390 A | 10/1995 | Hoshen | 5,755,748 A | 5/1998 | Borza et al. |

| | | | | | | |
|---|---|---|---|---|---|---|
| 5,765,568 | A | 6/1998 | Sweezer, Jr. et al. | 6,251,093 B1 | 6/2001 | Valley et al. |
| 5,769,812 | A | 6/1998 | Stevens et al. | 6,269,819 B1 | 8/2001 | Oz et al. |
| 5,771,903 | A | 6/1998 | Jakobsson | 6,277,078 B1 | 8/2001 | Porat et al. |
| 5,782,774 | A | 7/1998 | Shmulewitz | 6,292,697 B1 | 9/2001 | Roberts |
| 5,787,520 | A | 8/1998 | Dunbar | 6,309,350 B1 | 10/2001 | VanTassel et al. |
| 5,791,344 | A | 8/1998 | Schulman et al. | 6,315,769 B1 | 11/2001 | Peer et al. |
| 5,792,094 | A | 8/1998 | Stevens et al. | 6,319,208 B1 | 11/2001 | Abita et al. |
| 5,792,179 | A | 8/1998 | Sideris | 6,328,699 B1 | 12/2001 | Eigler et al. |
| 5,795,325 | A | 8/1998 | Valley et al. | 6,338,735 B1 | 1/2002 | Stevens |
| 5,796,827 | A | 8/1998 | Coppersmith et al. | 6,357,438 B1 | 3/2002 | Hansen |
| 5,800,375 | A | 9/1998 | Sweezer et al. | 6,360,122 B1 | 3/2002 | Fischell et al. |
| 5,807,265 | A | 9/1998 | Itoigawa et al. | 6,360,822 B1 | 3/2002 | Robertson et al. |
| 5,807,336 | A | 9/1998 | Russo et al. | 6,366,817 B1 | 4/2002 | Kung |
| 5,810,015 | A | 9/1998 | Flaherty | 6,379,308 B1 | 4/2002 | Brockway et al. |
| 5,810,757 | A | 9/1998 | Sweezer, Jr. et al. | 6,379,380 B1 | 4/2002 | Satz |
| 5,814,016 | A | 9/1998 | Valley et al. | 6,398,752 B1 | 6/2002 | Sweezer, Jr. et al. |
| 5,817,093 | A | 10/1998 | Williamson, IV et al. | 6,409,674 B1 | 6/2002 | Brockway et al. |
| 5,833,603 | A | 11/1998 | Kovacs et al. | 6,423,031 B1 | 7/2002 | Donlon |
| 5,836,300 | A | 11/1998 | Mault | 6,430,444 B1 | 8/2002 | Borza et al. |
| 5,836,886 | A | 11/1998 | Itoigawa et al. | 6,431,175 B1 | 8/2002 | Penner et al. |
| 5,840,081 | A | 11/1998 | Andersen et al. | 6,432,040 B1 | 8/2002 | Meah |
| 5,849,225 | A | 12/1998 | Ebina et al. | 6,443,887 B1 | 9/2002 | Derus et al. |
| 5,855,597 | A | 1/1999 | Jayaraman et al. | 6,443,893 B1 | 9/2002 | Schnakenberg et al. |
| 5,855,601 | A | 1/1999 | Bessler et al. | 6,450,173 B1 | 9/2002 | Forsell et al. |
| 5,860,938 | A | 1/1999 | Lafontaine et al. | 6,450,946 B1 | 9/2002 | Forsell et al. |
| 5,861,018 | A | 1/1999 | Feierbach | 6,453,907 B1 | 9/2002 | Forsell et al. |
| 5,863,366 | A | 1/1999 | Snow | 6,454,698 B1 | 9/2002 | Forsell et al. |
| 5,868,702 | A | 2/1999 | Stevens et al. | 6,454,699 B1 | 9/2002 | Forsell et al. |
| 5,873,837 | A | 2/1999 | Lieber et al. | 6,454,700 B1 | 9/2002 | Forsell et al. |
| 5,875,953 | A | 3/1999 | Shioya et al. | 6,454,701 B1 | 9/2002 | Forsell et al. |
| 5,879,499 | A | 3/1999 | Corvi | 6,461,292 B1 | 10/2002 | Forsell et al. |
| 5,881,919 | A | 3/1999 | Womac et al. | 6,461,293 B1 | 10/2002 | Forsell et al. |
| 5,885,238 | A | 3/1999 | Stevens et al. | 6,463,329 B1 | 10/2002 | Goedeke |
| 5,887,475 | A | 3/1999 | Muldner | 6,463,935 B1 | 10/2002 | Forsell et al. |
| 5,899,927 | A | 5/1999 | Ecker et al. | 6,464,628 B1 | 10/2002 | Forsell et al. |
| 5,916,179 | A | 6/1999 | Sharrock | 6,470,212 B1 | 10/2002 | Weijand et al. |
| 5,916,237 | A | 6/1999 | Schu | 6,470,892 B1 | 10/2002 | Forsell et al. |
| 5,935,078 | A | 8/1999 | Feierbach | 6,471,635 B1 | 10/2002 | Forsell et al. |
| 5,938,669 | A | 8/1999 | Klaiber et al. | 6,475,136 B1 | 11/2002 | Forsell et al. |
| 5,951,487 | A | 9/1999 | Brehmeier-Flick et al. | 6,475,170 B1 | 11/2002 | Doron et al. |
| 5,957,861 | A | 9/1999 | Combs et al. | 6,482,145 B1 | 11/2002 | Forsell et al. |
| 5,967,986 | A | 10/1999 | Cimochowski et al. | 6,482,171 B1 | 11/2002 | Corvi et al. |
| 5,971,934 | A | 10/1999 | Scherer et al. | 6,482,177 B1 | 11/2002 | Leinders et al. |
| 5,974,873 | A | 11/1999 | Nelson et al. | 6,486,588 B2 | 11/2002 | Doron et al. |
| 5,978,985 | A | 11/1999 | Thurman | 6,491,291 B1 * | 12/2002 | Keeney et al. ................ 267/190 |
| 5,995,874 | A | 11/1999 | Borza et al. | 6,503,189 B1 | 1/2003 | Forsell et al. |
| 6,015,386 | A | 1/2000 | Kensey et al. | 6,504,286 B1 | 1/2003 | Porat et al. |
| 6,015,387 | A | 1/2000 | Schwartz et al. | 6,531,739 B2 | 3/2003 | Cable et al. |
| 6,019,729 | A | 2/2000 | Itoigawa et al. | 6,533,719 B2 | 3/2003 | Kuyava et al. |
| 6,024,704 | A | 2/2000 | Meador et al. | 6,533,733 B1 | 3/2003 | Ericson et al. |
| 6,030,413 | A | 2/2000 | Lazarus | 6,542,350 B1 | 4/2003 | Rogers |
| 6,035,461 | A | 3/2000 | Nguyen | 6,558,321 B1 | 5/2003 | Burd et al. |
| 6,053,873 | A | 4/2000 | Govari et al. | 6,558,994 B2 | 5/2003 | Cha et al. |
| 6,056,723 | A | 5/2000 | Donlon | 6,573,563 B2 | 6/2003 | Lee et al. |
| 6,058,330 | A | 5/2000 | Borza et al. | 6,582,462 B1 | 6/2003 | Andersen et al. |
| 6,059,757 | A | 5/2000 | Macoviak et al. | 6,599,250 B2 | 7/2003 | Webb et al. |
| 6,067,474 | A | 5/2000 | Schulman et al. | 6,605,112 B1 | 8/2003 | Moll et al. |
| 6,067,991 | A | 5/2000 | Forsell et al. | 6,629,534 B1 | 10/2003 | St. Goar et al. |
| 6,076,016 | A | 6/2000 | Feierbach | 6,640,137 B2 | 10/2003 | MacDonald |
| 6,083,174 | A | 7/2000 | Brehmeier-Flick et al. | 6,641,610 B2 | 11/2003 | Wolf et al. |
| 6,090,096 | A | 7/2000 | St. Goar et al. | 6,645,143 B2 | 11/2003 | VanTassel et al. |
| 6,102,678 | A | 8/2000 | Peclat et al. | 6,673,109 B2 | 1/2004 | Cox |
| 6,102,856 | A | 8/2000 | Groff et al. | 6,678,561 B2 | 1/2004 | Forsell |
| 6,102,922 | A | 8/2000 | Jakobsson et al. | 6,682,480 B1 | 1/2004 | Habib et al. |
| 6,106,477 | A | 8/2000 | Miesel et al. | 6,682,503 B1 | 1/2004 | Fariss et al. |
| 6,106,551 | A | 8/2000 | Crossett et al. | 6,682,559 B2 | 1/2004 | Myers et al. |
| 6,110,145 | A | 8/2000 | Macoviak | 6,695,866 B1 | 2/2004 | Kuehn et al. |
| 6,113,553 | A | 9/2000 | Chubbuck | 6,709,385 B2 | 3/2004 | Forsell et al. |
| 6,131,664 | A | 10/2000 | Sonnier | 6,718,200 B2 | 4/2004 | Marmaropoulos et al. |
| 6,135,945 | A | 10/2000 | Sultan | 6,719,787 B2 | 4/2004 | Cox |
| 6,159,156 | A | 12/2000 | Van Bockel et al. | 6,719,788 B2 | 4/2004 | Cox |
| 6,162,180 | A | 12/2000 | Miesel et al. | 6,719,789 B2 | 4/2004 | Cox |
| 6,162,245 | A | 12/2000 | Jayaraman et al. | 6,731,976 B2 | 5/2004 | Penn et al. |
| 6,168,614 | B1 | 1/2001 | Andersen et al. | 6,733,525 B2 | 5/2004 | Pease et al. |
| 6,234,745 | B1 | 5/2001 | Pugh et al. | 6,736,846 B2 | 5/2004 | Cox |
| 6,240,316 | B1 | 5/2001 | Richmond et al. | 6,752,813 B2 | 6/2004 | Goldfarb et al. |
| 6,240,318 | B1 | 5/2001 | Phillips | 6,796,942 B1 | 9/2004 | Kreiner et al. |
| 6,245,102 | B1 | 6/2001 | Jayaraman | 6,822,343 B2 | 11/2004 | Estevez |
| 6,248,080 | B1 | 6/2001 | Miesel et al. | 6,851,628 B1 | 2/2005 | Garrison et al. |

| | | |
|---|---|---|
| 6,855,115 B2 | 2/2005 | Fonseca et al. |
| 6,889,772 B2 | 5/2005 | Buytaert et al. |
| 6,890,300 B2 | 5/2005 | Lloyd et al. |
| 6,896,651 B2 | 5/2005 | Gross et al. |
| 6,896,690 B1 | 5/2005 | Lambrecht et al. |
| 6,913,600 B2 | 7/2005 | Valley et al. |
| 6,915,165 B2 | 7/2005 | Forsell et al. |
| 6,926,246 B2 | 8/2005 | Ginggen et al. |
| 6,929,653 B2 | 8/2005 | Strecter |
| 6,932,792 B1 | 8/2005 | St. Goar et al. |
| 6,951,229 B2 | 10/2005 | Garrison et al. |
| 6,951,571 B1 | 10/2005 | Srivastava |
| 6,953,429 B2 | 10/2005 | Forsell et al. |
| 6,961,619 B2 | 11/2005 | Casey |
| 6,970,742 B2 | 11/2005 | Mann et al. |
| 6,979,350 B2 | 12/2005 | Moll et al. |
| 6,985,078 B2 | 1/2006 | Suzuki et al. |
| 6,989,027 B2 | 1/2006 | Allen et al. |
| 7,011,095 B2 | 3/2006 | Wolf et al. |
| 7,011,624 B2 | 3/2006 | Forsell et al. |
| 7,017,583 B2 | 3/2006 | Forsell et al. |
| 7,018,406 B2 | 3/2006 | Seguin et al. |
| 7,021,402 B2 | 4/2006 | Beato et al. |
| 7,025,727 B2 | 4/2006 | Brockway et al. |
| 7,032,611 B1 * | 4/2006 | Sheng ............................ 137/225 |
| 7,044,920 B2 | 5/2006 | Letort et al. |
| 7,060,080 B2 | 6/2006 | Bachmann et al. |
| 7,081,683 B2 | 7/2006 | Ariav et al. |
| 7,109,933 B2 | 9/2006 | Ito et al. |
| 7,131,447 B2 | 11/2006 | Sterman et al. |
| 7,131,945 B2 | 11/2006 | Fink et al. |
| 7,134,580 B2 | 11/2006 | Garrison et al. |
| 7,144,400 B2 | 12/2006 | Byrum et al. |
| 7,147,640 B2 | 12/2006 | Huebner et al. |
| 7,153,262 B2 | 12/2006 | Stivoric et al. |
| 7,187,978 B2 | 3/2007 | Malek et al. |
| 7,225,032 B2 | 5/2007 | Schmeling et al. |
| 7,257,438 B2 | 8/2007 | Kinast |
| 7,285,090 B2 | 10/2007 | Stivoric et al. |
| 2001/0011543 A1 | 8/2001 | Forsell |
| 2001/0041823 A1 | 11/2001 | Snyder et al. |
| 2002/0049394 A1 | 4/2002 | Roy et al. |
| 2002/0120200 A1 | 8/2002 | Brockway et al. |
| 2002/0138009 A1 | 9/2002 | Brockway et al. |
| 2002/0177782 A1 | 11/2002 | Penner |
| 2003/0009201 A1 | 1/2003 | Forsell |
| 2003/0030893 A1 | 2/2003 | Cornelius et al. |
| 2003/0032857 A1 | 2/2003 | Forsell |
| 2003/0037591 A1 | 2/2003 | Ashton et al. |
| 2003/0045775 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093117 A1 | 5/2003 | Saadat |
| 2003/0100929 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0125605 A1 | 7/2003 | Forsell |
| 2003/0125768 A1 | 7/2003 | Peter |
| 2003/0135089 A1 | 7/2003 | Forsell |
| 2003/0135090 A1 | 7/2003 | Forsell |
| 2003/0136417 A1 | 7/2003 | Fonseca et al. |
| 2003/0144648 A1 | 7/2003 | Forsell |
| 2003/0163079 A1 | 8/2003 | Burnett |
| 2003/0216666 A1 | 11/2003 | Ericson et al. |
| 2004/0054352 A1 | 3/2004 | Adams et al. |
| 2004/0113790 A1 | 6/2004 | Hamel et al. |
| 2004/0133092 A1 | 7/2004 | Kain |
| 2004/0147969 A1 | 7/2004 | Mann et al. |
| 2004/0172087 A1 | 9/2004 | Forsell |
| 2004/0186396 A1 | 9/2004 | Roy et al. |
| 2004/0254537 A1 | 12/2004 | Conlon et al. |
| 2005/0015014 A1 | 1/2005 | Fonseca et al. |
| 2005/0025979 A1 | 2/2005 | Sandt et al. |
| 2005/0027175 A1 | 2/2005 | Yang |
| 2005/0038328 A1 | 2/2005 | Stoehrer et al. |
| 2005/0061079 A1 | 3/2005 | Schulman |
| 2005/0102026 A1 | 5/2005 | Turner et al. |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187482 A1 | 8/2005 | O'Brien et al. |
| 2005/0187488 A1 | 8/2005 | Wolf |
| 2005/0192642 A1 | 9/2005 | Forsell |
| 2005/0240155 A1 | 10/2005 | Conlon |
| 2005/0240156 A1 | 10/2005 | Conlon |
| 2005/0250979 A1 | 11/2005 | Coe |
| 2005/0267406 A1 | 12/2005 | Hassler |
| 2005/0267500 A1 | 12/2005 | Hassler et al. |
| 2005/0272968 A1 | 12/2005 | Byrum et al. |
| 2005/0277960 A1 | 12/2005 | Hassler et al. |
| 2005/0277974 A1 | 12/2005 | Hassler et al. |
| 2005/0288604 A1 | 12/2005 | Eigler et al. |
| 2005/0288720 A1 | 12/2005 | Ross et al. |
| 2005/0288721 A1 | 12/2005 | Girouard et al. |
| 2005/0288739 A1 | 12/2005 | Hassler et al. |
| 2005/0288740 A1 | 12/2005 | Hassler et al. |
| 2005/0288741 A1 | 12/2005 | Hassler et al. |
| 2005/0288742 A1 | 12/2005 | Giordano et al. |
| 2006/0002035 A1 | 1/2006 | Gao et al. |
| 2006/0010090 A1 | 1/2006 | Brockway et al. |
| 2006/0020224 A1 | 1/2006 | Geiger |
| 2006/0020305 A1 | 1/2006 | Desai et al. |
| 2006/0035446 A1 | 2/2006 | Chang et al. |
| 2006/0047205 A1 | 3/2006 | Ludomirsky et al. |
| 2006/0049714 A1 | 3/2006 | Liu et al. |
| 2006/0058627 A1 | 3/2006 | Flaherty et al. |
| 2006/0064134 A1 | 3/2006 | Mazar et al. |
| 2006/0085051 A1 | 4/2006 | Fritsch |
| 2006/0089571 A1 | 4/2006 | Gertner |
| 2006/0094966 A1 | 5/2006 | Brockway et al. |
| 2006/0100531 A1 | 5/2006 | Moser |
| 2006/0113187 A1 | 6/2006 | Deng et al. |
| 2006/0122285 A1 | 6/2006 | Falloon et al. |
| 2006/0122863 A1 | 6/2006 | Gottesman et al. |
| 2006/0142635 A1 | 6/2006 | Forsell |
| 2006/0149124 A1 | 7/2006 | Forsell |
| 2006/0149324 A1 | 7/2006 | Mann et al. |
| 2006/0149327 A1 | 7/2006 | Hedberg et al. |
| 2006/0157701 A1 | 7/2006 | Bauer et al. |
| 2006/0161186 A1 | 7/2006 | Hassler et al. |
| 2006/0178617 A1 | 8/2006 | Adams et al. |
| 2006/0178695 A1 | 8/2006 | Decant et al. |
| 2006/0183967 A1 | 8/2006 | Lechner |
| 2006/0184206 A1 | 8/2006 | Baker et al. |
| 2006/0189887 A1 | 8/2006 | Hassler et al. |
| 2006/0189888 A1 | 8/2006 | Hassler et al. |
| 2006/0189889 A1 | 8/2006 | Gertner |
| 2006/0199997 A1 | 9/2006 | Hassler et al. |
| 2006/0211912 A1 | 9/2006 | Dlugos et al. |
| 2006/0211913 A1 | 9/2006 | Dlugos et al. |
| 2006/0211914 A1 | 9/2006 | Hassler et al. |
| 2006/0217668 A1 | 9/2006 | Schulze et al. |
| 2006/0217673 A1 | 9/2006 | Schulze et al. |
| 2006/0235310 A1 | 10/2006 | O'Brien et al. |
| 2006/0235439 A1 | 10/2006 | Molitor et al. |
| 2006/0235448 A1 | 10/2006 | Roslin et al. |
| 2006/0244914 A1 | 11/2006 | Cech et al. |
| 2006/0247682 A1 | 11/2006 | Gerber et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0247723 A1 | 11/2006 | Gerber et al. |
| 2006/0247724 A1 | 11/2006 | Gerber et al. |
| 2006/0247725 A1 | 11/2006 | Gerber et al. |
| 2006/0252982 A1 | 11/2006 | Hassler et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2007/0010790 A1 | 1/2007 | Byrum et al. |
| 2007/0027356 A1 | 2/2007 | Ortiz |
| 2007/0027493 A1 | 2/2007 | Ben-Haim et al. |
| 2007/0067206 A1 | 3/2007 | Haggerty et al. |
| 2007/0070906 A1 | 3/2007 | Thakur |
| 2007/0072452 A1 | 3/2007 | Inagaki et al. |
| 2007/0081304 A1 | 4/2007 | Takeguchi |
| 2007/0156013 A1 | 7/2007 | Birk |

| | | |
|---|---|---|
| 2007/0167672 A1 | 7/2007 | Dlugos et al. |
| 2007/0173881 A1 | 7/2007 | Birk et al. |
| 2007/0179583 A1 | 8/2007 | Goetzinger et al. |
| 2007/0208313 A1 | 9/2007 | Conlon et al. |
| 2007/0225781 A1 | 9/2007 | Saadat et al. |
| 2008/0009680 A1 | 1/2008 | Hassler |

FOREIGN PATENT DOCUMENTS

| | | |
|---|---|---|
| CA | 1275135 | 10/1990 |
| CA | 1277885 | 12/1990 |
| CA | 1317482 | 5/1993 |
| CA | 2082015 | 5/1993 |
| CA | 1327191 | 2/1994 |
| CA | 2119101 | 9/1994 |
| CA | 2305998 | 4/1999 |
| CN | 1059035 | 2/1992 |
| CN | 1119469 | 3/1996 |
| CN | 1241003 | 1/2000 |
| EA | 4581 | 6/2004 |
| EP | 125387 B1 | 11/1984 |
| EP | 417171 | 3/1991 |
| EP | 508141 | 10/1992 |
| EP | 568730 | 11/1993 |
| EP | 605302 | 7/1994 |
| EP | 660482 | 6/1995 |
| EP | 714017 | 5/1996 |
| EP | 769340 | 4/1997 |
| EP | 846475 | 6/1998 |
| EP | 848780 | 6/1998 |
| EP | 876808 | 11/1998 |
| EP | 888079 | 1/1999 |
| EP | 914059 | 5/1999 |
| EP | 981293 | 3/2000 |
| EP | 997680 | 5/2000 |
| EP | 1003021 | 5/2000 |
| EP | 1022983 | 8/2000 |
| EP | 1050265 | 11/2000 |
| EP | 1115329 | 7/2001 |
| EP | 1119314 | 8/2001 |
| EP | 1128871 | 9/2001 |
| EP | 1202674 | 5/2002 |
| EP | 1213991 | 6/2002 |
| EP | 1253877 | 11/2002 |
| EP | 1253879 | 11/2002 |
| EP | 1253880 | 11/2002 |
| EP | 1253881 | 11/2002 |
| EP | 1253883 | 11/2002 |
| EP | 1253888 | 11/2002 |
| EP | 1255511 | 11/2002 |
| EP | 1255513 | 11/2002 |
| EP | 1255514 | 11/2002 |
| EP | 1263355 | 12/2002 |
| EP | 1263357 | 12/2002 |
| EP | 1284691 | 2/2003 |
| EP | 1374758 | 1/2004 |
| EP | 1488735 | 12/2004 |
| EP | 1500411 | 1/2005 |
| EP | 1510306 | 3/2005 |
| EP | 1518514 | 3/2005 |
| EP | 1545303 | 6/2005 |
| EP | 1547549 | 6/2005 |
| EP | 1563814 | 8/2005 |
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1609440 | 12/2005 |
| EP | 1674033 | 6/2006 |
| EP | 1736123 | 12/2006 |
| EP | 1799119 | 6/2007 |
| GB | 2355937 | 5/2001 |
| WO | WO-8911244 | 11/1989 |
| WO | WO-8911701 | 11/1989 |
| WO | WO-9004368 | 5/1990 |
| WO | WO-9511057 | 4/1995 |
| WO | WO-9715351 | 5/1997 |
| WO | WO-9733513 | 9/1997 |
| WO | WO-9833554 | 8/1998 |
| WO | WO-9835610 | 8/1998 |
| WO | WO-9901063 | 1/1999 |
| WO | WO-9918850 | 4/1999 |
| WO | WO-0004945 | 2/2000 |
| WO | WO-0033738 | 6/2000 |
| WO | WO-0072899 | 12/2000 |
| WO | WO-0104487 | 1/2001 |
| WO | WO-0112075 | 2/2001 |
| WO | WO-0112076 | 2/2001 |
| WO | WO-0112077 | 2/2001 |
| WO | WO-0112078 | 2/2001 |
| WO | WO-0121066 | 3/2001 |
| WO | WO-0136014 | 5/2001 |
| WO | WO-0145485 | 6/2001 |
| WO | WO-0145486 | 6/2001 |
| WO | WO-0147431 | 7/2001 |
| WO | WO-0147432 | 7/2001 |
| WO | WO-0147433 | 7/2001 |
| WO | WO-0147434 | 7/2001 |
| WO | WO-0147435 | 7/2001 |
| WO | WO-0147440 | 7/2001 |
| WO | WO-0147575 | 7/2001 |
| WO | WO-0148451 | 7/2001 |
| WO | WO-0149245 | 7/2001 |
| WO | WO-0150832 | 7/2001 |
| WO | WO-0150833 | 7/2001 |
| WO | WO-0154626 | 8/2001 |
| WO | WO-0158388 | 8/2001 |
| WO | WO-0158390 | 8/2001 |
| WO | WO-0158391 | 8/2001 |
| WO | WO-0158393 | 8/2001 |
| WO | WO-0160453 | 8/2001 |
| WO | WO-0181890 | 11/2001 |
| WO | WO-0200118 | 1/2002 |
| WO | WO-0215769 | 2/2002 |
| WO | WO-0226161 | 4/2002 |
| WO | WO-02053228 | 7/2002 |
| WO | WO-02055126 | 7/2002 |
| WO | WO-02058551 | 8/2002 |
| WO | WO-02065894 | 8/2002 |
| WO | WO-02076289 | 10/2002 |
| WO | WO-02082984 | 10/2002 |
| WO | WO-02089655 | 11/2002 |
| WO | WO-02090894 | 11/2002 |
| WO | WO-02100481 | 12/2002 |
| WO | WO-03002192 | 1/2003 |
| WO | WO-03002193 | 1/2003 |
| WO | WO-03020182 | 3/2003 |
| WO | WO-03061467 | 7/2003 |
| WO | WO-03061504 | 7/2003 |
| WO | WO-03096889 | 11/2003 |
| WO | WO-2004014456 | 2/2004 |
| WO | WO-2004019773 | 3/2004 |
| WO | WO-2004058101 | 7/2004 |
| WO | WO-2004066879 | 8/2004 |
| WO | WO-2004110263 | 12/2004 |
| WO | WO-2005000206 | 1/2005 |
| WO | WO-2005007075 | 1/2005 |
| WO | WO-2005107583 | 11/2005 |
| WO | WO-2006001851 | 1/2006 |
| WO | WO-2006035446 | 4/2006 |
| WO | WO-2006113187 | 10/2006 |
| WO | WO-2006122285 | 11/2006 |
| WO | WO-2007067206 | 6/2007 |
| WO | WO-2007070906 | 6/2007 |
| WO | WO-2007072452 | 6/2007 |
| WO | WO-2007081304 | 7/2007 |
| WO | WO-2007104356 | 9/2007 |

OTHER PUBLICATIONS

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB- C21C8790AA99&id=H0166BA51-5344-E57E-5C37-C6333EA43F61&sel=1; 1 page.

"Radiation Hardened Electronics and Radiation Technology", Honeywell product and service information from website http://www.honeywell.com/sites/portal?smap=aerospace&page=Radiation-Hardened-Electronics&theme=T4; 2 pages.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

Extended European Search Report (EP08254158) dated Apr. 24, 2009.

* cited by examiner

CONSTANT FORCE MECHANISMS FOR REGULATING RESTRICTION DEVICES

FIELD

The present invention relates to methods and devices for forming a restriction in a pathway, and in particular to constant force mechanisms and methods for controlling fluid pressure in a restriction system.

BACKGROUND

Obesity is becoming a growing concern, particularly in the United States, as the number of obese people continues to increase, and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. Gastric bands have typically comprised a fluid-filled elastomeric balloon with fixed endpoints that encircles the stomach just inferior to the esophageal-gastric junction to form a small gastric pouch above the band and a reduced stoma opening in the stomach. When fluid is infused into the balloon, the band expands against the stomach creating a food intake restriction or stoma in the stomach. To decrease this restriction, fluid is removed from the band. The effect of the band is to reduce the available stomach volume and thus the amount of food that can be consumed before becoming "full."

With each of the above-described food restriction devices, safe, effective treatment requires that the device be regularly monitored and adjusted to vary the degree of restriction applied to the stomach. With banding devices, the gastric pouch above the band will substantially increase in size following the initial implantation. Accordingly, the stoma opening in the stomach must initially be made large enough to enable the patient to receive adequate nutrition while the stomach adapts to the banding device. As the gastric pouch increases in size, the band may be adjusted to vary the stoma size. In addition, it is desirable to vary the stoma size in order to accommodate changes in the patient's body or treatment regime, or in a more urgent case, to relieve an obstruction or severe esophageal dilatation. Traditionally, adjusting a hydraulic gastric band requires a scheduled clinician visit during which a hypodermic needle and syringe are used to permeate the patient's skin and add or remove fluid from the balloon. More recently, implantable pumps have been developed which enable non-invasive adjustments of the band. An external programmer communicates with the implanted pump using telemetry to control the pump. During a scheduled visit, a physician places a hand-held portion of the programmer near the gastric implant and transmits power and command signals to the implant. The implant in turn adjusts the fluid levels in the band and transmits a response command to the programmer.

While such techniques are successful in adjusting the band pressure, there remains a need for improved techniques. Conventional hydraulic gastric banding devices exert a continuous restricting force on the stomach to reduce the size of the upper stomach and to restrict the passage of food from the upper to the lower stomach. However, side effects and complications of conventional gastric banding devices include erosion of the exterior stomach tissue resulting from the constant pressure of the band on the exterior stomach. In addition, hydraulic bands do not offer stable banding over time. Liquid within the bands diffuses slowly through the elastomer. Hydraulic bands therefore cannot guarantee the optimal configuration of the band over time. Multiple adjustments to maintain the optimal configuration of the band are required, increasing the cost and the number of medical visits. Also, adjustment of the band requires puncture of the patient's skin, resulting in discomfort for the patient and an increased risk of infection.

Accordingly, there remains a need for methods and devices for regulating a hydraulic restriction system.

SUMMARY

Methods and systems are generally provided for automatically regulating a restriction in a pathway. In one embodiment, a self-regulating restriction system is provided and includes a restriction device for forming a restriction in a pathway, and a pressure adjustment unit in communication with the restriction device and effective to maintain a substantially constant equilibrium pressure between the restriction device and the pressure adjustment unit by regulating an amount of fluid in the restriction device. The restriction device can include a fluid bladder capable of forming a restriction in a pathway. In an exemplary embodiment, an amount of restriction corresponds to an amount of fluid contained in the fluid bladder.

The pressure adjustment unit can be designed in a variety of ways, but in one exemplary embodiment the unit includes a constant force mechanism coupled to a fluid communication chamber that is in fluid communication with a restriction device. In one embodiment, the constant force mechanism is a nitinol spring. In another embodiment, the constant force mechanism can include a spring in contact with a cam surface. The spring can also include a cantilever beam and the restriction system can include a set-point adjustment mechanism that can include an adjustable block movably disposed along the cantilever beam to adjust an effective length of the cantilever beam. Adjusting an effective length of the cantilever beam allows a substantially constant pressure of the pressure adjustment unit to be adjusted.

In another embodiment, the constant force mechanism can include a constant force spring disposed in a chamber and coupled to a piston. A set-point adjustment mechanism can also be included, and in one embodiment can include an adjustable bladder coupled to the piston and configured to adjust the substantially constant pressure of the pressure adjustment unit by adjusting an amount of friction generated between the adjustable bladder and the chamber. In yet another embodiment the constant force mechanism can be a compression coil spring and the fluid communication chamber can be an expandable fluid bladder that is coupled to the compression coil spring. A set-point adjustment mechanism can also be included, and in one such embodiment can include an expandable bellows coupled to the compression coil spring and configured to adjust the substantially constant pressure by adjusting a length of the compression coil spring. Another embodiment of a constant force mechanism can include a chamber containing a saturated fluid therein and configured to maintain the substantially constant pressure, independent of a volume of the chamber. A set-point adjustment mechanism can also be included, and in one such embodiment can be configured to adjust the substantially constant pressure by changing a composition of the saturated fluid. In still another embodiment the constant force mechanism can include a chamber under vacuum force. A set-point adjustment mechanism can also be included, and in one such embodiment can be configured to adjust a substantially constant pressure by changing a pressure acting on the chamber under vacuum force.

In other aspects, the constant force mechanism can include an osmotic pump that is effective to maintain the substantially constant pressure. The osmotic pump can include an actuation chamber having an osmotic fluid disposed therein and in fluid communication with the restriction device and a semi-permeable membrane that separates the actuation chamber from a fluid chamber, such as the human body or a fluid-filled housing. In another embodiment, the osmotic pump can include a fluid chamber having fluid disposed therein, an actuation chamber having a piston disposed therein, and a semi-permeable membrane that separates the fluid chamber from the actuator chamber. In other aspects, osmotic pump can include a biodegradable plug covering at least a portion of a semi-permeable membrane and configured to disintegrate over a desired period of time.

In another aspect the restriction system can include a set-point adjustment mechanism that is configured to adjust the substantially constant pressure of the pressure adjustment unit. In one exemplary embodiment, the set-point adjustment mechanism can be a constant pressure spring disposed around an expandable bladder that is inflatable to adjust the substantially constant pressure. In another exemplary embodiment, the set-point adjustment mechanism can be a lever configured to apply a force to the pressure adjustment unit, and an adjustable fulcrum coupled to the lever and movable along the lever to adjust the force applied by the lever and thereby adjust the substantially constant pressure.

Another embodiment of a system for automatically adjusting a restriction device is also provided and generally includes a fluid reservoir, a restriction device in fluid communication with the fluid reservoir and configured to form a restriction in a pathway that corresponds to an amount of fluid contained within the restriction device, and a constant force mechanism coupled to the fluid reservoir and configured to apply a substantially constant force to the fluid reservoir to maintain a substantially constant pressure in the restriction device. The constant force mechanism can have a variety of configurations. For example, the constant force mechanism can be a constant force spring disposed in a chamber and coupled to a piston. In an exemplary embodiment, the gastric restriction device includes a fluid bladder for containing fluid therein. The system can also include a set-point adjustment unit coupled to the constant force mechanism and adapted to change the substantially constant force applied by the constant force mechanism. For example, the set-point adjustment unit can be an expandable bladder.

Methods for maintaining a restriction in a pathway are also provided. In one exemplary embodiment, a restriction device is implanted in a patient to form a restriction in a pathway such that the restriction in the pathway corresponds to an amount of fluid contained within the restriction device. The restriction device can be coupled to a pressure adjustment unit that applies a substantially constant force to fluid in the restriction device to maintain a substantially constant pressure applied by the restriction device to the pathway. The method can further include adjusting the substantially constant force of the pressure adjustment unit using a set point adjustment mechanism. In one embodiment, a flow of fluid into the restriction device can increase an amount of restriction applied by the restriction device to the pathway. Preferably, the restriction device is implanted to form a restriction in a patient's stomach.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for regulating a restriction system. In general, the methods and devices utilize a substantially constant force mechanism to maintain a substantially constant pressure of fluid in a fluid-based restriction device that is implanted to form a restriction in a pathway. With such fluid-based restriction devices, an amount of fluid in the device can correspond to an amount of restriction applied to the pathway. Thus, as changes occur, for example due to weight loss by the patient, the forces acting on the restriction device (i.e., the tissue in contact with the device) will change. As a result, the pressure in the restriction device will vary, thus affecting the amount of restriction applied to the pathway. In order to maintain the effectiveness of the restriction device it is desirable to maintain a substantially constant equilibrium pressure in the device as changes occur. In an exemplary embodiment, the pressure is maintained mechanically and non-electrically, thus eliminating the need for any electrical components that may need to be powered to operate over extended periods of time power to operate the device. Further, it can maintain a restriction in a pathway without the need to detect, sense, or read a particular parameter because the pressure adjustment unit is mechanically operable to apply a substantially constant force to the fluid contained therein in response to pressure changes to achieve a substantially constant pressure.

Figure 1A:
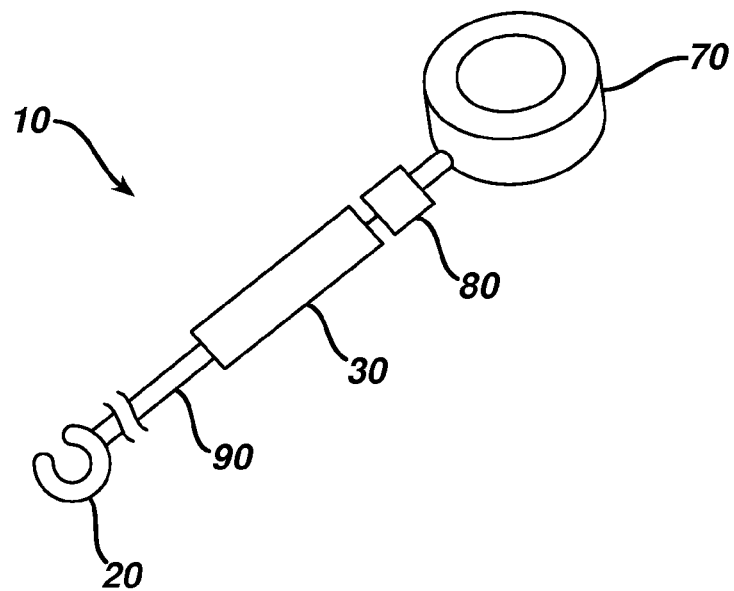
FIG. 1A is a schematic diagram illustrating one exemplary embodiment of a restriction system having a pressure adjustment unit for controlling fluid flow through the system.
Figure 1B:
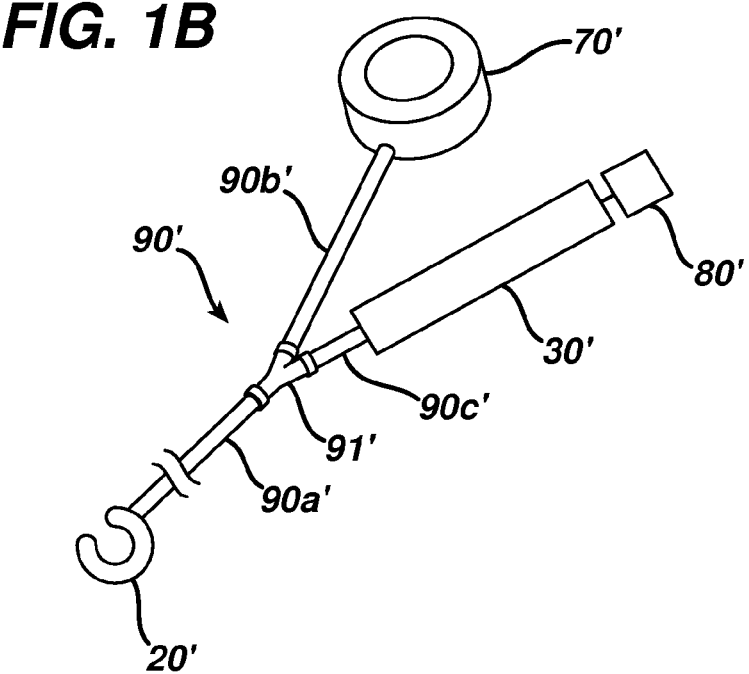
FIG. 1B is a schematic diagram illustrating another embodiment of a restriction system having a pressure adjustment unit for controlling fluid flow through the system.

While the various methods and devices disclosed herein can be used in any restriction system, by way of non-limiting example FIG. 1A illustrates one embodiment of a restriction system 10 having a restriction device 20 configured to receive fluid to form a restriction in a pathway corresponding to an amount of fluid contained therein. The system 10 also includes a pressure adjustment unit 30 that is in communication with the restriction device 20 for maintaining a substantially constant pressure of fluid in the restriction device 20. As further shown in FIG. 1A, the system 10 can also optionally include an injection port 70 for receiving fluid. The injection port 70 can be in fluid communication with the restriction device 20 and/or the pressure adjustment unit 30 for adding fluid to the restriction device 20 and/or for adjusting the substantially constant force of the pressure adjustment unit. Various techniques for allowing fluid communication between the restriction device 20, the pressure adjustment unit 30, and/or the port 70 can be used. In the illustrated embodiment, the restriction device 20, the pressure adjustment unit 30, and the port 70 are in-line with one another and are all coupled to one another by a catheter 90 extending therebetween. In another embodiment, the system can have a Y- or T-shaped configuration. For example, FIG. 1B illustrates a catheter 90' having a Y-shaped connector 91' with a first branch portion 90a' extending from one end thereof and coupled to the restriction device 20', and second and third branch portions 90b', 90c' extending from the other end thereof and coupled to the port 70' and the pressure adjustment unit 30', respectively. Such a configuration can allow easier access to fill and/or adjust the port 70' and/or the pressure adjustment unit 30'. A person skilled in the art will appreciate that the particular arrangement of components can vary. Further, the restriction system 10, 10' can also optionally include a set point mechanism 80, 80' that is configured to adjust the substantially constant force of the pressure adjustment unit 30, 30'. A person skilled in the art will appreciate that the system can have a variety of other configurations and can include various other components. For example, although the illustrated embodiments show a port being separate but in communication with the pressure adjustment unit, in other embodiments the port and pressure adjustment unit can be located in the same chamber or the port can be part of the pressure adjustment unit. The system can also optionally include sensors or other components for measuring various parameters.

Figure 1C:
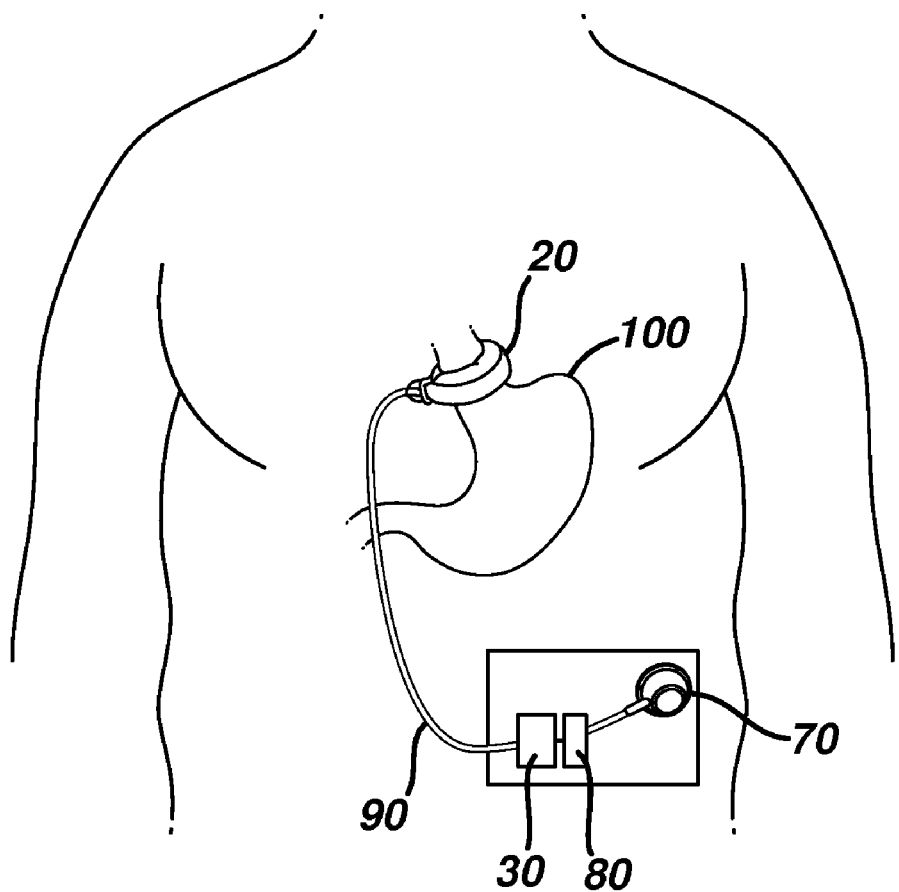
FIG. 1C is an illustration of the gastric restriction system of FIG. 1A implanted to form a restriction in a patient's stomach.
Figure 1D:
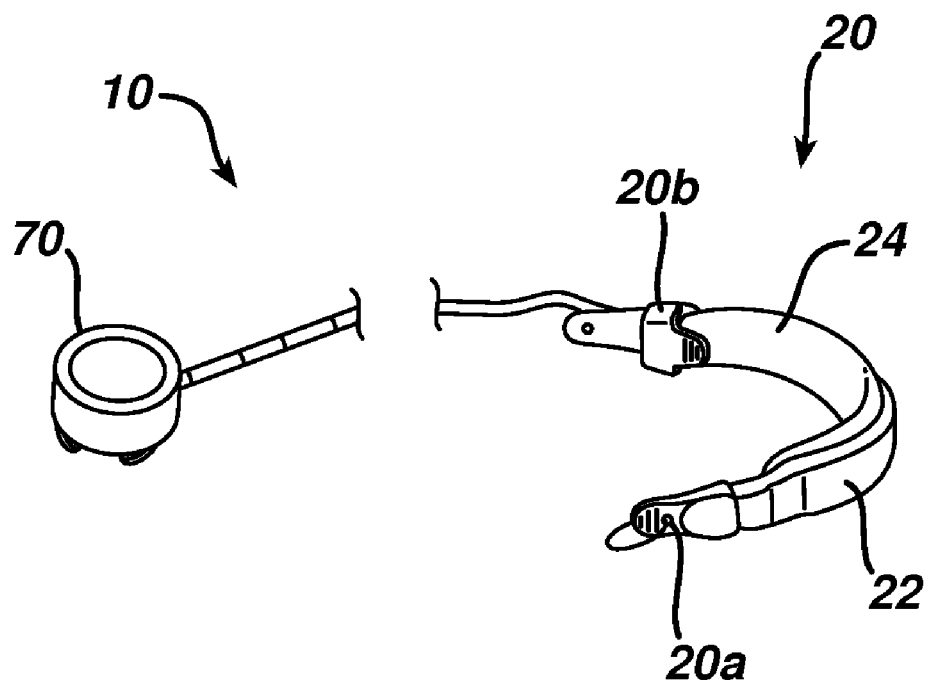
FIG. 1D is a perspective view of a gastric restriction device and port of the gastric restriction system of FIG. 1A.

FIG. 1C illustrates the restriction system 10 of FIG. 1A implanted to form a restriction in a patient's stomach 100. In the illustrated embodiment the restriction device 20 is a gastric restriction band that is positioned around the upper portion of a patient's stomach 100, however the present invention can be used with virtually any restriction device. The illustrated restriction device 20 is shown in more detail in FIG. 1D, and as shown the restriction device 20 has a generally elongate shape with a support structure 22 having first and second opposite ends 20a, 20b that can be secured to each other. Various mating techniques can be used to secure the ends 20a, 20b to one another. In the illustrated embodiment, the ends 20a, 20b are in the form of straps that mate together, with one laying on top of the other. The gastric band 20 can also include a variable volume member, such as an inflatable balloon 24, that is disposed or formed on one side of the support structure 22, and that is configured to be positioned adjacent to tissue. The balloon 24 can contain a variable amount of fluid that causes the balloon 24 to expand or contract against the outer wall of the stomach to form an adjustable stoma for controllably restricting food intake into the stomach. In use, the gastric restriction device 20 can be applied about the gastroesophageal junction of a patient. As shown in FIG. 1C, the restriction device 20 at least substantially encloses the upper portion of the stomach 100 near the junction with the esophagus. After the restriction device 20 is implanted, preferably in the deflated configuration wherein the restriction device 20 contains little or no fluid, the restriction device 20 can be inflated, e.g., using saline, to decrease the size of the stoma opening. A person skilled in the art will appreciate that various techniques, including those disclosed herein, can be used to initially inflate and/or adjust the restriction device 20.

A person skilled in the art will appreciate that the gastric band can have a variety of other configurations, moreover the various methods and devices disclosed herein have equally applicability to other types of restriction devices. For example, bands are used for the treatment of fecal incontinence, as described in U.S. Pat. No. 6,461,292 which is hereby incorporated herein by reference in its entirety. Bands can also be used to treat urinary incontinence, as described in U.S. patent application Ser. No. 2003/0105385 which is hereby incorporated herein by reference in its entirety. Bands can also be used to treat heartburn and/or acid reflux, as disclosed in U.S. Pat. No. 6,470,892 which is hereby incorporated herein by reference in its entirety. Bands can also be used to treat impotence, as described in U.S. patent application Ser. No. 2003/0114729 which is hereby incorporated herein by reference in its entirety.

As further shown in FIG. 1C, the pressure adjustment unit 30, as well as any port 70 or set-point adjustment mechanism 80 coupled thereto, can also be implanted in the patient. The particular location can vary as desired by the surgeon. Once implanted, the pressure adjustment unit 30 is configured to apply a substantially constant force to a fluid communication chamber that is in fluid communication with the restriction device. Although ideally the substantially constant force is always constant, in application constant force mechanisms attempt to achieve a constant force but are not always one hundred percent effective at maintaining that force one hundred percent of the time. Accordingly, a person skilled in the art will appreciate that the terms "constant force," "constant pressure," and "constant equilibrium" as used herein are intended to mean a substantially constant force, pressure, and equilibrium, and that minor variations will occur. In an exemplary embodiment, it is preferable that the substantially constant force remains within ten percent of the intended force. The substantially constant force that is supplied can be based on a pre-set pressure, which is a desired substantially constant pressure to be maintained in the restriction device 20 by the pressure adjustment unit 30 (thereby maintaining a substantially constant equilibrium between the restriction device 20 and the pressure adjustment unit 30). The pre-set pressure can be set prior to implantation, and preferably it is set on a patient-by-patient basis. A variety of different constant force mechanisms can be incorporated into the pressure adjustment unit 30 to supply the substantially constant force. In use, when a pressure of fluid in the restriction device 20 decreases (for example, due to patient weight loss) or increases (for example, due to patient weight gain) to a pressure that is less than or greater than the pre-set pressure controlled by the pressure adjustment unit 30, in response the pressure adjustment unit 30 will increase or decrease an amount of fluid in the restriction device 20 until the pressure of fluid in the restriction device 20 is equal to the pre-set pressure. More particularly, in an instance where a size of an area being restricted, such as a stoma of a stomach 100, decreases due to actions like weight loss, the pressure in the restriction device 20 will decrease and thus the pressure in the restriction device 20 needs to be increased to maintain enough pressure around the newly sized stoma. Because the pressure adjustment unit 30 is configured to supply a substantially constant force to a fluid communication chamber in fluid communication with the restriction device 20, when the pressure in the restriction device 20 drops below the pre-set pressure (as defined by the substantially constant force), the pressure adjustment unit 30 in response will cause fluid to flow from the fluid communication chamber into the restriction device 20 until the pressure of fluid in the restriction device 20 returns to the pre-set pressure. In other words, the pressure adjustment unit 30 is continuously attempting to achieve an equilibrium between the continuously varying forces acting on the pressure adjustment unit 30 by the fluid in the system (i.e., the fluid in the fluid communication chamber and the restriction device) and the substantially constant force applied to the fluid in the system by the constant force mechanism. The system 10 can thus control an amount of fluid added into and/or removed from the restriction device 20, thereby controlling an amount of restriction that is formed by the restriction device 20. More particularly, as fluid is added to the restriction device 20, the amount of the restriction increases, and likewise, as fluid is removed from the restriction device 20, the amount of the restriction decreases. A person skilled in the art will appreciate that the pressure adjustment unit 30 requires the use of no outside energy or forces to adjust a size of a restriction in a restriction device 20. Further, a person skilled in the art will appreciate that compensation for pressure changes in the restriction device 20 can be in real time and immediate.

Alternatively, the pressure adjustment unit 30 can be configured such that the pressure adjustment unit 30 will cause fluid to flow into the restriction device 20 only when a pressure of fluid in the restriction device 20 is less than the pre-set pressure. When a pressure of fluid in the restriction device 20 is greater than the pre-set pressure, the pressure adjustment unit 30 can take no action. This can be advantageous to allow for small variations in the pressure in the restriction device 20, for example while the patient is eating, without continuously altering the fluid pressure in the restriction device 20. An additional benefit associated with this approach is that some patients may never actually require fluid removal from the restriction device, and instead require only incremental fluid transfer into the restriction device.

Figure 2A:
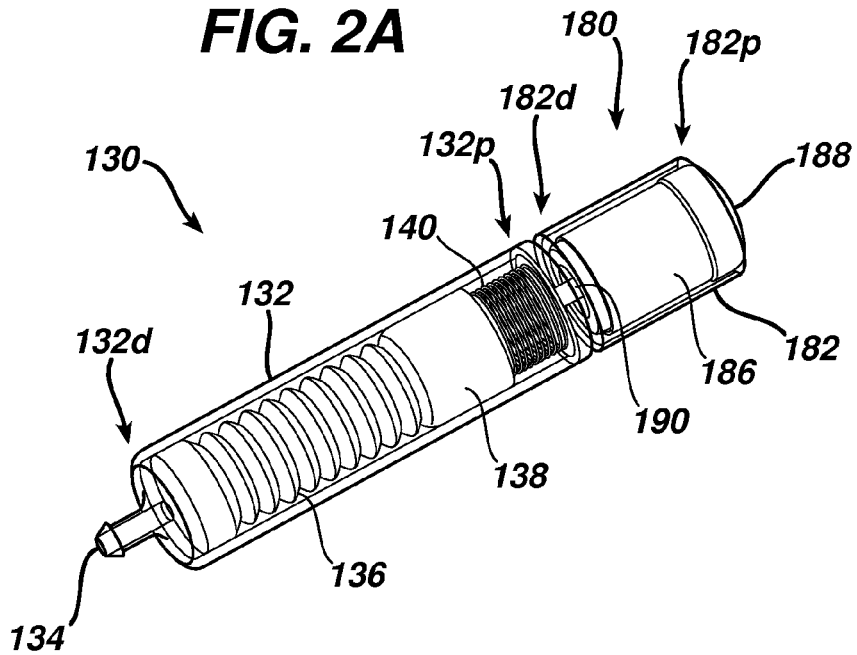
FIG. 2A is a perspective, partially transparent view of one exemplary embodiment of a pressure adjustment unit having a constant force mechanism that includes a nitinol spring coupled to an expandable bellows.
Figure 2B:
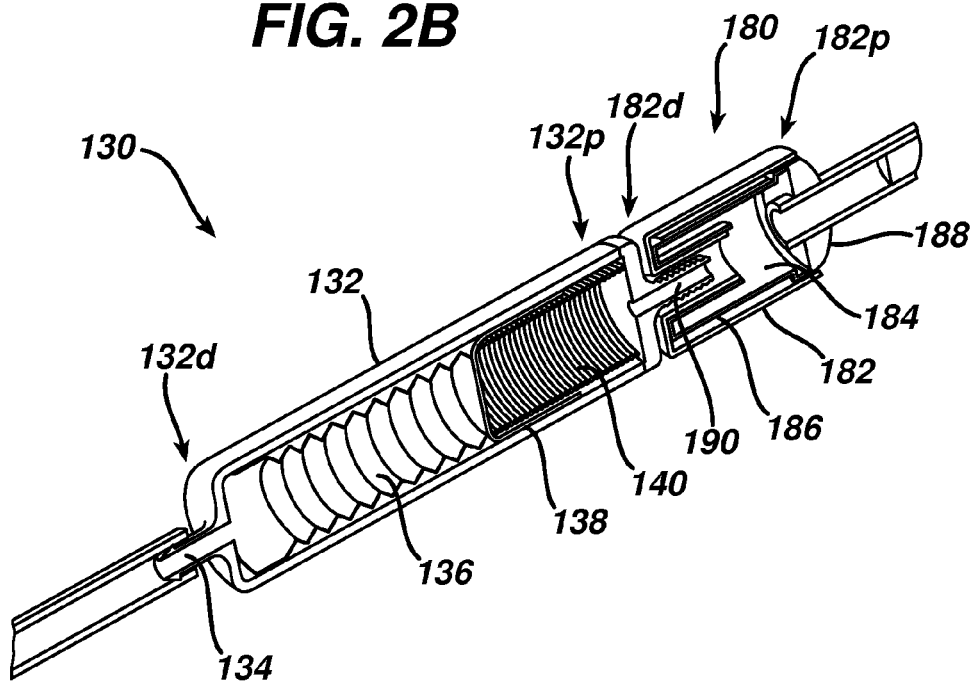
FIG. 2B is a cross-sectional view of the pressure adjustment unit of FIG. 2A.
Figure 2C:
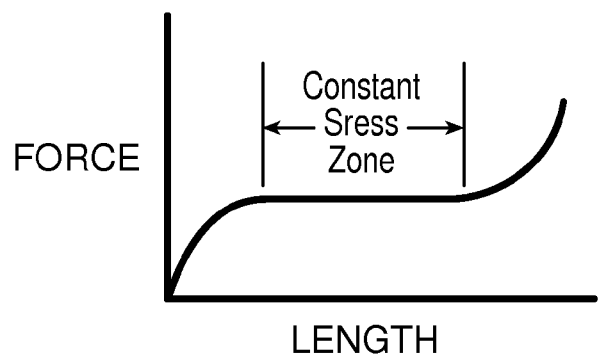
FIG. 2C is a graph illustrating the force as a function of length for a nitinol spring.

One exemplary embodiment of a pressure adjustment unit 130 is illustrated in FIGS. 2A and 2B. As shown, the pressure adjustment unit 130 generally includes a housing 132 having proximal 132p and distal ends 132d with an access port 134 formed in the distal end 132d thereof. A constant force mechanism and a fluid communication chamber are formed and/or disposed within the housing 132. In this embodiment, the fluid communication chamber is in the form of a bellows 136, and the constant force mechanism is in the form of a nitinol spring 140 that applies a constant force to a transfer mechanism, such as a piston 138, that acts on fluid in the bellows 136. The bellows 136 is disposed in the distal end 132d of the housing 132 and it can include an open distal end that is in fluid communication with the access port 134, which can be coupled to a restriction device. A proximal end of the bellows 136 can be coupled to the piston 138, which is located proximal to the bellows 136 within the housing 132. The piston 138 can be slidable in the housing 132 and configured to act on a proximal end of the bellows 136 to push fluid from inside the bellows 136 out through the access port 134. The constant force mechanism, as shown the nitinol spring 140, can be located proximal to the piston 138 and it can configured to apply a substantially constant force to the piston 138. The nitinol spring 140 is effective to provide a substantially constant force because of the properties of nitinol. In particular, as illustrated in FIG. 2C, nitinol springs typically include a constant stress zone such that as a length of the spring changes, the force applied by the spring remains constant, until a particular length is reached at either end of the stress zone, at which point the force of the spring again changes. Thus, the nitinol spring 140 can be capable of distending a significant amount while still applying approximately the same force to the piston 138.

Although FIGS. 2A and 2B shows the bellows 136, piston 138, and nitinol spring 140 as separate components, in other embodiments these components can be selectively combined or removed provided that the pressure adjustment unit 130 is still configured to maintain a substantially constant pressure in the restriction device. By way of non-limiting example, the piston 138 can be eliminated and the constant force mechanism can act directly on the bellows 136. Further, the nitinol spring 140 can be incorporated into the bellows 136 to form a single component operable to provide a substantially constant force. Additionally, a person skilled in the art will appreciate that other similar components can be substituted for some of the illustrated components. For example, the bellows 136 can be replaced by other components that are expandable and/or retractable and can be in fluid communication with the access port 134. Additionally, other constant force mechanisms, some of which are described herein, can be substituted for the nitinol spring 140 and adapted for use in the pressure adjustment unit 130.

In use, the nitinol spring 140 defines the pre-set pressure, which is a desired substantially constant pressure to be maintained in the restriction device by the pressure adjustment unit 130. When the pressure of the fluid in the restriction device drops below the pre-set pressure, the nitinol spring 140 expands to push the piston 138 distally toward the bellows 136 because the substantially constant force supplied by the nitinol spring 140 exceeds the decreased pressure of the fluid in the restriction device. Actuation of the piston 138 distally will cause the bellows 136 to be pushed distally, forcing fluid in the bellows 136 to exit through the access port 134 and to be delivered to the restriction device to raise the pressure of the fluid disposed therein. Conversely, when the pressure of the fluid in the restriction device rises above the pre-set pressure, fluid can flow from the restriction device, through the access port 134, and into the bellows 136. Flow of the fluid into the bellows 136 can cause the bellows 136 to expand or be displaced in the proximal direction, which in turn can move the piston 138 in the proximal direction to cause the nitinol spring 140 to contract. When the pressure of the fluid in the restriction device reaches the pre-set pressure, an equilibrium state of the pressure adjustment unit 130 is achieved and no fluid flows between the bellows 136 and the restriction device. In other words, when the force applied to the spring 140 by the bellows 136 (which corresponds to the pressure of fluid in the restriction device) is equal to the counter-force applied to the bellows 136 by the spring 140, the spring 138 and the bellows 136 will stop moving as the forces are equal. Any further changes to the pressure in the restriction device will result in a misbalance of the forces, causing further movement of the spring 140 and piston 138 to expand or contact the bellows 138 until an equilibrium is once again reached. A person skilled in the art will appreciate that contracting the nitinol spring 140 does not change the substantially constant force applied by the nitinol spring 140 to the piston 138, at least for a certain length, as discussed above. A person skilled in the art will also appreciate that while various embodiments herein are described as having no fluid flow, the fluid can remain in communication with the restriction device and the fluid communication chamber, e.g., the bellows 136 in the illustrated embodiment. The fluid remains in communication to allow the constant force mechanism to respond to changes in pressure, however when an equilibrium is reached the fluid simply remains stagnant and additional force is not applied to the fluid to cause movement through the system, at least until an imbalance of forces occurs. FIGS. 2A-2B also illustrate a mechanism for adjusting the pre-set pressure, which will be discussed in more detail below.

Figure 3A:
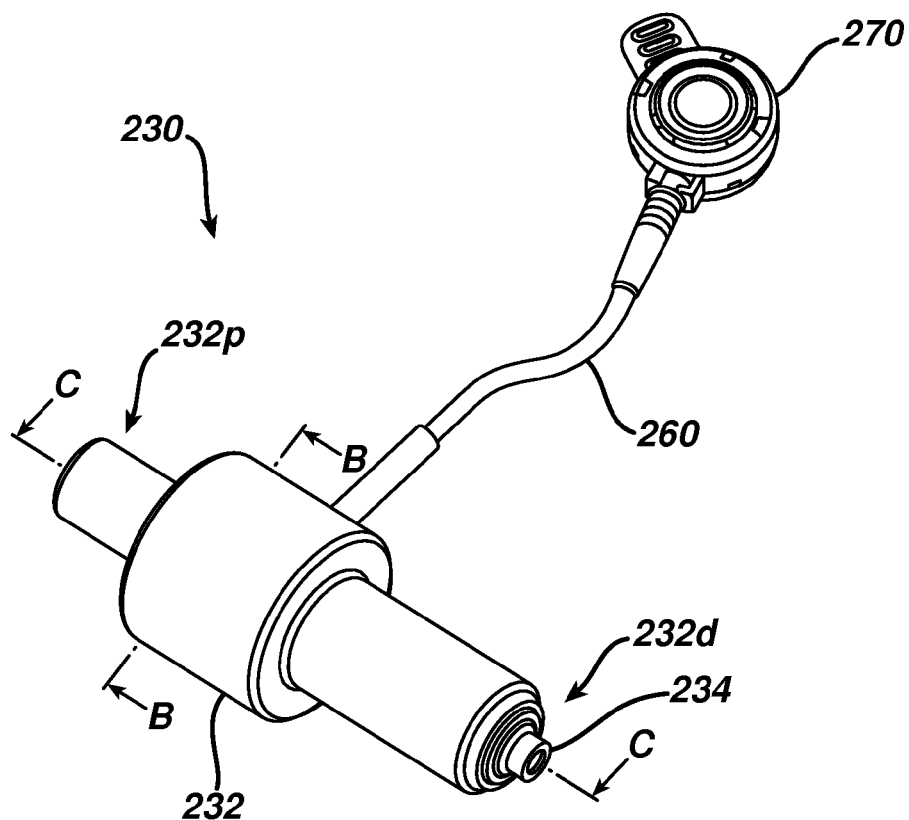
FIG. 3A is a perspective view of another embodiment of a pressure adjustment unit having a constant force mechanism that includes screw drive having a nut disposed therearound and coupled to a torsion spring.
Figure 3B:
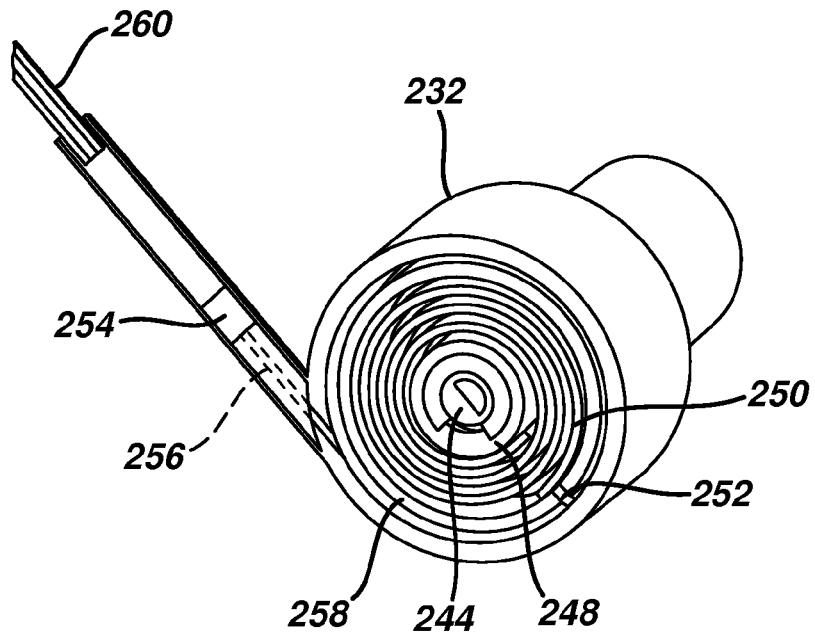
FIG. 3B is a cross-sectional view of the pressure adjustment unit of FIG. 3A taken across line B-B.
Figure 3C:
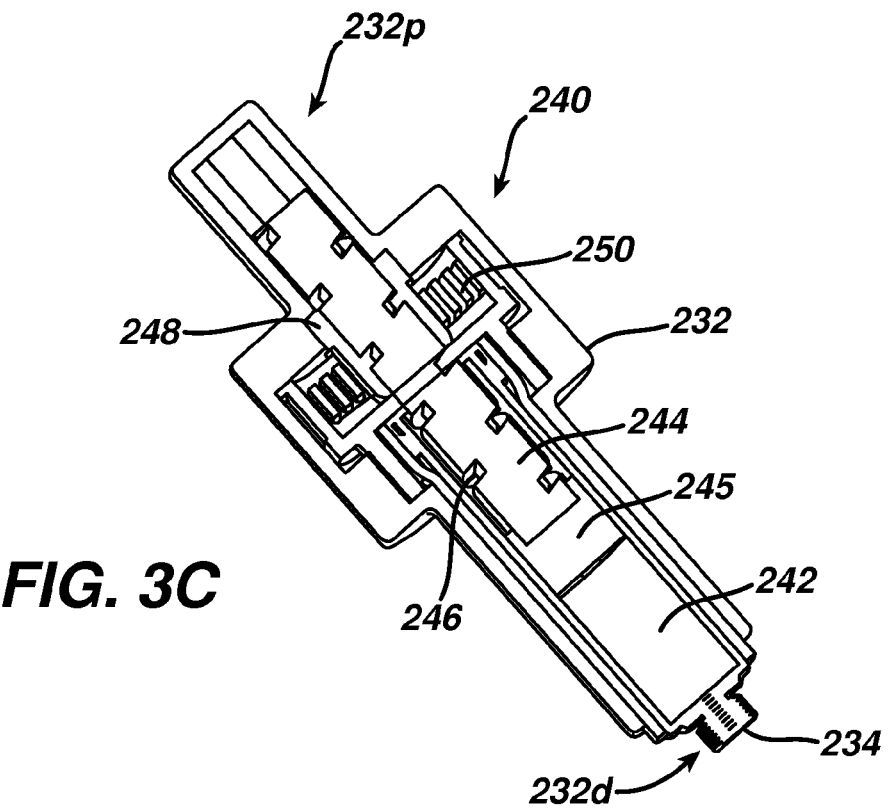
FIG. 3C is another cross-sectional view of the pressure adjustment unit of FIG. 3A taken across line C-C.

Another embodiment of a pressure adjustment unit 230 is illustrated in FIGS. 3A-3C. In general, the pressure adjustment unit 230 includes a housing 232 having proximal and distal ends 232*p*, 232*d* with an access port 234 formed in the distal end 232*d* thereof and a constant force mechanism 240 disposed therein. As illustrated, the housing 232 includes a fluid communication chamber or reservoir 242 formed a distal portion thereof and in fluid communication with a restriction device via the port 234. The constant force mechanism 240 includes a screw 244 that extends axially through the housing 232 and that includes a piston 245 coupled to a distal end thereof and configured to apply a force to the reservoir 242. The screw 244 has an inclined plane 246, such as a thread, formed therearound, and a nut 248 is threadably disposed around a mid or proximal portion of the screw 244. The nut 248 is rotatable within the housing 232, but is fixed axially. A torsion spring 250 is disposed around and coupled to the nut 248 such that the torsion spring 250 is configured to apply a force that rotates the nut 248 in a desired direction, thereby causing the screw 244 to move axially within the housing 232. Movement of the screw 244 axially within the housing 232 is effective to move the piston 245 axially within the housing 232, thereby increasing or decreasing a force applied to the fluid in the fluid reservoir 242. In a preferred embodiment, the torsion spring 250 is configured to apply a substantially constant force that turns the nut 248 in a clockwise direction which thereby applies a distally-directed force to the inclined plane 246.

In use, the torsion spring 250 defines the pre-set pressure. When the pressure of the fluid in the restriction device drops below the pre-set pressure, the torsion spring 250 causes the nut 248 to rotate in the clockwise direction, which in turn moves the screw 244 and piston 245 distally. Distal movement of the piston 245 pushes against the reservoir 242, thereby pushing the fluid out of the reservoir 242, through the access port 234, and into the restriction device to raise the pressure of the fluid disposed therein. When the pressure of the fluid in the restriction device reaches the pre-set pressure, an equilibrium state is achieved and no further pressure is applied to the fluid in the reservoir 242 and the restriction device. Conversely, when the pressure of the fluid in the restriction device rises above the pre-set pressure, fluid can flow from the restriction device, through the access port 234, and into the reservoir 242. Flow of the fluid into the reservoir 242 can cause the piston 245 to move in the proximal direction, which in turn can move the screw 244 proximally causing the nut 248 to rotate in an opposite direction, releasing tension applied to the torsion spring 250 by the nut. The piston 245 and screw 244 will continue to move proximally until the force applied to the piston 245 and screw 244 by the pressure of fluid in the restriction device is equal to the force applied to the screw 244 and piston 245 by the torsion spring 250 acting on the nut 248. Accordingly, the constant force mechanism 240 will continuously respond to changes in pressure in the fluid reservoir 242 (which corresponds to changes in pressure in the restriction device in fluid communication therewith) to thereby maintain the pre-set pressure. FIG. 3A further illustrates a port 270 that is coupled to the pressure adjustment unit 230 for adjusting the substantially constant force of the constant force mechanism, as will be discussed in more detail below.

While two different types of constant force mechanisms have been discussed thus far, there are a variety of other constant force mechanisms that can be incorporated into a pressure adjustment unit to maintain a pre-set pressure on a fluid source in fluid communication with a restriction device. Some of these constant force mechanisms are discussed in further detail below, and other constant force mechanism are known in the art and can be incorporated into a restriction system.

Figure 4A:
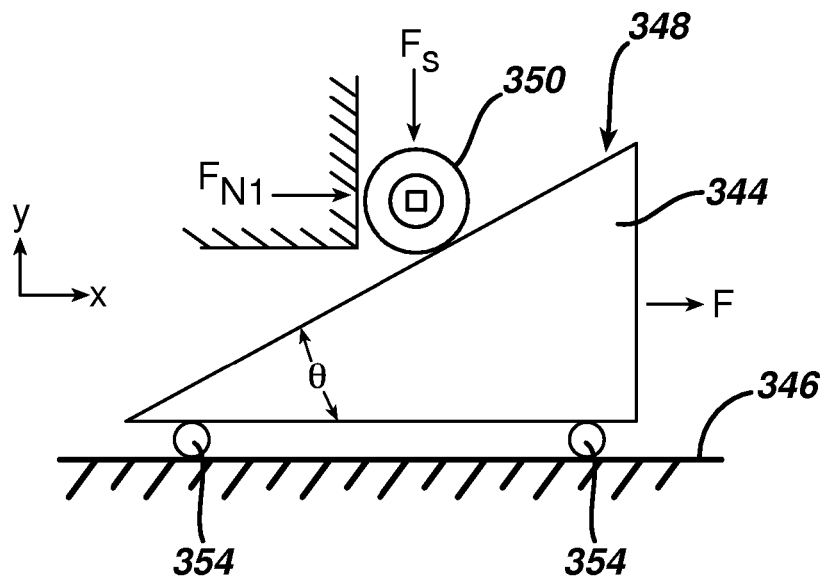
FIG. 4A is a cross-sectional view of yet another embodiment of a pressure adjustment unit having a constant force mechanism that includes a constant force spring in contact with a cam surface.

FIG. 4A illustrates another exemplary embodiment of a constant force mechanism 340 for use in a pressure adjustment unit. As shown, the constant force mechanism 340 includes a block 344 slidably disposed on a sliding surface 346. In the illustrated embodiment the block 344 includes multiple rollers 354 located on a bottom surface of the block 344 and adapted to slide along the sliding surface 346. However, the block 344 can have various other configurations that allow the block 344 to slide along the sliding surface 346. As further shown, the block 344 has a cam surface 348 formed thereon, and a spring 350 is in contact with the cam surface 348 of the block 344. While in the illustrated embodiment the cam surface 348 is substantially straight, in another embodiment the cam surface 348 can be sloped or curved. The spring 350 can have various configurations, but in an exemplary embodiment it is configured to apply a downward force $F_S$ to the cam surface 348. A normal force $F_{N1}$ can be configured to maintain the horizontal position of the downward force $F_S$, for example by applying a linear slide or other normal force-supplying object to the spring 350. The forces applied by the spring 350 to the cam surface 348 result in a substantially constant force F being applied to the block 344, as illustrated along the x-axis.

Figure 4B:
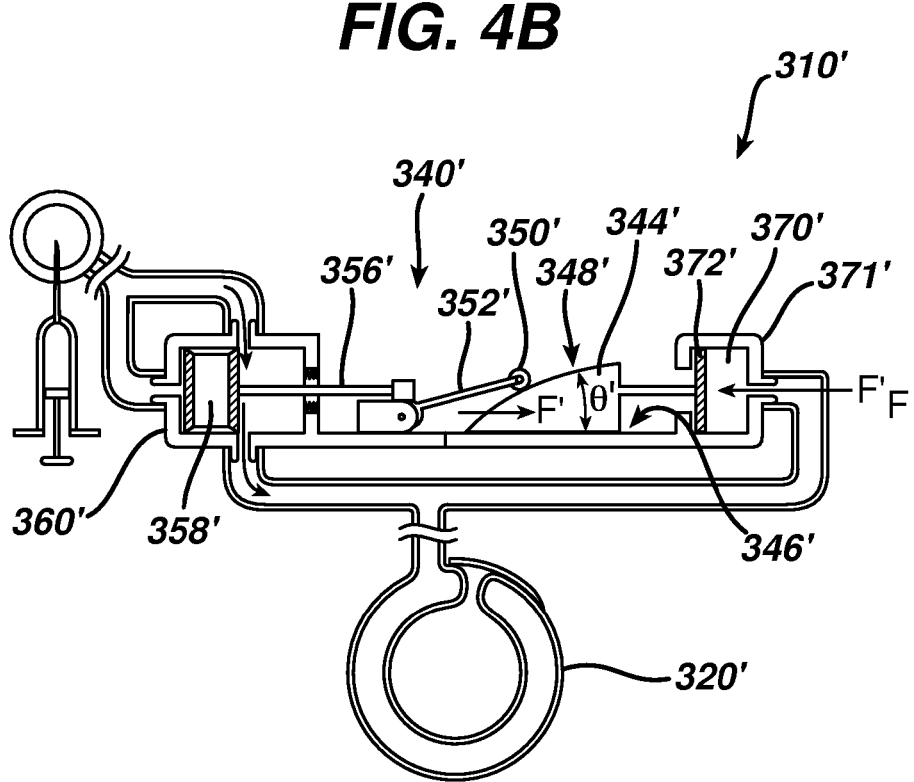
FIG. 4B is a cross-sectional view of one embodiment of a restriction system that includes a pressure adjustment unit having the constant force mechanism of FIG. 4A incorporated therein, showing the constant force mechanism in a first position.
Figure 4C:
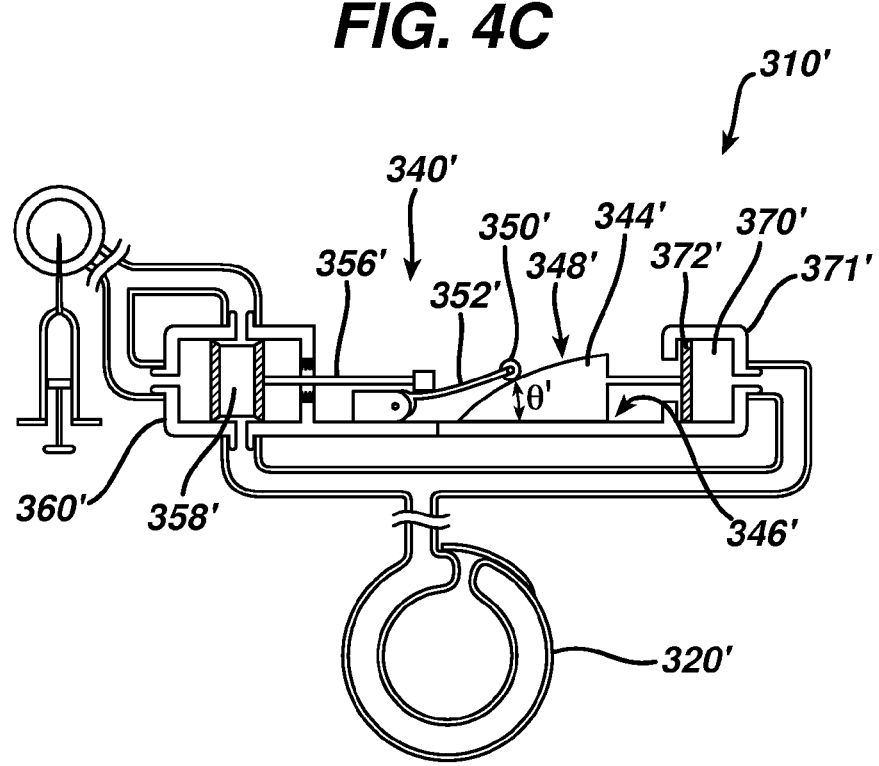
FIG. 4C is a cross-sectional view of the restriction system of FIG. 4B, showing the constant force mechanism in a second position.

A constant force mechanism like the constant force mechanism 340 illustrated in FIG. 4A can easily be incorporated into a restriction system 310', as illustrated in FIGS. 4B and 4C. In this embodiment the constant force mechanism 340' has a block 344' that slidably disposed on a sliding surface 346'. The block 344' has a cam surface 348' formed thereon and a cantilevered beam 352' is in contact with the cam surface 348' of the block 344'. While not necessary, the cantilevered beam 352' can include a bearing element 350' formed on a terminal end thereof and configured to bear against the cam surface 348' to allow movement of the cantilevered beam 352' along the cam surface 348'. In this embodiment, the block 344' is configured to slide along the sliding surface 346' without the aid of rollers, although rollers or other similar sliding devices could also be used. Movement of the block 344' can occur in response to the substantially constant force F' applied to the block 344' and in response to a force $F_F'$ applied to the block 344' by a fluid in fluid communication with a restriction device. While various techniques can be used to allow fluid communication between the constant force mechanism 340' and a restriction device, in the illustrated embodiment the system 310' includes a fluid communication chamber, such as a fluid reservoir 370' formed in a housing 371' and in fluid communication with a restriction device 320'. A piston 372' is coupled to the block 344' and is disposed within the fluid reservoir 370'. The piston 372' is configured to slidably move within the reservoir as the block 344' slidably moves along the sliding surface 3436'.

In use, the cantilevered beam 352' defines the substantially constant pressure, which corresponds to the desired pre-set pressure. When the pressure of the fluid in the restriction device 320' drops below the pre-set pressure, the substantially constant force F' applied to the block 344' by the cantilevered beam 352' will exceed the force $F_F'$ applied to the block 344' (via the piston 372') by the fluid, and thus the beam 352' will cause the block 344' to move to the right as illustrated in FIG. 4C. Movement of the block 344' to the right causes the piston 372' attached thereto to also move to the right, which in turn pushes fluid from the reservoir 370' and into the restriction device 320' to raise the pressure of the fluid disposed therein. When the pressure of the fluid in the restriction device 320' reaches the substantially constant pressure, an equilibrium is reached and no further movement occurs. Conversely, when the pressure of the fluid in the restriction device 320' rises above the pre-set pressure, fluid can flow from the restriction device 320' into the reservoir 370' and can displace the piston 372' to the left as illustrated in FIG. 4B, which in turn can move the block 344' to the left until the pressure in the restriction device 320' lowers to a pressure that is equal to the pre-set pressure FIGS. 4B-4D also illustrate a mechanism for adjusting the pre-set pressure, which will be discussed in more detail below.

Figure 4D:
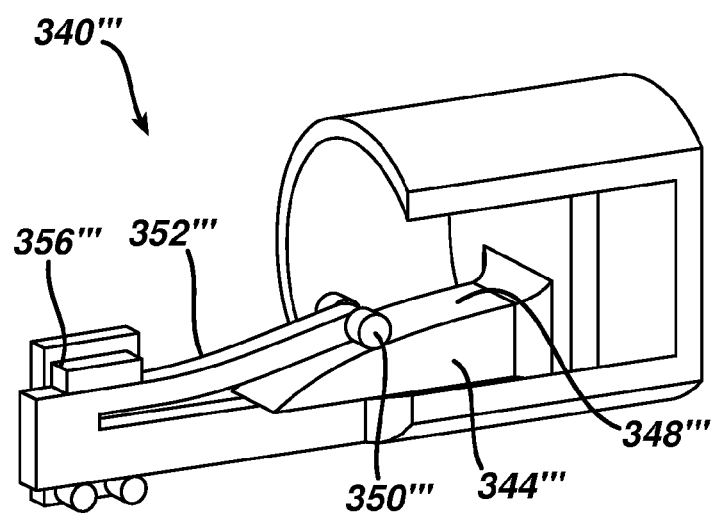
FIG. 4D is a perspective view of another embodiment of a constant force mechanism having a constant force spring in contact with a cam surface.
Figure 4E:
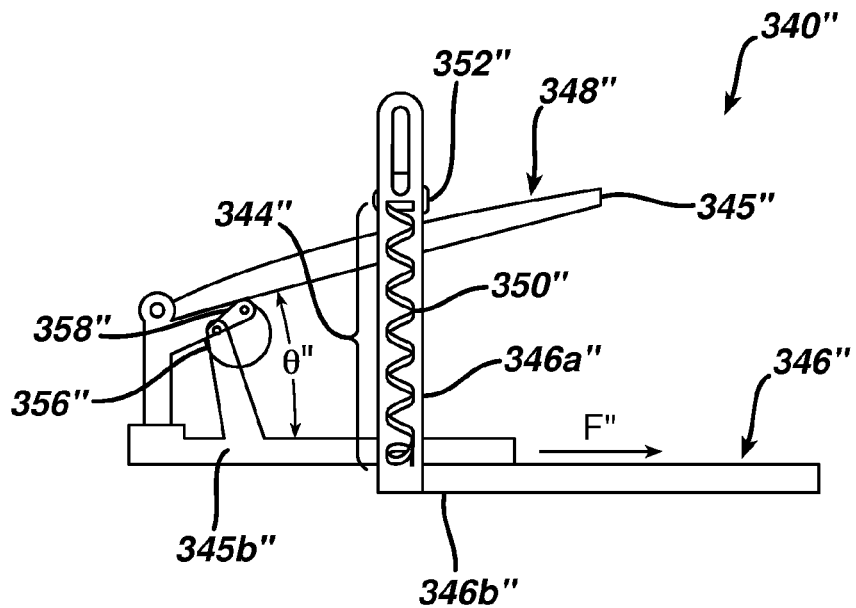
FIG. 4E is a side, partially transparent view of yet another embodiment of a constant force mechanism having a constant force spring in contact with a cam surface, showing the constant force mechanism in a first position.
Figure 4F:
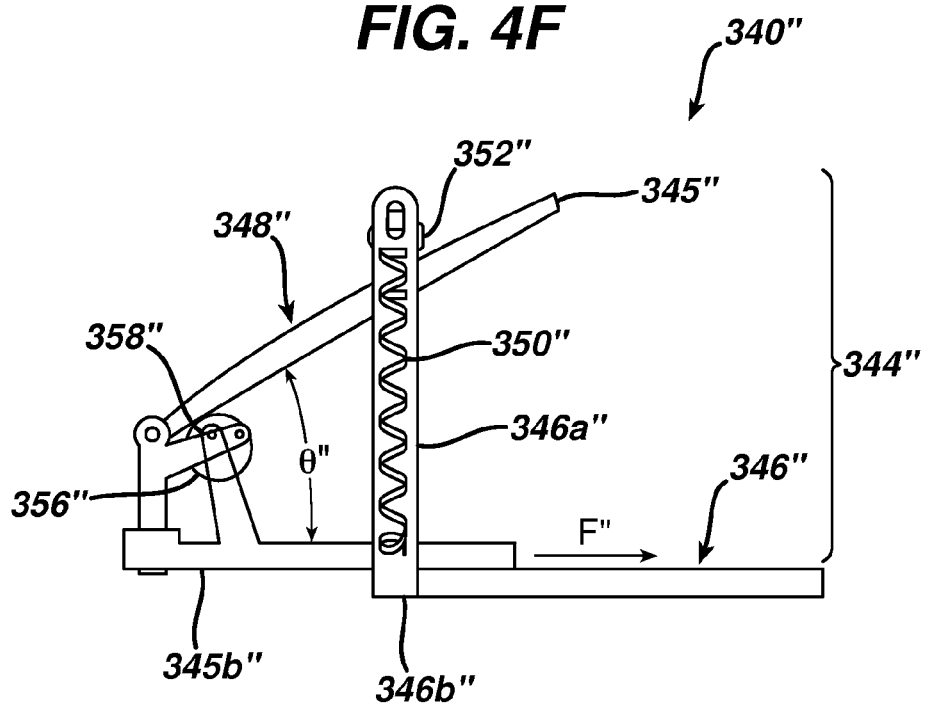
FIG. 4F is a side, partially transparent view of the constant force mechanism of FIG. 4E shown in a second position.

Another embodiment of a constant force mechanism 340" having a spring 350" in contact with a cam surface 348" is illustrated in FIGS. 4E and 4F. The constant force mechanism 340" has an adjustable cantilever device 344" slidably coupled to a sliding surface 346". The adjustable cantilever device 344" includes a cantilever beam 345" having a cam surface 348" formed thereon. The cantilevered beam 345" can be fixedly, but optionally adjustably, coupled to a base 345b". The adjustable cantilever device 344' can also include a spring 350" that is configured to apply a force to the cantilevered beam 345" to cause the beam 345" (with the base 345b" coupled thereto) to move in the right and left directions. In the illustrated embodiment, the spring 350" is extended along an arm 346a" that extends transverse to the beam 345". The spring 350" includes a first end that is fixedly coupled to a base 346b" of the arm 346a" and a second end that is mated to a bearing element 352". The bearing element 352" is movably mounted along a length of the arm 346a" and is slidably seated on the cam surface 348" of the beam 345". In use, the spring 350" applies a force to the beam 345" via the bearing element 352". This force can cause the beam 345 and the base 346b" mated to the beam 345" to slide along a sliding surface 346" on a base 346b" mated to the arm 346'a", as shown in FIGS. 4E and 4F. As the beam 345" slides, the bearing element 352" will move up and down relative to the arm 346a" due to the angled cam surface 348" and the force of the spring 350" acting on the bearing element 352". Thus, similar to the constant force mechanism 340 illustrated in FIG. 4A, the normal forces acting on the beam 345" by the adjustable cantilever device 344" will result in a substantially constant force F'". This substantially constant force F'" can supply a substantially constant pressure, i.e., the pre-set pressure, to fluid in a restriction system. A person skilled in the art will appreciate that the embodiment of the constant force mechanism 340" illustrated in FIGS. 4E and 4F can easily be incorporated into a variety of restriction systems, such as the restriction system 310' illustrated in FIGS. 4B and 4C, in much the same manner that the embodiment of the constant force mechanism 340 illustrated in FIG. 4A is incorporated to the restriction system 310' illustrated in FIGS. 4B and 4C as described above. Further, a person skilled in the art will also appreciate that in use, the constant force mechanism 340" illustrated in FIGS. 4E and 4F defines the pre-set pressure, and thus operates in much the same manner as described above with respect to the constant force mechanism 340 of FIG. 4A.

Figure 5:
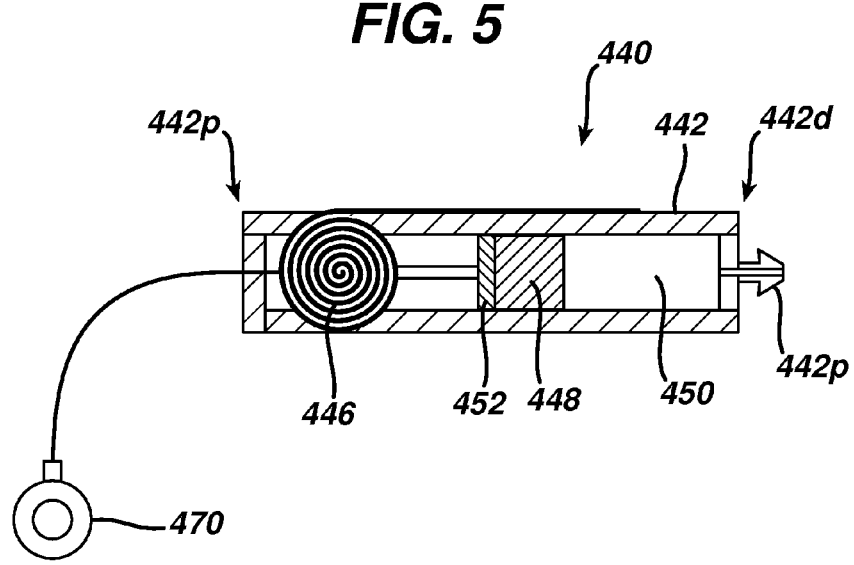
FIG. 5 is a cross-sectional view of another embodiment of a pressure adjustment unit having a constant force mechanism that includes a constant force spring coupled to a piston.

FIG. 5 illustrates another embodiment of a pressure adjustment unit 440 having a constant force mechanism disposed therein. As shown, the pressure adjustment unit 440 generally includes a chamber or housing 442 having proximal and distal ends 442p, 442d. The housing 442 includes a constant force spring 446 disposed in a proximal end 442p thereof, and a piston 452 disposed distal of and coupled to the constant force spring 446. In an exemplary embodiment, a portion of the constant force spring 446 is unwound and disposed along a portion of the housing 442 with a terminal end being fixedly attached to the housing 442. The housing 442 can include a slot formed therein adjacent to the unwound portion to allow the coiled portion of the constant force spring 446 to wind and unwind relative to the unwound portion. This allows the coiled portion, with the piston 452 coupled thereto, to move proximally and distally within the housing 442. Since the constant force spring 446 is biased to the coiled configuration, the spring 446 will apply a distally directed constant force to the piston 452, thereby applying a constant force to a fluid reservoir 450 located distal of the piston 452 and in fluid communication with a restriction device, e.g., via a port 442$p$ formed in the housing 442. The housing 442 can also optionally include an inflatable bladder 448 disposed therein and coupled to the piston 452 for adjusting a constant force of the constant force mechanism, as will be discussed in more detail below.

In use, the constant force spring 446 defines the pre-set pressure. When the pressure of the fluid in a restriction device drops below the pre-set pressure, the constant force spring 446 winds to push the piston 452 distally into the fluid reservoir 450 because the substantially constant pressure exceeds the decreased pressure of the fluid in the restriction device. As a result, fluid is pushed from the fluid reservoir 450 through the port 442$p$ and into the restriction device to raise the pressure of the fluid disposed therein. When the pressure of the fluid in the restriction device reaches the substantially constant pressure, an equilibrium is achieved and no fluid flows between the fluid reservoir 450 and the restriction device. Conversely, when the pressure of the fluid in the restriction device rises above the pre-set pressure, fluid can flow from the restriction device through the port 442$p$ and into the fluid reservoir 450. Flow of the fluid into the reservoir 450 moves the piston 452 proximally, thus causing the coiled portion of the constant force spring 446 to move proximally and be further unwound. The pressure in the restriction device will drop until it reaches the pre-set pressure, at which point no fluid flows between the reservoir 450 and the restriction device.

Figure 6:
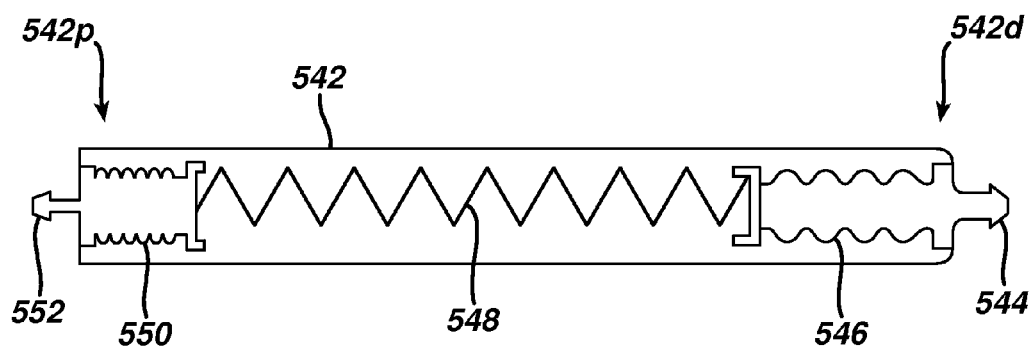
FIG. 6 is a cross-sectional view of yet another embodiment of a pressure adjustment unit having a constant force mechanism that includes a compression coil spring coupled to an expandable fluid bladder.

FIG. 6 illustrates yet another embodiment of a pressure adjustment unit having a housing 542 with proximal and distal ends 542$p$, 542$d$ and an access port 544 formed in the distal end 542$d$ thereof. A first fluid bladder, such as a first bellows 546, is disposed in the distal end 542$d$ of the housing 542 and is coupled to a spring 548. The spring 548 can extend between the first bellows 546 and a second bellows 550 which can be used to adjust a constant force of the spring, as will be discussed in more detail below, or alternatively the second bellows 550 can be removed and the proximal end of the spring 548 can be coupled to the proximal end of the housing 542. The first bellows 546 can be in fluid communication with the access port 544, which can be in communication with a restriction device. The first bellows 546 can both expand and contract based on a volume of fluid disposed therein (i.e., in responses to pressure changes in the restriction device). The spring 548 can have various configurations, but in an exemplary embodiment the spring 548 is a coil spring that is biased to an expanded position for applying a substantially constant force to the first bellows 546 to push fluid disposed therein from inside the first bellows 546, out of the access port 544, and into a restriction device coupled thereto.

In use, the spring 548 defines the pre-set pressure. When the pressure of the fluid in the restriction device drops below the pre-set pressure limit, the force applied to the bellows 546 by the spring 548 will exceed the force applied to the bellows 546 by the fluid therein and in communication with the restriction device. Thus the spring 548 will expand to compress the bellows 546. This will cause fluid disposed therein to leave the bellows 546 through the access port 544 and enter the restriction device to raise the pressure of the fluid disposed therein. When the pressure of the fluid in the restriction device reaches the pre-set pressure, an equilibrium is reached and no further expansion of the spring 548 and compression of the bellows 546 occurs. Conversely, when the pressure of the fluid in the restriction device rises above the pre-set pressure, the bellows 546 can expand to receive fluid from the restriction device thereby decreasing the pressure of fluid in the restriction device. The spring 548 will continuously act on the bellows 546 in response to changes in the fluid pressure in the restriction device to maintain a substantially constant pressure, i.e., the pre-set pressure, in the restriction device.

Figure 7A:
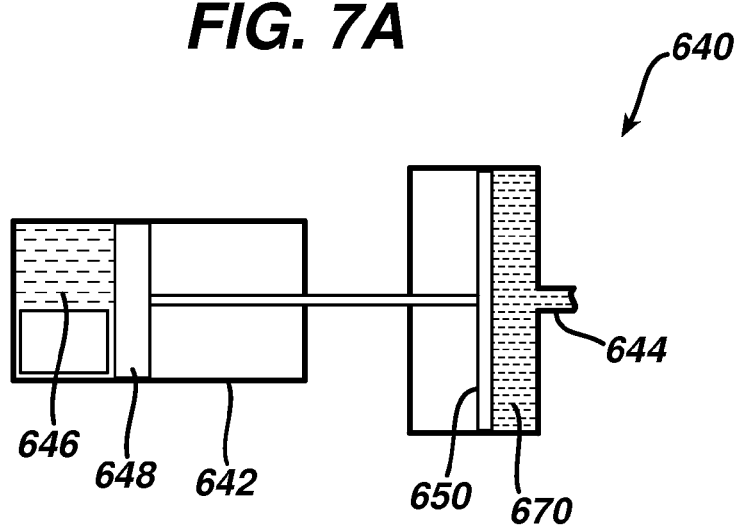
FIG. 7A is a cross-sectional view of a pressure adjustment unit having a constant force mechanism with a saturated fluid disposed in a chamber according to another embodiment.
Figure 7B:
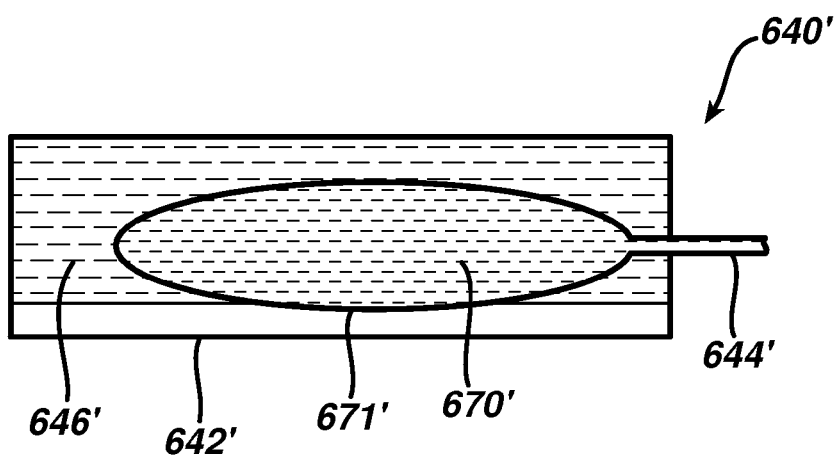
FIG. 7B is a cross-sectional view of yet another embodiment of a pressure adjustment unit having a constant force mechanism with a saturated fluid disposed in a chamber.

FIGS. 7A and 7B illustrate two other embodiments of pressure adjustment units 640, 640' having constant force mechanisms therein. Each pressure adjustment unit 640, 640' generally includes a housing or chamber 642, 642' containing a saturated fluid 646, 646' and a transfer mechanism for applying force to a fluid reservoir in fluid communication, e.g., through an access port 644, 644', with a restriction device. The saturated fluid 646, 646' can be any number of liquids or gases, but in one exemplary embodiment, the saturated fluid 646, 646' is DuPont Dymel aerosol propellant or butane. In the embodiment illustrated in FIG. 7A, the transfer mechanism is a first piston 648 disposed in the chamber 642 and coupled to a second piston 650 that is disposed in a fluid communication chamber or reservoir 670. As a volume of the saturated fluid 646 in the chamber 642 increases, the first piston 648 moves to the right thereby moving the second piston 650 to the right to push a portion of the fluid out of the reservoir 670 and through the access port 644 to increase a pressure of fluid in the restriction device. In the embodiment illustrated in FIG. 7B, the transfer mechanism is a flexible bladder 671' disposed within the chamber 642' and having a fluid reservoir 670' therein and in fluid communication with a restriction device.

In use, the saturated fluid 646, 646' defines the pre-set pressure. When the pressure of the fluid in the restriction device drops below the pre-set pressure, the transfer mechanism pushes fluid from the reservoir 670, 670' and into the restriction device to raise the pressure of the fluid disposed therein. Thus, in the embodiment illustrated in FIG. 7A, a pressure drop of the fluid in the restriction device results in the substantially constant pressure displacing the first piston 648 to the right, which in turn displaces the second piston 650 disposed in the fluid reservoir 670 to the right to push the fluid from the reservoir 670 through the access port 644 and into the restriction device. In the embodiment illustrated in FIG. 7B, a pressure drop of the fluid in the restriction device results in the substantially constant pressure compressing the bladder 671' disposed therein to push the fluid from the reservoir 670' through the access port 644' and into the restriction device. When the pressure of the fluid in the restriction device reaches the substantially constant pressure, an equilibrium is achieved and no fluid flows between the reservoir 670, 670' and the restriction device. Conversely, when the pressure of the fluid in the restriction device rises above the pre-set pressure, fluid can flow from the restriction device, through the access port 644, 644', and into the reservoir 670, 670'. Flow of the fluid into the reservoir 670, 670' can cause the volume of the reservoir 670, 670' to expand, which in turn causes the volume of the chamber 642, 642' containing the saturated fluid 646, 646' to contract. By allowing fluid to flow into the reservoir 670, 670', the pressure in the restriction device can drop until it reaches the pre-set pressure, at which point no fluid flows between the reservoir 670, 670' and the restriction device.

Figure 8:
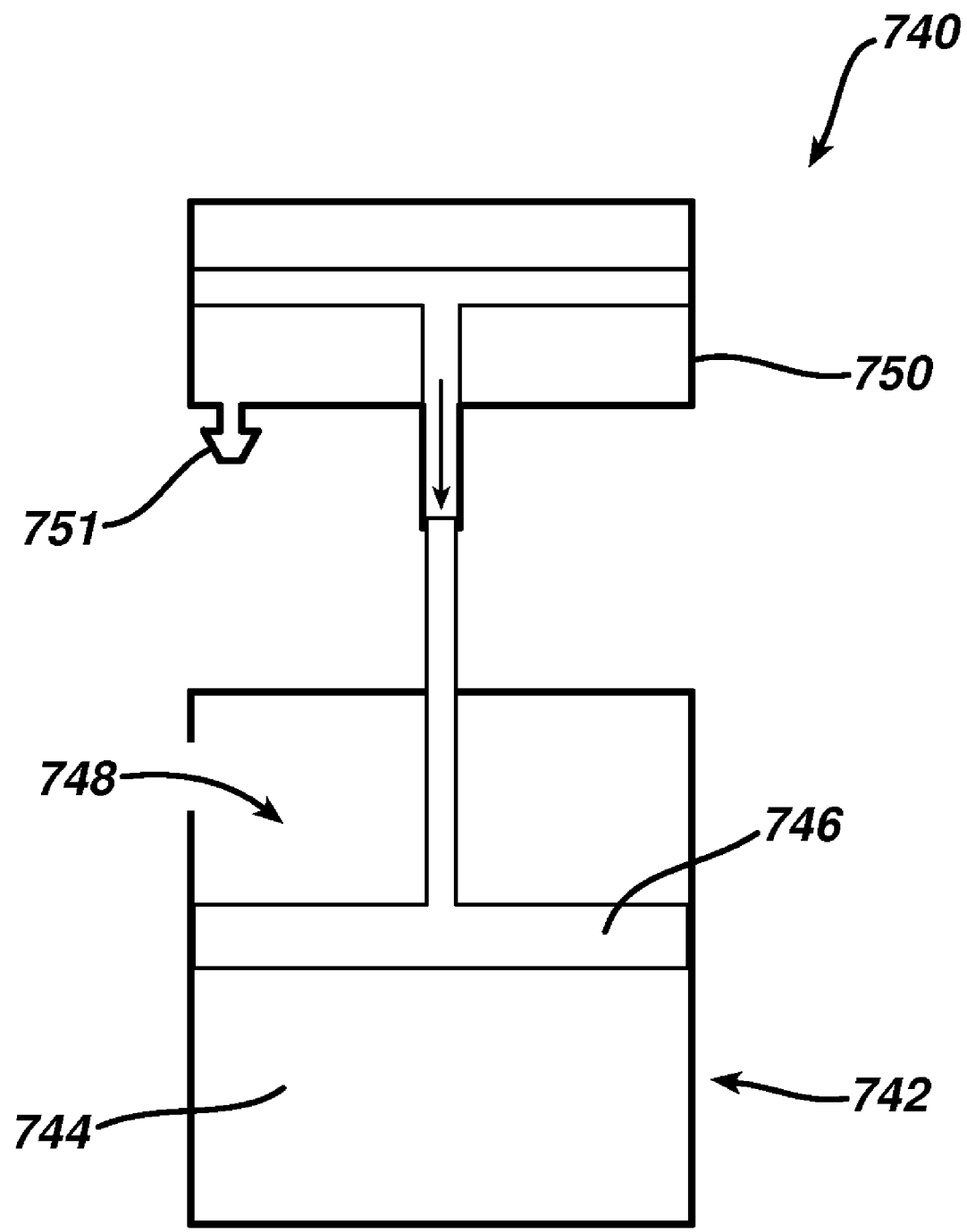
FIG. 8 is a cross-sectional view of another embodiment of a pressure adjustment unit having a constant force mechanism with a chamber under a vacuum force.

Another embodiment of a constant force mechanism 740 for use in a pressure adjustment unit is illustrated in FIG. 8. As shown, the constant force mechanism 740 generally includes a chamber or housing 742 with an evacuated volume 744, also referred to as a negative pressure or vacuum chamber. A piston 746 is disposed at least partially in the housing 742, and a fluid communication chamber, such as a reservoir 750, is coupled to the piston 746 and is in fluid communication with a restriction device, e.g., via an access port 751. The housing 742 is adapted to receive a force to act on the piston 746 and thus against the evacuated volume 744. In one embodiment, the housing 742 includes an opening 748 therethrough that is effective to receive a substantially constant pressure that is independent of volume, for instance atmospheric pressure, to act on the piston 746. Since the evacuated volume is disposed beneath the piston 746, the resulting force from the atmospheric pressure is provided independent of displacement of the piston 746. Accordingly, similar to the embodiments of FIGS. 7A and 7B that incorporate the saturated fluid 646, 646', this constant force mechanism 740 can maintain a substantially constant pressure, independent of volume, for a range of volumes. Accordingly, the resultant substantially constant pressure can be used as the pre-set pressure.

In use, the evacuated volume 744 defines the pre-set pressure. When the pressure of the fluid in the restriction device drops below the pre-set pressure, the piston 746 is displaced in an illustrated downward direction to cause fluid in the reservoir 750 to flow through the port 751 to the restriction device. When the pressure of the fluid in the restriction device reaches the substantially constant pressure, an equilibrium is achieved and no fluid flows between the reservoir 750 and the restriction device. Conversely, when the pressure of the fluid in the restriction device rises above the pre-set pressure, fluid can flow from the restriction device and into the reservoir 750. Flow of fluid into the reservoir 750 can cause the piston 746 to be displaced in the illustrated upward direction. By allowing fluid to flow into the reservoir 750, the pressure in the restriction device can drop until it reaches the pre-set pressure, at which point no fluid flows between the reservoir 750 and the restriction device.

FIGS. 9A-9D illustrate additional embodiments of a pressure adjustment unit having a constant force mechanism disposed therein. In these embodiments, the constant force mechanism is an osmotic pump. In the embodiment shown in FIG. 9A, the osmotic pump 840 generally includes a housing 842 with a proximal end 842$p$ having a semi-permeable membrane 846 formed therein and a distal end 842$d$ having an access port 844 formed therein. The semi-permeable membrane 846 can be adapted to allow fluid to flow into and out of the housing 842 while sealing dissolved species in the fluid contained in the housing 842 from the outside environment. In one exemplary embodiment, the semi-permeable membrane 846 is made of cellulose acetate. The housing 842 can further include an osmotic chamber 848 (sometimes referred to as an osmotic engine) having an osmotic substance, such as a salt-like solution, contained therein and in fluid communication with the semi-permeable membrane 846. In one exemplary embodiment, the osmotic substance can be disposed in the osmotic chamber 848 prior to receiving any fluid through the semi-permeable membrane 846. A piston 850 can be slidably disposed in the housing 842 and it can be in communication with the osmotic chamber 848 to receive a resulting substantially constant force created by osmotic pressure, which can result from a difference in concentration of dissolved species on opposite sides of the semi-permeable membrane 846, within the osmotic chamber 848. Slidable movement of the piston 850 can apply the resulting substantially constant force to a fluid 852 disposed in the housing 842, distal of the piston 850, to move the fluid 852 from the housing 842 through the access port 844 for delivery to a restriction device. Further, a biodegradable plug 854 can optionally be coupled to the semi-permeable membrane 846 at the proximal end 842$p$ for delaying fluid flow through the semi-permeable membrane 846 and/or into the osmotic chamber 848. The biodegradable plug can be made of a variety of materials capable of delaying the flow of fluid, but in one exemplary embodiment the plug 854 is made of polyactide or polyglycolide. Further, the size and shape of the plug 854 can vary depending on the desired delay. The osmotic pump 840 can also optionally be coupled to a port 870, which in the illustrated embodiment can be used to directly add fluid to the system. The location of the port 870 with respect to the osmotic pump 840 can vary, but in the illustrated embodiment the port 870 is located above the osmotic pump 840. In another embodiment, shown in FIG. 9B, the port 870' can be located substantially in-line with and proximal to the osmotic pump 840'. Likewise, other configurations between the osmotic pump and the port are possible, just as other configurations of the components of the osmotic pump are possible. For example, in embodiments that incorporate the biodegradable plug 854 the plug 854 can be disposed anywhere in the osmotic pump 840 that is effective to delay fluid flow, for example in the housing 842 near the access port 844.

In use, the osmotic pressure, which can be created by a difference in concentration of dissolved species on opposite sides of the semi-permeable membrane 846, within the osmotic chamber 848 of the osmotic pump 840 defines the pre-set pressure. When the pressure of the fluid in the restriction device drops below the pre-set pressure, the pressure within the osmotic chamber 848 also drops, and fluid is driven across the semi-permeable membrane 846, across an osmotic potential, and into the osmotic chamber 848 to push the piston 850 distally toward the access port 844 because the substantially constant pressure supplied by the osmotic pump 840 exceeds the decreased pressure of the fluid in the restriction device. Actuation of the piston 850 distally can cause the fluid 852 disposed distal thereof to be pushed distally through the access port 844 and into the restriction device to raise the pressure of the fluid disposed therein. When the pressure of the fluid in the restriction device reaches the substantially constant pressure, an equilibrium state is achieved where the pressure of the restriction device and the osmotic chamber 848 equals the osmotic pressure, and no fluid flows between the osmotic pump 840 and the restriction device. Conversely, when the pressure of the fluid in the restriction device rises above the pre-set pressure, fluid can flow from the restriction device through the access port 844 and into the distal end of the housing 842. Flow of the fluid into the distal end of the housing 842 can cause the piston 850 to be pushed in the proximal direction, and fluid within the osmotic chamber 848 can be forced through the semi-permeable membrane 846 in the proximal direction. By allowing fluid to flow into the housing 842, the pressure in the restriction device can drop until it reaches the pre-set pressure, at which point no fluid flows between the osmotic pump 840 and the restriction device. In an exemplary embodiment, the fluid is water.

In another embodiment, the osmotic pump 840 can be used to fill a restriction device, either initially or at some later point after implantation. More particularly, after the restriction device and pressure adjustment unit are implanted in a patient, fluid can flow through the semi-permeable membrane 846 and into the osmotic chamber 848 to be reacted to create a substantially constant force as described above. The inclusion of the biodegradable plug 854, however, can be effective to delay the time it takes for fluid to pass from outside of the osmotic pump 840, through the semi-permeable membrane 846, and into the osmotic chamber 848. As the fluid tries to flow into the osmotic chamber 848, the biodegradable plug 854 occludes such entry, but as the fluid erodes the biodegradable plug 854, 854', the fluid can slowly enter the osmotic chamber 848 and react as described above. Once the biodegradable plug 854 is substantially eroded, the osmotic pump 840 can operate substantially as described above. In an exemplary embodiment, the biodegradable plug 854 can be adapted to disintegrate over a four week period to gradually fill the restriction device.

Figure 9A:
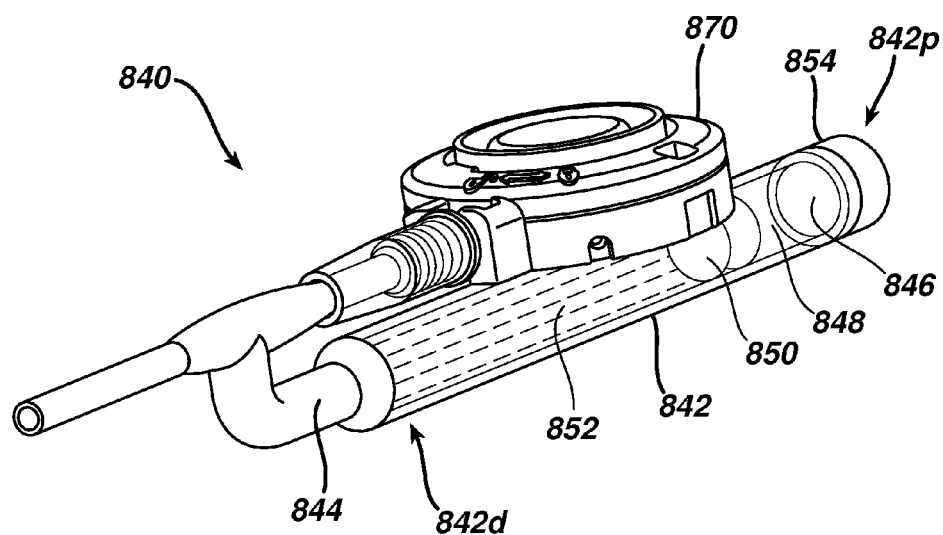
FIG. 9A is a perspective, partially transparent view of another embodiment of a pressure adjustment unit having a constant force mechanism that includes an osmotic pump.
Figure 9B:
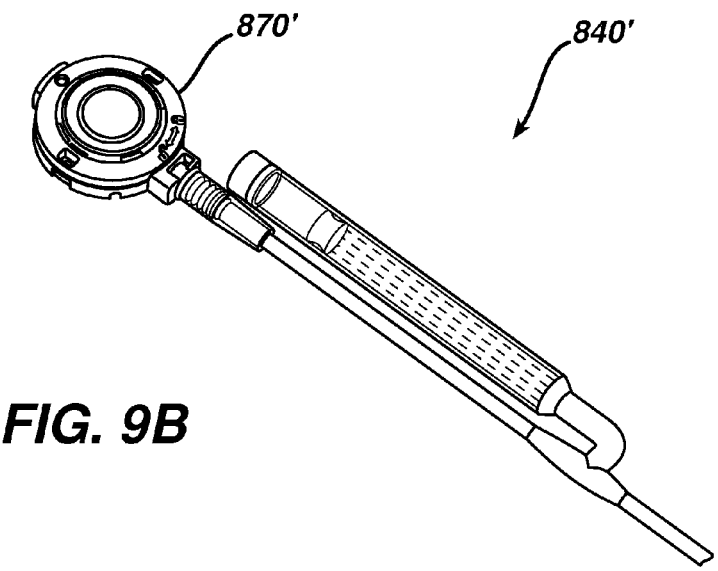
FIG. 9B is a perspective, partially transparent view of another embodiment of an osmotic pump for use with a constant force mechanism of a pressure adjustment unit in a restriction system.
Figure 9C:
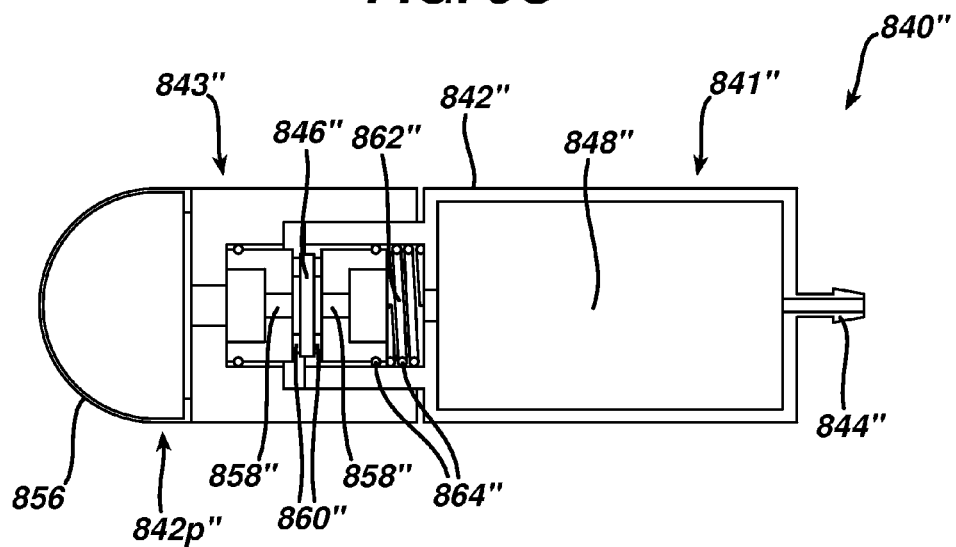
FIG. 9C is a cross-sectional view of yet another embodiment of an osmotic pump for use in a constant force mechanism of a pressure adjustment unit in a restriction system.
Figure 9D:
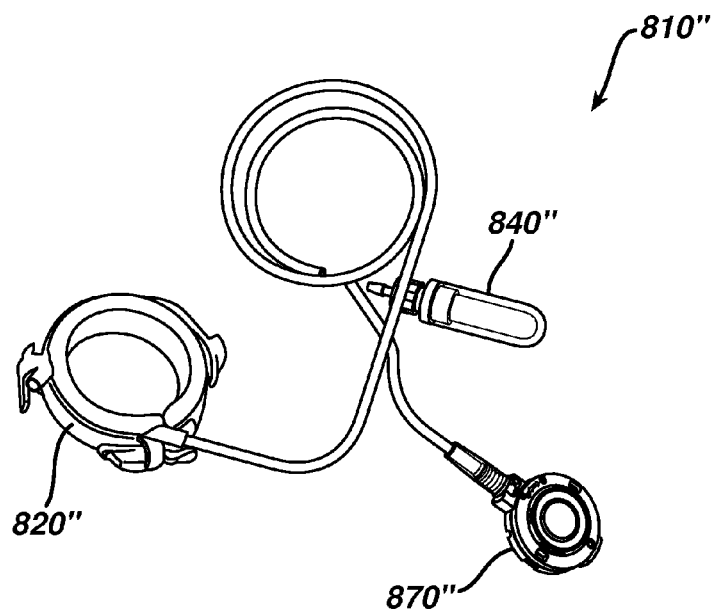
FIG. 9D is a perspective view of that osmotic pump of FIG. 9C coupled to a restriction system.

FIGS. 9C and 9D illustrate another embodiment of an osmotic pump 840". As shown, the osmotic pump 840" generally includes a housing 842" with a proximal end 842p" and a distal end 842d" having an access port 844" formed therein and coupled to a restriction device 820". Like the previous embodiment of the osmotic pump 840 of FIG. 9A, the housing 842" can include an osmotic chamber 848", but in this embodiment the osmotic chamber 848" is disposed in the distal end 842d" of the housing 842" and coupled to the access port 844". Consequently, fluid from the osmotic chamber 848" flows through the access port 844" and into the restriction device. A fluid chamber 856" and a semi-permeable membrane 846" can also be disposed in the housing 842". As shown, a fluid pathway 858" can extend from the fluid chamber 856" to the osmotic chamber 848" with the semi-permeable membrane 846" being disposed in the fluid pathway 858" and adapted to allow only fluid to flow bi-directionally from the fluid chamber 856" to the osmotic chamber 848", thereby sealing dissolved species contained in the fluid of the osmotic chamber 848" from the fluid chamber 856". Multiple gaskets 860" can be disposed on either side of the semi-permeable membrane 846" to provide further sealing between the fluid chamber 856" and the osmotic chamber 848". The fluid that flows from the fluid chamber 856" through the pathway 858" and into the osmotic chamber 848" can be any number of substances adapted to flow across an osmotic potential gradient and into the osmotic chamber 848", but in one embodiment the fluid is water. In another embodiment, the fluid chamber 856" can be a human body and the fluid 852" can be water derived from a bodily fluid. Thus, in such an embodiment the semi-permeable membrane 846" is exposed to the body and adapted to receive bodily fluid into the osmotic chamber 848".

For manufacturing purposes, the housing 842" can be constructed in two parts 841", 843", with the first part 841" containing the osmotic chamber 848" and the second part 843" containing the remaining components of the osmotic pump 840". While the two parts 841", 843" can be coupled in a number of different manners, in one embodiment they are threadably connected. Further, as illustrated, by connecting the two parts 841", 843" together, a compression force can be exerted on the gaskets 860". This force can be accentuated by disposing a spring 862" therein that is effective to compress the gaskets 860" against the semi-permeable membrane 846" to allow for proper sealing of the semi-permeable membrane. Further, to assist in maintaining the integrity of the fluid pathway 858", multiple o-rings 864" can be disposed around components such as the spring 862" and the gaskets 860" to maintain a desired location therein. Similar to the osmotic pumps 840, 840', the osmotic pump 840" can optionally be coupled to a port 870", which as described in further detail below can be used to alter the pre-set pressure and/or add fluid to a system 810".

While the pressure adjustment units described herein are generally adapted to produce a substantially constant force, and further, can be configured to regulate an amount of fluid flow between a reservoir and a restriction device based on a pre-set pressure (i.e., by maintaining a substantially constant pressure), it can be desirable to change the pre-set pressure of a pressure adjustment unit once the pressure adjustment unit has been implanted. As explained above, generally the pre-set pressure can be set prior to implantation, and preferably it is set on a patient-by-patient basis. However, as the anatomy of a patient changes, it is often the case that the original pre-set pressure is no longer the proper pre-set pressure for a particular patient. In order to set a new pre-set pressure, the pressure adjustment unit can be removed from the patient, recalibrated, and then re-implanted into the patient. However, it is preferred that such adjustments can occur non-invasively. Accordingly, various methods and devices are also provided for adjusting the pre-set pressure, preferably with the system still implanted. In general, a set-point adjustment mechanism is provided for allowing the pre-set pressure of a pressure adjustment unit to be changed non-invasively. A variety of different set-point adjustment mechanisms are described herein. A person skilled in the art will recognize that while some of the embodiments described are primarily applicable to a particular embodiment or pressure adjustment unit, other embodiments can be applied to most pressure adjustment units. Accordingly, a particular set-point adjustment mechanism discussed with respect to a particular pressure adjustment unit can also generally be used with other pressure adjustment units.

In one embodiment of a set-point adjustment mechanism 180, illustrated in FIGS. 2A and 2B, a housing 182 is provided having an expandable member 184 and a biasing mechanism disposed therein. The expandable member 184 can have a variety of configurations, such as an expandable balloon or fluid bladder. This biasing mechanism can also have a variety of configurations, but in the illustrated embodiment the biasing mechanism is a nitinol spring 186 axially disposed around at least a portion of the expandable member 184. As described with respect to the nitinol spring 140 of FIGS. 2A and 2B, nitinol has particular properties that make it ideal for use in a system that applies a substantially constant force over a given length of a spring. Accordingly, the nitinol spring 186 can be tuned to a particular set-point adjustment pressure such that the set-point adjustment mechanism is operable to change the pre-set pressure of the pressure adjustment unit 130 from an initial pre-set pressure, defined by the pre-set pressure, to an adjusted pre-set pressure, defined by the combination of the pre-set pressure and the set-point adjustment pressure. Further, a septum 188 adapted to receive a needle or other fluid delivery device can be located at a proximal end 182p of the housing 182 and it can be positioned adjacent to the expandable member 184 such that a fluid delivery device passed through the septum 188 can deliver fluid into and expand the expandable member 184. In one embodiment, the septum 188 is self-sealing which can allow a needle to penetrate the septum 188 without leaving an opening in the septum 188. An exit port 190 can be located at a distal end 182d of the housing 182 and it can be configured to allow fluid to flow between the expandable member 184 and the pressure adjustment unit 130. The pressure adjustment unit 130 can have a variety of different mechanisms configured to receive the fluid from the set-point adjustment mechanism 180 and thereby adjust a secondary force acting on the bellows 136 created by fluid flow from the set-point adjustment mechanism 180. For example, a piston can be located on a proximal end of the nitinol spring 140, or a piston can be mated to or formed on the bellows 136.

In use, the nitinol spring 186, in conjunction selectively with the secondary force acting on the bellows 136, defines the set-point adjustment pressure. The set-point adjustment pressure is the pressure at which the fluid from the expandable member 184 is pushed out of the expandable member 184, through the exit port 190, and into the pressure adjustment unit 130 by the substantially constant force of the nitinol spring 186. Alternatively, fluid can be pushed into the expandable member 184 from the pressure adjustment unit 130 to remove the secondary force acting on the bellows 136. To achieve the set-point adjustment pressure by adding fluid from the set-point adjustment mechanism 180 into the pressure adjustment unit 130, a fluid can be added to the expandable member 184 through the septum 188 to expand the expandable member 184. In one embodiment, prior to receiving fluid through the septum 188, the expandable member 184 is approximately empty and is thus in a deflated state. As fluid is added to the expandable member 184, a volume of the expandable member 184 increases and the expandable member 184 eventually contacts the nitinol spring 186 and expands it. However, because the spring 186 is made of nitinol, the force supplied by the spring 186 does not change as the spring 186 expands and thus the force remains a substantially constant force. Fluid can continue to be added to the expandable member 184 until the set-point adjustment pressure is achieved, at which point the nitinol spring 186 forces the fluid from the expandable member 184, through the exit port 190, and into the pressure adjustment unit 130. In the illustrated embodiment, when the fluid enters the pressure adjustment unit 130, the secondary force acts on the bellows 136, and in conjunction with the pressure created by the nitinol spring 140, creates the adjusted pre-set pressure. Accordingly, the addition of the fluid into the pressure adjustment unit 130 can change the pre-set pressure from the initial pre-set pressure, i.e. the pressure created by just the nitinol spring 140, to the adjusted pre-set pressure, i.e. the pressure created by the nitinol spring 140 and the secondary force acting on the bellows 136. Alternatively, the fluid creating the secondary force acting on the bellows 136 can be removed from the pressure adjustment unit 130 into the set-point adjustment mechanism 180 by removing fluid through the septum 188 to deflate the expandable member 184. Accordingly, the removal of the fluid from the pressure adjustment unit 130 can change the pre-set pressure from the adjusted pre-set pressure, i.e. the pressure created by the nitinol spring 140 and the secondary force acting on the bellows 136, to the initial pre-set pressure, i.e. the pressure created by just the nitinol spring 140. The set-point adjustment pressure of the set-point adjustment mechanism can vary from patient to patient, and thus the amount of fluid disposed in the expandable member 184 prior to achieving the set-point adjustment pressure can also change based on the patient. In one embodiment however, the expandable member 184 can expand such that substantially all available space in the housing 182 is filled by the expandable member 184 disposed with fluid therein. When there is no further room for expansion, the set-point adjustment pressure can be achieved and the fluid can flow from the expandable member 184, through the exit port 190, and into the pressure adjustment unit 130.

In another embodiment, as shown in FIGS. 3A-3C, the pre-set pressure of the pressure adjustment mechanism 230 can be adjusted by changing the tension of the torsion spring 250. For example, the housing 232 can include a port 270 (FIG. 3A) coupled thereto for receiving fluid. A connector 260 can extend between the port 270 and the housing 232 and it can include a plug 254 movably disposed therein and coupled to a rotatable housing 258 that is rotatably disposed within housing 232. For example, a string 256 or other member can extend between the plug 254 and the housing 258. A terminal end 252 of the torsion spring 250 can be coupled to the rotatable housing 232. As a result, fluid added to and/or removed from the port 270 and the connector 260 will cause corresponding movement of the plug 254, which in turn will cause rotation of the rotatable housing 258. As a result, the torsion spring 250 will wind or unwind with the housing 258, and thus the tension of the torsion spring 250 will be adjusted.

In another embodiment, shown in FIG. 4A, the pre-set pressure can be adjusted by altering the substantially constant force F of the constant force mechanism. At least because the substantially constant force F can define the pre-set pressure, any adjustment to the constant force mechanism that contributes to creating the substantially constant force F can be effective to adjust the pre-set pressure. This is illustrated, for example, in FIGS. 4B and 4C. Changing the force applied to the bearing element 350' by the cantilevered beam 352' can be effective to change the pre-set pressure because together they define the pre-set pressure. As shown, a lever 356' is slidably positioned relative to the cantilevered beam 352' and is configured to change an effective length of the cantilevered beam 352' by sliding over a desired portion of the cantilevered beam 352'. Changing the effective length of the cantilevered beam 352' can change a normal force applied by the cantilevered beam 352' to the bearing element 350', which results in a changed substantially constant force F'. In one embodiment, the lever 356' can be coupled to a slidable block 358' and the slidable block 358' can be coupled to a means to supply linear motion. In the illustrated embodiment, the means to supply linear motion is a fluid system in which the slidable block 358' is disposed in a fluid chamber 360' that is configured to receive a fluid to slidably move the block 358' within the fluid chamber 360' to create slidable movement of the lever 356' attached thereto. In use, as fluid is added to or removed from the fluid chamber 360', the slidable block 358', and hence the lever 356', can move between a first position, illustrated in FIG. 4B, in which the lever 356' is spaced apart from or out of contact with the cantilevered beam 352', and a second position, illustrated in FIG. 4C, in which the lever 356' slides forward over a portion of the cantilevered beam 352' to shorten the effective length of the beam 352' and thereby increase the substantially constant force F' applied by the beam 352'. As shown in FIG. 4C, when the lever 356' is advanced over the cantilevered beam 352' to change the substantially constant force F', the cantilevered beam 352' is deflected thereby decreasing an effective length thereof and resulting in an increase to the substantially constant force F'.

FIG. 4D illustrates yet another embodiment of a constant force mechanism 340''', similar to the constant force mechanism 340' of FIGS. 4B and 4C, that could also be incorporated into a restriction system similar to the restriction system 310' of FIGS. 4B and 4C. In this embodiment, the constant force mechanism 340''' includes a clamp mechanism 356''' for adjusting an effective length of the cantilevered beam 352'''. The clamping mechanism 356''' can be slidably disposed around the cantilevered beam 352''' and a base 358''' coupled to one end of the cantilever beam 352'''. As the clamping mechanism 356''' slides along the cantilevered beam 352''' and base 358'''' toward the cam surface 348''', the beam 352''' is pulled toward the base 358''' and as a result the effective length of the cantilevered beam 352''' is decreased, thus decreasing the value of the substantially constant force F'''.

In another embodiment, shown in FIGS. 4E and 4F, the substantially constant force F'' can be adjusted by changing the tension of the spring 350''. In particular, a height of the beam 345'' can be increased or decreased to alter tension on the spring 350''. As illustrated, a proximal end 345p'' of the cantilevered beam 345'' can be pivotally coupled to a sidearm on the base 345b'' and a rotational element 356'' can be positioned just beneath the beam 345'' such that rotation of the rotational element 356'' adjusts the height of the beam 345''. A linkage 358'' can be disposed between the rotational element 356'' and the cantilevered beam 345'' to assist in translating movement of the rotational element 356'' to the cantilevered beam 345''. In use, rotation of the rotational element 356'' raises and lowers the cantilevered beam 345'' to change an angle θ'' of the cam surface 348'' while simultaneously increasing or decreasing the tension of the spring 350'' to adjust the substantially constant force F''. As illustrated, clockwise rotation of the rotational element 356'' lowers the cantilevered beam 345'' and thus the value of the substantially constant force F', and counterclockwise rotation of the rotational element 356'' raises the cantilevered beam 345'' and thus increases the value of the substantially constant force F'''.

In another embodiment, a pre-set pressure of the pressure adjustment unit 440 of FIG. 5 can be changed using friction. For example, the piston 452 can include the inflatable bladder 448 coupled thereto and in communication with a port 470. Adding fluid into the bladder 448 via the port 40 will increase a volume of the inflatable bladder 448. As the inflatable bladder 448 expands against the housing 442 an amount of friction between the inflatable bladder 448 and the housing increases. The friction affects the ability for the piston 452 to move, thus altering the pre-set pressure.

The pressure adjustment unit 540 of FIG. 6 can also have its pre-set pressure adjusted. As previously indicated, the pressure adjustment unit 540 can include a second bellows 550 coupled to the proximal end of the spring 548. The second bellows 550 can be coupled to a second access port 552 formed in the proximal end 542p of the housing 542. To adjust the pre-set pressure, fluid can be added to or removed from the second bellows 550 to adjust a length of the spring 548 coupled thereto. Because the spring 548 defines the pre-set pressure, as its length changes, so does the pre-set pressure.

Pre-set pressures for the embodiments illustrated in FIGS. 7A and 7B can also be adjusted. In one exemplary embodiment, a composition of the saturated fluid 646, 646' can be changed. In another embodiment a concentration of the saturated fluid 646, 646' can be changed. Although not illustrated, either of these actions can be accomplished by connecting a port to the chamber 642, 642' containing the saturated fluid 646, 646' is disposed such that the composition and/or concentration of the saturated fluid can be changed by adding and/or removing fluid from the chamber 642, 642'. When the composition and/or concentration of the saturated fluid 646, 646' is changed, the pre-set pressure of the pressure adjustment units 640, 640' can also be changed, at least because the saturated fluid 646, 646' defines the pre-set pressure.

Similarly, the pre-set pressure for the embodiment illustrated in FIG. 8 can also be adjusted by changing a negative pressure of the evacuated volume 744, since the evacuated volume 744 defines the pre-set pressure. Although not illustrated, this too can be accomplished by connecting a port to the chamber 742 to access the evacuated volume 744.

The pre-set pressure of the osmotic pumps 840, 840', and 840'' of FIGS. 9A-9D can also be adjusted in a variety of ways, but at least because the osmotic pressure of the osmotic chamber 848, 848', 848'' defines the pre-set pressure, changes to the concentration of dissolved species in the fluid in the osmotic chamber 848, 848', 848'' will also affect the pre-set pressure. For example, changing the molarity of the osmotic fluid contained in the osmotic chamber 848, 848', 848''' can be effective to adjust the pre-set pressure. A port 870, 870', 870'' in communication with the osmotic chamber 848, 848', 848'' can be effective to change the molarity of the osmotic solution in a non-invasive manner.

Figure 10:
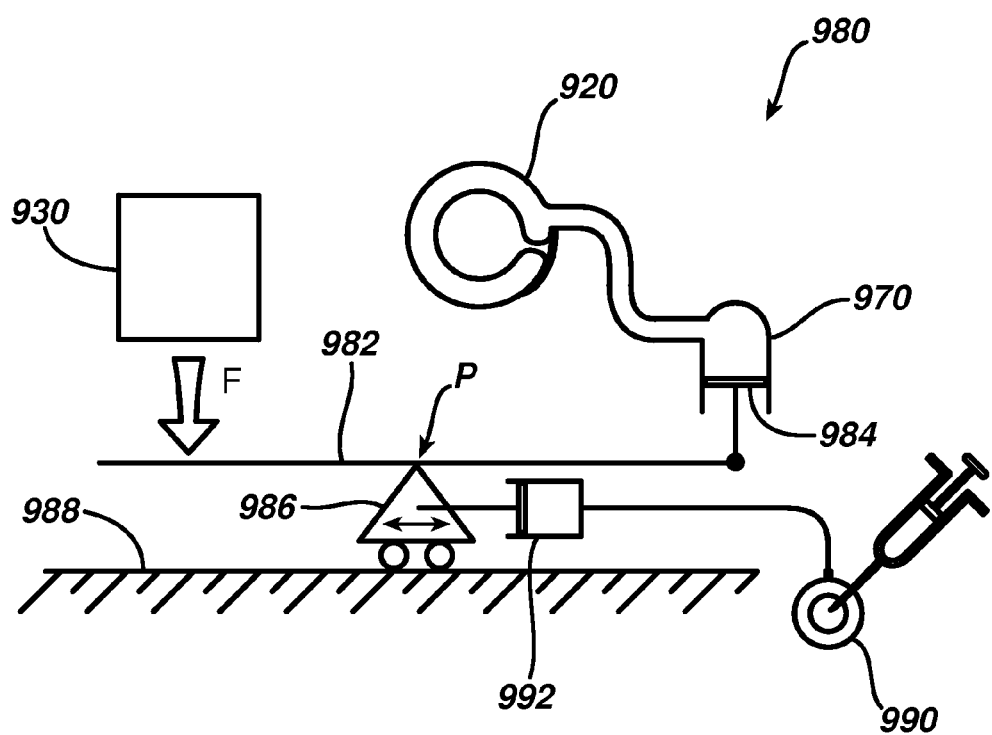
FIG. 10 is a schematic diagram illustrating one exemplary embodiment of a set-point adjustment mechanism.

Yet another embodiment of a set-point adjustment mechanism 980 is illustrated in FIG. 10. Generally, each of the pressure adjustment units described herein include a constant force mechanism. Each of these constant force mechanisms, represented in FIG. 10 in their entirety by constant force mechanism 930 supply a substantially constant force F. While many of the set-point adjustment mechanisms disclosed herein teach ways to adjust individual components of the constant force mechanisms or pressure adjustment units, the set-point adjustment mechanism 980 can be generally applied to each and every embodiment disclosed because it is effective to adjust the resultant substantially constant force F once it leaves the constant force mechanism 930 and is communicated to another component, for example a fluid reservoir 970 in communication with a restriction device 920. A means to transfer the substantially constant force F from the constant force mechanism 930 to the fluid reservoir 970 can be disposed therebetween, and in the illustrated embodiment is a lever 982 having a piston 984 coupled to one end thereof and adapted to push fluid from the fluid reservoir 970 into the restriction device 920 based on the substantially constant force F of the constant force mechanism 930. A fulcrum 986 can be coupled to the lever 982 and it can be movable relative to the lever 982 to adjust a fulcrum point P of the lever 982. While the fulcrum 986 can be movable in a variety of ways, as shown it is slidably coupled to a surface 988. A fluid port 990 can be in fluid communication with the fulcrum 986 by a transfer mechanism 992 and it can be adapted to cause movement of the fulcrum 986 along the surface 988 and relative to the lever 982 to change a location of the fulcrum point P. In particular, as fluid is added to or removed from the port 990 and delivered to the fluid transfer mechanism 992, a piston disposed within the fluid transfer mechanism 992 and coupled to the fulcrum 986 moves to thereby slide the fulcrum 986. Changing the location of the fulcrum point P subsequently adjusts the mechanical advantage of the system to thus change the amount of the substantially constant force F that is actually applied to the fluid reservoir 970. While the optimal location for the fulcrum point P depends on a number of factors, including the amount of force acting on each portion of the lever 982, in an embodiment where the forces acting on each side of the lever 982 are equal, the optimal location for the fulcrum point P is the center of the lever 982. When the fulcrum point P is at the optimal location, the greatest amount of the substantially constant force F is transferred to the fluid reservoir 970. However, because the system is not constant or static, the optimal location for the fulcrum point P will generally consistently change, which in turn means the fulcrum 986 should consistently be moved in order to maintain a desired efficiency of the system.

In use, when fluid from the fluid port 990 is added to the fulcrum 986, the fulcrum 986 moves to the left and the amount of the substantially constant force F that is transferred to the fluid reservoir 970 increases or decreases, depending on the location of the optimal fulcrum point. When fluid is then removed from the fulcrum 986, the fulcrum 986 moves to the right, allowing the amount of the substantially constant force F that is transferred to the fluid reservoir 970 to increase or decrease, again depending on the location of the optimal fulcrum point. In practice, the optimal location for fulcrum point P will likely be fluid as the system is operated, and thus, fluid can be selectively added to and removed from the fulcrum 986 to achieve a desired result from a desired location.

To the extent that any of the pressure adjustment units, constant force mechanisms, and set-point adjustment mechanisms incorporate springs or other mechanical components that can be adjusted to provide different dimensions or properties (such as spring constants), a person skilled in the art will appreciate that changes to many of the properties and dimensions will affect the performance of the respective pressure adjustment units, constant force mechanisms, and set-point adjustment mechanisms. Accordingly, even if changes to these types of components are not discussed above, such changes could be incorporated into many of the pressure adjustment units, constant force mechanisms, and set-point adjustment mechanisms to affect the desired performance of each.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK® (available from DuPont of Wilmington, Del.) bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A self-regulating restriction system, comprising:
a restriction device for forming a restriction in a pathway;
a pressure adjustment unit in communication with the restriction device and effective to maintain a substantially constant equilibrium pressure between the restriction device and the pressure adjustment unit by regulating an amount of fluid in the restriction device, the pressure adjustment unit having a housing with a constant force mechanism and an expandable bellows disposed therein, the expandable bellows being in fluid communication with the restriction device, and the constant force mechanism applying a constant force to the expandable bellows; and
a set-point adjustment mechanism having an expandable bladder and a constant pressure spring, the set-point adjustment mechanism being aligned along a longitudinal axis with the pressure adjustment unit housing, the expandable bladder being inflatable to adjust the substantially constant equilibrium pressure, and the constant pressure spring being at least partially disposed around the expandable bladder.

2. The system of claim 1, wherein the constant force mechanism comprises a nitinol spring.

3. A system for automatically adjusting a restriction device, comprising:
a housing;
an expandable bellows defining a fluid reservoir disposed in the housing;
a restriction device in fluid communication with the fluid reservoir and configured to form a restriction in a pathway that corresponds to an amount of fluid contained within the restriction device;
a constant force mechanism disposed in the housing, the constant force mechanism being coupled to the fluid reservoir and configured to apply a substantially constant force to the fluid reservoir to maintain a substantially constant pressure in the restriction device; and
a set-point adjustment unit having an expandable bladder disposed therein, the set-point adjustment unit being aligned along a longitudinal axis with the housing, the set-point adjustment unit being coupled to the constant force mechanism and configured to change the substantially constant force applied by the constant force mechanism.

4. The system of claim 3, wherein the constant force mechanism comprises a constant pressure spring.

5. The system of claim 3, wherein the restriction device includes a fluid bladder for containing fluid therein.

6. A self-regulating restriction system, comprising:
a restriction device for forming a restriction in a pathway;
a pressure adjustment unit in communication with the restriction device and effective to maintain a substantially constant equilibrium pressure between the restriction device and the pressure adjustment unit by regulating an amount of fluid in the restriction device, the pressure adjustment unit having a first constant pressure spring configured to apply a substantially constant pressure in the restriction device; and
a set-point adjustment mechanism having an expandable bladder and a second constant pressure spring, the set-point adjustment mechanism being aligned along a longitudinal axis with the pressure adjustment unit, the expandable bladder being inflatable to adjust the substantially constant equilibrium pressure, and the second constant pressure spring being at least partially disposed around the expandable bladder.

7. The system of claim 6, wherein at least one of the first and second constant pressure spring is a nitinol spring.

8. The system of claim 6, wherein the first constant pressure spring is disposed between the restriction device and the expandable bladder.

9. The system of claim 6, wherein the first constant pressure spring is disposed in a chamber and coupled to a piston.

* * * * *